United States Patent
Zahler et al.

(10) Patent No.: US 9,643,933 B2
(45) Date of Patent: May 9, 2017

(54) COMPOUNDS USEFUL AS ANTIBIOTIC TOLERANCE INHIBITORS

(71) Applicant: The General Hospital Corporation, Boston, MA (US)

(72) Inventors: Robert Zahler, Pennington, NJ (US); Ronald Thure Wester, Ledyard, CT (US); Steven Joseph Brickner, Ledyard, CT (US)

(73) Assignees: The General Hospital Corporation, Boston, MA (US); Institut National de la Recherche Scientifique, Quebec (CA)

( * ) Notice: Subject to any disclaimer, the term of this patent is extended or adjusted under 35 U.S.C. 154(b) by 0 days.

(21) Appl. No.: 14/786,345

(22) PCT Filed: Apr. 22, 2014

(86) PCT No.: PCT/US2014/034998
§ 371 (c)(1),
(2) Date: Oct. 22, 2015

(87) PCT Pub. No.: WO2014/176258
PCT Pub. Date: Oct. 30, 2014

(65) Prior Publication Data
US 2016/0052890 A1 Feb. 25, 2016

Related U.S. Application Data

(60) Provisional application No. 61/815,260, filed on Apr. 23, 2013, provisional application No. 61/951,340, filed on Mar. 11, 2014.

(51) Int. Cl.
| | | |
|---|---|---|
| C07D 235/08 | (2006.01) |
| C07D 235/28 | (2006.01) |
| C07D 401/12 | (2006.01) |
| C07D 403/12 | (2006.01) |
| C07D 235/16 | (2006.01) |
| C07D 235/26 | (2006.01) |
| C07D 235/30 | (2006.01) |
| C07D 403/04 | (2006.01) |
| C07D 405/12 | (2006.01) |
| C07D 413/04 | (2006.01) |
| C07D 413/12 | (2006.01) |
| C07D 471/04 | (2006.01) |
| C07D 263/58 | (2006.01) |
| C07D 417/12 | (2006.01) |

(52) U.S. Cl.
CPC ........ *C07D 235/28* (2013.01); *C07D 235/16* (2013.01); *C07D 235/26* (2013.01); *C07D 235/30* (2013.01); *C07D 263/58* (2013.01); *C07D 401/12* (2013.01); *C07D 403/04* (2013.01); *C07D 403/12* (2013.01); *C07D 405/12* (2013.01); *C07D 413/04* (2013.01); *C07D 413/12* (2013.01); *C07D 417/12* (2013.01); *C07D 471/04* (2013.01)

(58) Field of Classification Search
CPC ................ C07D 235/28; C07D 235/16; C07D 2401/12; C07D 403/12
See application file for complete search history.

(56) References Cited

U.S. PATENT DOCUMENTS

2014/0066454 A1  3/2014  Rahme et al.

FOREIGN PATENT DOCUMENTS

WO  WO 2012/116010  8/2012

OTHER PUBLICATIONS

French 'Bactericidal agents in the treatment of MRSA infections—the potential role of daptomycin' Journal of Antimicrobial Chemotherapy, vol. 58, p. 1107-1117, 2006.*
Database Registry, Chemical Abstracts Service, Jan. 2003, XP002726338.
El-Helby, "Synthesis and anticonvulsant activity of 2-substituted-5-chlorobenzoxazole," Pakistan Journal of Scientific and Industrial Research, Jul. 2002, 45(4):219-225.

(Continued)

*Primary Examiner* — Wu-Cheng Winston Shen
*Assistant Examiner* — Christopher R Stone
(74) *Attorney, Agent, or Firm* — Fish & Richardson P.C.

(57) ABSTRACT

The disclosure provides compounds and pharmaceutical compositions of the compounds useful for treating chronic and acute bacterial infections. Certain of the compounds are compounds and salts of general Formula VIII Certain compounds of this disclosure are MvfR inhibitors. MvfR inhibitors reduce the formation of antibiotic tolerant bacterial strains and are useful for treating Gram-negative bacterial infections and reducing the virulence of *Pseudomonas aeruginosa*. Methods of treating bacterial infections in a patient, including *Pseudomonas aeruginosa* infections, are also provided by the disclosure.

(VIII)

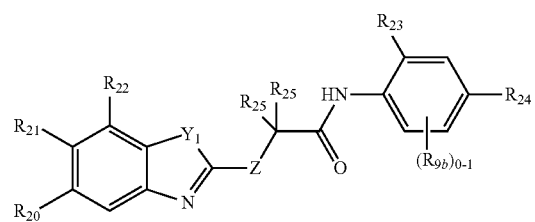

11 Claims, No Drawings

(56) References Cited

OTHER PUBLICATIONS

El-Sherief et al., "Synthesis of Some New Benzoxazole, Benzthiazole, and Benzimidazole Derivatives with Biological Activity," Journal of the Indian Chemical Society, Jan. 1983, 60:58-60.
International Preliminary Report on Patentability in International Application No. PCT/US4014/034998, dated Oct. 27, 2015, 13 pages.
International Search Report and Written Opinion in International Application No. PCT/UUS2014/034998, dated Oct. 9, 2014, 19 pages.
Massarotti et al., "Identification of Novel Antitubulin Agents by Using a Virtual Screening Approach Based on a 7-Point Pharmacophore Model of the Tubulin Colchi-Site," Chemical Biology & Drug Design, Dec. 2011, 78:913-922.
Ozkay et al., "Antimicrobial Activity of a New Combination System of Benzimidazole and Various Azoles," Archiv Der Pharmazie, Apr. 2011, 344(4):264-271.
Parikh et al., "Antibacterial and antifungal screening of newly synthesized benzimidazole-clubbed chalcone derivatives," Medicinal Chemistry Research, Nov. 2012, 22(8):3688-3697.
Pattan et al., "Synthesis and biological activity of 7-chloro-(6-fluoro-benzothiazole)-2- amino(substituted) acetanilides," Indian Drugs, Oct. 2002, 39(10):515-517.
Perdih et al., "Discovery of novel benzene 1,3-dicarboxylic acid inhibitors of bacterial MurD and MurE ligases by structure-based virtual screening approach," Bioorganic & Medicinal Chemistry Letters, May 2009, 19(10):2668-2673.
Sorci et al., "Chemistry & Biology 16 Supplemental Data Targeting NAD Biosynthesis in Bacterial Pathogens: Structure-Based Development of Inhibitors of Nicotinate Mononucleotide Adenylyltransferase NadD Supplemental Experimental Procedures System Preparation for in silico Database Screening," Aug. 28, 2009 (Aug. 28, 2009), XP055124472, Retrieved from the Internet: URL:http://www.sciencedirect.com/science/MiamiMultiMediaURL/1-s2.O-S1O745521O9O02166/1-s2.0-S1074552109002166~nine1.pdf/27022/FULL/S1074552109002166/46d147a5c661b2b9c9c86966ce8b9c2c/mmcl.pdf [retrieved on Jun. 20, 2014].
Sorci et al., "Targeting Nad Biosynthesis in Bacterial Pathogens: Structure-Based Development of Inhibitors of Nicotinate Mononucleotide Adenylyltransferase NadD," Chemistry and Biology, Aug. 2009, 16(8):849-861.
Toyofuku et al., "The Effect of a Cell-to-Cell Communication Molecule, Pseudomonas Quinolone Signal (PQS), Produced by P. aeruginosa on Other Bacterial Species," Microbes Environ., 2010, 25(1):1-7.

\* cited by examiner

COMPOUNDS USEFUL AS ANTIBIOTIC TOLERANCE INHIBITORS

CROSS REFERENCE TO RELATED APPLICATION

This application is a U.S. National Phase Application under 35 U.S.C. §371 of International Patent Application No. PCT/US2014/034998, filed on Apr. 22, 2014, which claims the benefit of U.S. Provisional Applications No. 61/815,260, filed Apr. 23, 2013, and No. 61/951,340, filed Mar. 11, 2014, bet-hall of which are hereby incorporated by reference in their entireties.

TECHNICAL FIELD

The present disclosure includes substituted benzimidazole-benzamides and related compounds and methods of using such compounds. For example, the disclosure provides methods of using the compounds in treating acute and chronic bacterial infections.

BACKGROUND

Hard-to-eradicate, often untreatable, infections including chronic wounds and infections of medical devices pose increasing threats to human health worldwide. Such infections are often refractory to antibiotics due to antibiotic resistant bacterial cells, and/or to antibiotic tolerance of a subpopulation of bacterial cells that are not antibiotic resistant mutants but rather "dormant" cells that survive antibiotic killing. Antibiotic tolerance is defined as the ability of a fraction of a susceptible bacterial population to survive exposure to normally lethal concentrations of bactericidal antibiotics. According to the existing paradigm, many chronic infections are therefore untreatable.

The ligand activated transcriptional regulator, MvfR, plays a central role in controlling the pathology of acute bacterial infections, and the shift of Gram-negative bacteria from acute to chronic infection. MvfR inhibitors reduce virulence of *Pseudomonas aeruginosa*, a Gram-negative bacterial species, and reduce the formation of antibiotic resistant *Pseudomonas* strains in vitro.

SUMMARY

In a first embodiment, this disclosure includes compounds of Formula (I) and the pharmaceutically acceptable salts thereof. In this embodiment the 6-membered carbocyclic ring of the bicyclic heteroaryl group shown in Formula (I) is substituted with at least one substituent that is not nitro, $C_1$-$C_6$alkyl, $C_1$-$C_6$alkoxy, N-linked carboxamide, N-linked alkyl carboxamide, or N-linked alkyl carboxamide substituted with halogen.

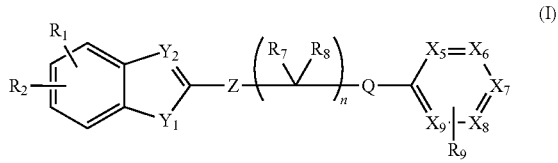

(I)

In this first embodiment the variables, e.g. $R_1$ to $R_9$, $Y_1$, $Y_2$, Z, n, and $X_5$ to $X_9$ carry the following definitions.

$R_1$ is one substituent chosen from (i), (ii), and (iii).

(i) is halogen, hydroxyl, cyano, azido, amino, —$CONH_2$, $C_1$-$C_6$haloalkyl, and $C_1$-$C_6$haloalkoxy.

(ii) is $C_2$-$C_8$alkenyl, $C_2$-$C_8$alkynyl, —$(CH_2)_{2-4}C(O)R_{11}$, —$(CH_2)_{0-4}C(S)R_{11}$, —$(CH_2)_{0-4}NR_{11}R_{12}$, —$(CH_2)_{0-4}C(O)OR_{11}$, —$(CH_2)_{0-4}OC(O)R_{11}$, —$(CH_2)_{0-4}C(S)SR_{11}$, —$(CH_2)_{0-4}SC(S)R_{11}$, —$(CH_2)_{0-4}OC(O)NR_{11}R_{12}$, —$(CH_2)_{0-4}N(R_{11})COR_{12}$, —$(CH_2)_{0-4}N(R_{11})C(O)NR_{12}R_{13}$, —$(CH_2)_{0-4}N(R_{11})OC(O)R_{12}$, —$(CH_2)_{0-4}C(O)SR_{11}$, —$(CH_2)_{0-4}S(O)_aR_{11}$, —$(CH_2)_{0-4}N(R_{11})NR_{12}R_{13}$, —$(CH_2)_{0-4}S(O)_bNR_{11}R_{12}$, —$(CH_2)_{0-4}N(R_{11})S(O)_bR_{12}$, —$(CH_2)_{0-4}S(O)_2ONR_{11}$, —$(CH_2)_{0-4}OS(O)_2NR_{11}$, —$N(R_{11})C(S)R_{12}$, —$C(S)NR_{11}$, —$C(S)SR_{11}$, —$(CH_2)_{0-4}N(R_{11})C(S)NR_{12}R_{13}$, —$(CH_2)_{0-4}S(O)_2OR_{11}$, —$(CH_2)_{0-4}OS(O)R_{11}$, $(CH_2)_{0-4}N(C_1$-$C_8$alkyl)C(O)($C_1$-$C_8$alkyl), —$(CH_2)_{0-4}C(O)NR_{11}R_{12}$, —$(CH_2)_{0-4}$(carbocycle), —$O(CH_2)_{0-4}$(carbocycle), —$S(O)_m(CH_2)_{0-4}$(carbocycle), —$(CH_2)_{0-4}$(heterocycle), —$O(CH_2)_{0-4}$(heterocycle), and —$S(O)_m(CH_2)_{0-4}$(heterocycle), wherein a is independently chosen from 0, 1, and 2; b is independently chosen from 1 and 2; and m is independently chosen from 0, 1, and 2. $R_{11}$, $R_{12}$, and $R_{13}$ are independently chosen at each occurrence from hydrogen and a $C_1$-$C_8$aliphatic group. Each of (ii) is optionally substituted on any carbon available for substitution with one or more substituents independently chosen from: halogen, hydroxyl, vinyl, allenyl, oxo, cyano, amino, —COOH, $C_1$-$C_6$alkyl, $C_1$-$C_6$alkoxy, (mono- and di-$C_1$-$C_6$alkylamino)$C_0$-$C_2$alkyl, $C_1$-$C_6$alkylester, $C_1$-$C_6$alkylthio, $C_1$-$C_2$haloalkyl, and $C_1$-$C_2$haloalkoxy.

(iii) is $C_1$-$C_8$alkyl or $C_1$-$C_8$alkoxy, each of which is substituted with one or more substituents independently chosen from halogen, hydroxyl, vinyl, allenyl, oxo, cyano, amino, —COOH, $C_1$-$C_6$alkoxy, (mono- and di-$C_1$-$C_6$alkylamino)$C_0$-$C_2$alkyl, $C_1$-$C_6$alkylester, $C_1$-$C_6$alkylthio, $C_1$-$C_2$haloalkyl, and $C_1$-$C_2$haloalkoxy.

$R_2$ is 0 or 1 or more substituents independently chosen from (iv) and (v):

(iv) is halogen, hydroxyl, cyano, azido, nitro, amino, —$CONH_2$, $C_1$-$C_6$haloalkyl, and $C_1$-$C_6$haloalkoxy.

(v) is $C_1$-$C_8$alkyl, $C_2$-$C_8$alkenyl, $C_2$-$C_8$alkynyl, —$OR_{11}$, —$(CH_2)_{0-4}C(O)R_{11}$, —$(CH_2)_{0-4}C(S)R_{11}$, —$(CH_2)_{0-4}NR_{11}R_{12}$, —$(CH_2)_{0-4}C(O)OR_{11}$, —$(CH_2)_{0-4}OC(O)R_{11}$, —$(CH_2)_{0-4}C(S)SR_{11}$, —$(CH_2)_{0-4}SC(S)R_{11}$, —$(CH_2)_{0-4}OC(O)NR_{11}R_{12}$, —$(CH_2)_{0-4}N(R_{11})C(O)OR_{12}$, —$(CH_2)_{0-4}N(R_{11})C(O)NR_{12}R_{13}$, —$(CH_2)_{0-4}N(R_{11})OC(O)R_{12}$, —$(CH_2)_{0-4}C(O)SR_{11}$, —$(CH_2)_{0-4}S(O)_aR_{11}$, —$(CH_2)_{0-4}N(R_{11})NR_{12}R_{13}$, —$(CH_2)_{0-4}S(O)_bNR_{11}R_{12}$, —$(CH_2)_{0-4}N(R_{11})S(O)_bR_{12}$, —$(CH_2)_{0-4}S(O)_2ONR_{11}$, —$(CH_2)_{0-4}OS(O)_2NR_{11}$, —$N(R_{11})C(S)R_{12}$, —$C(S)NR_{11}$, —$C(S)SR_{11}$, —$(CH_2)_{0-4}N(R_{11})C(S)NR_{12}R_{13}$, —$(CH_2)_{0-4}S(O)_2OR_{11}$, —$(CH_2)_{0-4}OS(O)R_{11}$, —$(CH_2)_{0-4}NR_{11}C(O)R_{12}$, —$(CH_2)_{0-4}C(O)NR_{11}R_{12}$, —$(CH_2)_{0-4}NR_{11}C(O)R_{12}$, —NHC(O)($C_1$-$C_6$haloalkyl), —$(CH_2)_{0-4}$(carbocycle), —$O(CH_2)_{0-4}$(carbocycle), —$S(O)_m(CH_2)_{0-4}$(carbocycle), —$(CH_2)_{0-4}$(heterocycle), —$O(CH_2)_{0-4}$(heterocycle), and —$S(O)_m(CH_2)_{0-4}$(heterocycle). Each of (v) is optionally substituted with one or more substituents independently chosen from: halogen, hydroxyl, vinyl, allenyl, oxo, cyano, amino, —COOH, $C_1$-$C_6$alkyl, $C_1$-$C_6$alkoxy, (mono- and di-$C_1$-$C_6$alkylamino)$C_0$-$C_2$alkyl, $C_1$-$C_6$alkylester, $C_1$-$C_6$alkylthio, $C_1$-$C_2$haloalkyl, and $C_1$-$C_2$haloalkoxy.

$Y_1$ is $NR_3$, O, or S.

$Y_2$ is N or $CR_4$.

$R_3$ is hydrogen or $C_1$-$C_8$alkyl optionally substituted with one or more substituents independently chosen from halogen, hydroxyl, vinyl, allenyl, oxo, cyano, amino, —COOH, $C_1$-$C_6$alkoxy, (mono- and di-$C_1$-$C_6$alkylamino)$C_0$-$C_2$alkyl, $C_1$-$C_6$alkylester, $C_1$-$C_6$alkylthio, $C_1$-$C_2$haloalkyl, and $C_1$-$C_2$haloalkoxy.

$R_4$ is hydrogen, halogen, hydroxyl, amino, $C_1$-$C_2$haloalkyl, or $C_1$-$C_2$haloalkoxy, or $R_4$ is $C_1$-$C_8$alkyl, $C_1$-$C_8$alkoxy, $C_2$-$C_8$alkanoyl, $C_1$-$C_8$alkylester, (mono- or di-$C_1$-$C_8$alkylamino)$C_0$-$C_2$alkyl, mono- or di-$C_1$-$C_8$alkylcarbamate, (carbocycle)$C_0$-$C_4$alkyl, or (heterocycle)$C_0$-$C_4$alkyl, each of which is optionally substituted with one or more substituents independently chosen from halogen, hydroxyl, vinyl, allenyl, oxo, cyano, amino, —COOH, $C_1$-$C_6$alkyl, $C_1$-$C_6$alkoxy, (mono- and di-$C_1$-$C_6$alkylamino)$C_0$-$C_2$alkyl, $C_1$-$C_6$alkylester, $C_1$-$C_6$alkylthio, $C_1$-$C_2$haloalkyl, and $C_1$-$C_2$haloalkoxy.

Z is O, S, S(O), S(O)$_2$, N($R_5$), C(O)NH, or C($R_6$)($R_6'$).

$R_5$ is hydrogen or $R_5$ is $C_1$-$C_8$alkyl optionally substituted with one or more substituents independently chosen from halogen, hydroxyl, vinyl, allenyl, oxo, cyano, amino, —COOH, $C_1$-$C_6$alkoxy, (mono- and di-$C_1$-$C_6$alkylamino)$C_0$-$C_2$alkyl, $C_1$-$C_6$alkylester, $C_1$-$C_6$alkylthio, $C_1$-$C_2$haloalkyl, and $C_1$-$C_2$haloalkoxy.

$R_6$ is hydrogen, halogen, hydroxyl, amino, $C_1$-$C_2$haloalkyl, or $C_1$-$C_2$haloalkoxy, or $R_6$ is $C_1$-$C_8$alkyl, $C_1$-$C_8$alkoxy, $C_2$-$C_8$alkanoyl, $C_1$-$C_8$alkylester, (mono- or di-$C_1$-$C_8$alkylamino)$C_0$-$C_2$alkyl, mono- or di-$C_1$-$C_8$alkylcarbamate, (carbocycle)$C_0$-$C_4$alkyl, or (heterocycle)$C_0$-$C_4$alkyl, each of which is optionally substituted with one or more substituents independently chosen from halogen, hydroxyl, vinyl, allenyl, oxo, cyano, amino, —COOH, $C_1$-$C_6$alkoxy, (mono- and di-$C_1$-$C_6$alkylamino)$C_0$-$C_2$alkyl, $C_1$-$C_6$alkylester, $C_1$-$C_6$alkylthio, $C_1$-$C_2$haloalkyl, and $C_1$-$C_2$haloalkoxy.

$R_6'$ is hydrogen, halogen, hydroxyl, amino, $C_1$-$C_4$alkyl, or $C_1$-$C_4$ alkoxy.

n is 1, 2, 3, or 4.

$R_7$ and $R_8$ are independently chosen at each occurrence.

$R_7$ is hydrogen, halogen, hydroxyl, amino, $C_1$-$C_2$haloalkyl, or $C_1$-$C_2$haloalkoxy, or $R_7$ is $C_1$-$C_8$alkyl, $C_1$-$C_8$alkoxy, $C_2$-$C_8$alkanoyl, $C_1$-$C_8$alkylester, (mono- or di-$C_1$-$C_8$alkylamino)$C_0$-$C_2$alkyl, mono- or di-$C_1$-$C_8$alkylcarbamate, (carbocycle)$C_0$-$C_4$alkyl, or (heterocycle)$C_0$-$C_4$alkyl, each of which is optionally substituted with one or more substituents independently chosen from halogen, hydroxyl, vinyl, allenyl, oxo, cyano, amino, mercapto, —C(O)NH$_2$, —COOH, —NHC(NH)NH$_2$, $C_1$-$C_6$alkyl, $C_1$-$C_6$alkoxy, (mono- and di-$C_1$-$C_6$alkylamino)$C_0$-$C_2$alkyl, $C_1$-$C_6$alkylester, $C_1$-$C_6$alkylthio, $C_1$-$C_2$haloalkyl, and $C_1$-$C_2$haloalkoxy.

$R_8$ is hydrogen, halogen, $C_1$-$C_4$alkyl, or $C_1$-$C_4$alkoxy.

$R_7$ and $R_8$ covalently bound to the same carbon atom may be taken together to form a 3- to 6-membered cycloalkyl or heterocycloalkyl ring;

Q is

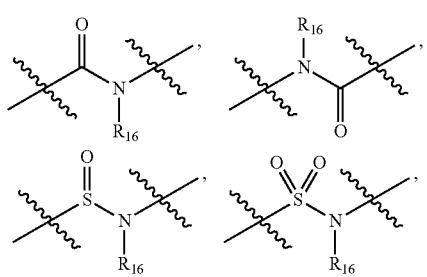

when Z is NR$_5$, and n is 1, Q is

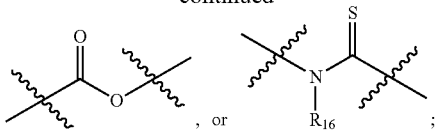

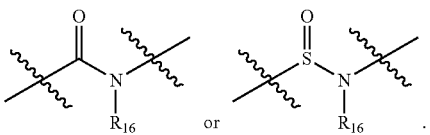

$R_{16}$ is hydrogen or $C_1$-$C_6$alkyl.

$X_5$ is CH or N; $X_6$ is CH or N; $X_7$ is CH or N; $X_8$ is CH or N; and $X_9$ is CH or N. Not more than 3 of $X_5$, $X_6$, $X_7$, $X_8$, and $X_9$ are N; and not more than 2 adjacent $X_5$, $X_6$, $X_7$, $X_8$, and $X_9$ are N.

$R_9$ is 0 to 5 substituents independently chosen from (vi) and (vii):

(vi) halogen, hydroxyl, cyano, azido, nitro, amino, $C_1$-$C_6$haloalkyl, and $C_1$-$C_6$haloalkoxy.

(vii) $C_1$-$C_8$alkyl, $C_2$-$C_8$alkenyl, $C_2$-$C_8$alkynyl, —OR$_{11}$, —(CH$_2$)$_{0-4}$C(O)R$_{11}$, —(CH$_2$)$_{0-4}$C(S)R$_{11}$, —(CH$_2$)$_{0-4}$NR$_{11}$R$_{12}$, —(CH$_2$)$_{0-4}$C(O)OR$_{11}$, —(CH$_2$)$_{0-4}$OC(O)R$_{11}$, —(CH$_2$)$_{0-4}$C(S)SR$_{11}$, —(CH$_2$)$_{0-4}$SC(S)R$_{11}$, —(CH$_2$)$_{0-4}$OC(O)NR$_{11}$R$_{12}$, —(CH$_2$)$_{0-4}$N(R$_{11}$)C(O)OR$_{12}$, —(CH$_2$)$_{0-4}$N(R$_{11}$)C(O)NR$_{12}$R$_{13}$, —(CH$_2$)$_{0-4}$N(R$_{11}$)OC(O)R$_{12}$, —(CH$_2$)$_{0-4}$C(O)SR$_{11}$, —(CH$_2$)$_{0-4}$S(O)$_a$R$_{11}$, —(CH$_2$)$_{0-4}$N(R$_{11}$)NR$_{12}$R$_{13}$, —(CH$_2$)$_{0-4}$S(O)$_b$NR$_{11}$R$_{12}$, —(CH$_2$)$_{0-4}$N(R$_{11}$)S(O)$_b$R$_{12}$, —(CH$_2$)$_{0-4}$S(O)$_2$ONR$_{11}$, —(CH$_2$)$_{0-4}$OS(O)$_2$NR$_{11}$, —N(R$_{11}$)C(S)R$_{12}$, —C(S)NR$_{11}$, —C(S)SR$_{11}$, —(CH$_2$)$_{0-4}$N(R$_{11}$)C(S)NR$_{12}$R$_{13}$, —(CH$_2$)$_{0-4}$S(O)$_2$OR$_{11}$, —(CH$_2$)$_{0-4}$OS(O)R$_{11}$, —(CH$_2$)$_{0-4}$N(R$_{11}$)C(O)(R$_{12}$), —(CH$_2$)$_{0-4}$C(O)NR$_{11}$R$_{12}$, —(CH$_2$)$_{0-4}$(carbocycle), —O(CH$_2$)$_{0-4}$(carbocycle), —S(O)$_m$(CH$_2$)$_{0-4}$(carbocycle), —(CH$_2$)$_{0-4}$(heterocycle), —O(CH$_2$)$_{0-4}$(heterocycle), and —S(O)$_4$CH$_2$)$_{0-4}$(heterocycle).

Each of (vii) is optionally substituted with one or more substituents independently chosen from: halogen, hydroxyl, vinyl, allenyl, oxo, cyano, amino, —COOH, $C_1$-$C_6$alkyl, $C_1$-$C_6$alkoxy, (mono- and di-$C_1$-$C_6$alkylamino)$C_0$-$C_2$alkyl, $C_1$-$C_6$alkylester, $C_1$-$C_6$alkylthio, $C_1$-$C_2$haloalkyl, and $C_1$-$C_2$haloalkoxy; and any two $R_9$ bound to adjacent ring carbon atoms may be joined to form a 5- to 7-membered carbocyclic or heterocyclic ring, which 5- to 7-membered carbocyclic or heterocyclic ring is optionally substituted with one or more substituents independently chosen from (vii).

Alternatively in a first embodiment $R_1$ carries the following definition:

$R_1$ is one substituent chosen from (i), (ii), and (iii)

(i) halogen, hydroxyl, azido, amino, —CONH$_2$, $C_1$-$C_6$haloalkyl, and $C_1$-$C_6$haloalkoxy; and (ii) $C_2$-$C_8$alkenyl, $C_2$-$C_8$alkynyl, —(CH$_2$)$_{2-4}$C(O)R$_{11}$, —(CH$_2$)$_{1-4}$C(S)R$_{11}$, —(CH$_2$)$_{1-4}$NR$_{11}$R$_{12}$, —(CH$_2$)$_{0-4}$C(O)OR$_{11}$, —(CH$_2$)$_{0-4}$OC(O)R$_{11}$, —(CH$_2$)$_{0-4}$C(S)SR$_{11}$, —(CH$_2$)$_{0-4}$SC(S)R$_{11}$, —(CH$_2$)$_{0-4}$OC(O)NR$_{11}$R$_{12}$, —(CH$_2$)$_{0-4}$N(R$_{11}$)C(O)OR$_{12}$, —(CH$_2$)$_{0-4}$N(R$_{11}$)C(O)NR$_{12}$R$_{13}$, —(CH$_2$)$_{0-4}$N(R$_{11}$)OC(O)R$_{12}$, —(CH$_2$)$_{0-4}$C(O)SR$_{11}$, —(CH$_2$)$_{1-4}$SR$_{11}$, —(CH$_2$)$_{0-4}$S(O)R$_{11}$, —(CH$_2$)$_{1-4}$S(O)$_2$R$_{11}$, —(CH$_2$)$_{0-4}$N(R$_{11}$)NR$_{12}$R$_{13}$, —(CH$_2$)$_{0-4}$S(O)$_b$NR$_{11}$R$_{12}$, —(CH$_2$)$_{0-4}$N(R$_{11}$)S(O)$_b$R$_{12}$, —(CH$_2$)$_{0-4}$S $(O)_2ONR_{11}$, —$(CH_2)_{0-4}OS(O)_2NR_{11}$, —$N(R_{11})C(S)R_{12}$, —$C(S)NR_{11}$, —$C(S)SR_{11}$, —$(CH_2)_{0-4}N(R_{11})C(S)NR_{12}R_{13}$, —$(CH_2)_{0-4}S(O)_2OR_{11}$, —$(CH_2)_{0-4}OS(O)R_{11}$, —$(CH_2)_{0-4}N(C_1-C_8alkyl)C(O)(C_1-C_8alkyl)$, —$(CH_2)_{0-4}C(O)NR_{11}R_{12}$, —$(CH_2)_{0-4}$(carbocycle), —$O(CH_2)_{0-4}$(carbocycle), $S(O)_mCH_{2\ 0-4}$(carbocycle), —$(CH_2)_{0-4}$(heterocycle), —$O(CH_2)_{0-4}$(heterocycle), and —$S(O)_m(CH_2)_{0-4}$(heterocycle), where b is independently chosen from 1 and 2; and m is independently chosen from 0, 1, and 2.

In a second, third, fourth, and sixth embodiment the disclosure includes compounds and pharmaceutically acceptable salts of Formula (II).

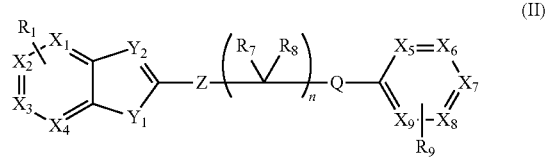

(II)

In Formula (II) each of $X_1$, $X_2$, $X_3$ and $X_4$ is independently selected from CH and N; and the variables $Y_1$, $Y_2$, Z, $R_3$ to $R_9$, $Y_1$, $Y_2$, Z, Q, n, and $X_5$ to $X_9$ carry the definitions set forth above for Formula (I). Unlike Formula (I), Formula (II) does not contain $R_2$ and the variable $R_1$ is defined as follows:

$R_1$ is 0 or 1 or more substituents independently chosen from (i) and (ii):

(i) is halogen, hydroxyl, cyano, azido, nitro, amino, $C_1-C_6$haloalkyl, and $C_1-C_6$haloalkoxy.

(ii) is $C_1-C_8$alkyl, $C_2-C_8$alkenyl, $C_2-C_8$alkynyl, —$OR_{11}$, —$(CH_2)_{0-4}C(O)R_{11}$, —$(CH_2)_{0-4}C(S)R_{11}$, —$(CH_2)_{0-4}NR_{11}R_{12}$, —$(CH_2)_{0-4}C(O)OR_{11}$, —$(CH_2)_{0-4}OC(O)R_{11}$, —$(CH_2)_{0-4}C(S)SR_{11}$, —$(CH_2)_{0-4}SC(S)R_{11}$, —$(CH_2)_{0-4}OC(O)NR_{11}R_{12}$, —$(CH_2)_{0-4}N(R_{11})C(O)OR_{12}$, —$(CH_2)_{0-4}N(R_{11})C(O)NR_{12}R_{13}$, —$(CH_2)_{0-4}N(R_{11})OC(O)OR_{12}$, —$(CH_2)_{0-4}C(O)SR_{11}$, —$(CH_2)_{0-4}S(O)_aR_{11}$, —$(CH_2)_{0-4}N(R_{11})NR_{12}R_{13}$, —$(CH_2)_{0-4}S(O)_bNR_{11}R_{12}$, —$(CH_2)_{0-4}N(R_{11})S(O)_bR_{12}$, —$(CH_2)_{0-4}S(O)_2ONR_{11}$, —$(CH_2)_{0-4}OS(O)_2NR_{11}$, —$N(R_{11})C(S)R_{12}$, —$C(S)NR_{11}$, —$C(S)SR_{11}$, —$(CH_2)_{0-4}N(R_{11})C(S)NR_{12}R_{13}$, —$(CH_2)_{0-4}S(O)_2OR_{11}$, —$(CH_2)_{0-4}OS(O)R_{11}$, —$(CH_2)_{0-4}C(O)NR_{11}R_{12}$, —$(CH_2)_{0-4}N(R_{11})C(O)R_{12}$, —$(CH_2)_{0-4}$(carbocycle), —$O(CH_2)_{0-4}$(carbocycle), —$S(O)_m(CH_2)_{0-4}$(carbocycle), —$(CH_2)_{0-4}$(heterocycle), —$O(CH_2)_{0-4}$(heterocycle), and —$S(O)_m(CH_2)_{0-4}$(heterocycle).

In (ii), a is independently chosen from 0, 1, and 2, b is independently chosen from 1 and 2, and m is independently chosen from 0, 1, and 2. $R_{11}$, $R_{12}$, and $R_{13}$ are independently chosen at each occurrence from hydrogen and $C_1-C_8$aliphatic group. In this embodiment each of (ii) is optionally substituted with one or more substituents independently chosen from: halogen, hydroxyl, vinyl, allenyl, oxo, cyano, amino, —COOH, $C_1-C_6$alkoxy, (mono- and di-$C_1-C_6$alkylamino)$C_0-C_2$alkyl, $C_1-C_6$alkylester, $C_1-C_6$alkylthio, $C_1-C_2$haloalkyl, and $C_1-C_2$haloalkoxy.

In the second embodiment the 6-membered aryl or heteroaryl group in Formula (II) is a heteroaryl group containing at least one nitrogen atom (i.e., at least one of $X_1$, $X_2$, $X_3$ and $X_4$ is N).

In the third embodiment, all variables carry the definitions set forth above for Formula (II), but there is no requirement that at least one of $X_1$, $X_2$, $X_3$ and $X_4$ is N. However in this third embodiment, when $Y_2$ is N; either: (a) $Y_1$ is $NR_3$ (where $R_3$ is not hydrogen) or S; or (b) Z is O, S(O), $S(O)_2$, $N(R_5)$, or $C(R_6)(R_6')$.

In the fourth embodiment either (a) n is 1 and $R_7$ is other than hydrogen; or (b) n is 2, 3, or 4. In this fourth embodiment all variables carry the definitions set forth above for Formula (II).

In the fifth embodiment (Formula III) at least one of $X_5$, $X_6$, $X_7$, $X_8$, or $X_9$ is N. Otherwise all variables carry the definitions set forth above for Formula (II).

The disclosure includes a fifth embodiment directed to compounds and pharmaceutically acceptable salts of Formula (III) in which Q in Formula (II) is replaced by a —NHC(O)— "reverse amide" group. In this embodiment when n is 1; Z is S, S(O), $S(O)_2$, or $C(R_6)(R_6')$. Otherwise, all variables in Formula (III) carry the definitions set forth above for Formula (II).

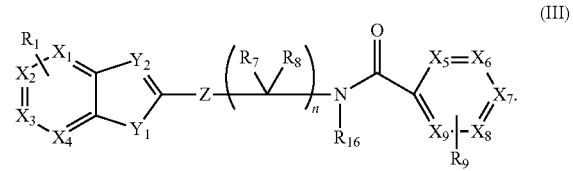

(III)

The disclosure includes a sixth embodiment directed to compounds and pharmaceutically acceptable salts of Formula (II) in which at least one of $X_5$, $X_6$, $X_7$, $X_8$, and $X_9$ is a nitrogen atom. Otherwise, all variables carry the definitions set forth above for Formula (II).

This disclosure includes a seventh embodiment directed to compounds and pharmaceutically acceptable salts of Formula (IV). The phenyl ring in Formula (IV) is substituted with at least one substituent that is not halogen, $C_1-C_6$alkyl, $C_1-C_6$alkoxy, aryloxy, $C_1-C_6$haloalkyl, cyano, nitro, or alkylthio, or in which any two $R_{10}$ bound to adjacent carbon atoms may be joined to form a carbocyclic ring.

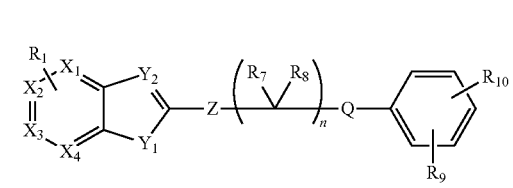

(IV)

In Formula (IV) all variables except $R_9$ and $R_{10}$ carry the definitions set forth above for Formula (II). $R_9$ and $R_{10}$ are defined as follows:

$R_9$ is 0 or 1 or more substituents independently chosen from (vi) and (vii):

(vi) is halogen, hydroxyl, cyano, azido, nitro, amino, $C_1-C_6$haloalkyl, and $C_1-C_6$haloalkoxy.

(vii) is $C_1-C_8$alkyl, $C_2-C_8$alkenyl, $C_2-C_8$alkynyl, —$OR_{11}$, —$(CH_2)_{0-4}C(O)R_{11}$, —$(CH_2)_{0-4}C(S)R_{11}$, —$(CH_2)_{0-4}NR_{11}R_{12}$, —$(CH_2)_{0-4}C(O)OR_{11}$, —$(CH_2)_{0-4}OC(O)R_{11}$, —$(CH_2)_{0-4}C(S)SR_{11}$, —$(CH_2)_{0-4}SC(S)R_{11}$, —$(CH_2)_{0-4}OC(O)NR_{11}R_{12}$, —$(CH_2)_{0-4}N(R_{11})C(O)OR_{12}$, —$(CH_2)_{0-4}N(R_{11})C(O)NR_{12}R_{13}$, —$(CH_2)_{0-4}N(R_{11})OC(O)R_{12}$, —$(CH_2)_{0-4}C(O)SR_{11}$, —$(CH_2)_{0-4}S(O)_aR_{11}$, —$(CH_2)_{0-4}N(R_{11})NR_{12}R_{13}$, —$(CH_2)_{0-4}S(O)_bNR_{11}R_{12}$, —$(CH_2)_{0-4}N(R_{11})S(O)_bR_{12}$, —$(CH_2)_{0-4}S(O)_2ONR_{11}$, —$(CH_2)_{0-4}OS(O)_2NR_{11}$, —$N(R_{11})C(S)R_{12}$, —$C(S)NR_{11}$, —$C(S)SR_{11}$, —(CH$_2$)$_{0-4}$N(R$_{11}$)C(S)NR$_{12}$R$_{13}$, —(CH$_2$)$_{0-4}$S(O)$_2$OR$_{11}$, —(CH$_2$)$_{0-4}$OS(O)R$_{11}$, —(CH$_2$)$_{0-4}$N(R$_{11}$)C(O)(R$_{12}$), —(CH$_2$)$_{0-4}$C(O)NR$_{11}$R$_{12}$, —(CH$_2$)$_{0-4}$(carbocycle), —O(CH$_2$)$_{0-4}$(carbocycle), —S(O)$_m$(CH$_2$)$_{0-4}$(carbocycle), —(CH$_2$)$_{0-4}$(heterocycle), —O(CH$_2$)$_{0-4}$(heterocycle), and —S(O)$_m$(CH$_2$)$_{0-4}$(heterocycle).

Each of (vii) is optionally substituted with one or more substituents independently chosen from: halogen, hydroxyl, vinyl, allenyl, oxo, cyano, amino, —COOH, C$_1$-C$_6$alkyl, C$_1$-C$_6$alkoxy, (mono- and di-C$_1$-C$_6$alkylamino)C$_0$-C$_2$alkyl, C$_1$-C$_6$alkylester, C$_1$-C$_6$alkylthio, C$_1$-C$_2$haloalkyl, and C$_1$-C$_2$haloalkoxy.

R$_{10}$ is at least 1 substituent chosen from (viii), (ix), and (x):

(viii) is hydroxyl, azido, amino, and C$_1$-C$_2$haloalkoxy.

(ix) is C$_2$-C$_8$alkenyl, C$_2$-C$_8$alkynyl, —(CH$_2$)$_{0-4}$R$_{11}$, —(CH$_2$)$_{0-4}$C(S)R$_{11}$, —(CH$_2$)$_{0-4}$C(O)OR$_{11}$, —(CH$_2$)$_{0-4}$OC(O)R$_{11}$, —(CH$_2$)$_{0-4}$C(S)SR$_{11}$, —(CH$_2$)$_{0-4}$SC(S)R$_{11}$, —(CH$_2$)$_{0-4}$OC(O)NR$_{11}$R$_{12}$, —(CH$_2$)$_{0-4}$N(R$_{11}$)C(O)OR$_{12}$, —(CH$_2$)$_{0-4}$N(R$_{11}$)C(O)NR$_{12}$R$_{13}$, —(CH$_2$)$_{0-4}$N(R$_{11}$)OC(O)R$_{12}$, —(CH$_2$)$_{0-4}$C(O)SR$_{11}$, —(CH$_2$)$_{0-4}$S(O)$_b$R$_{11}$, —(CH$_2$)$_{0-4}$N(R$_{11}$)NR$_{12}$R$_{13}$, —(CH$_2$)$_{0-4}$S(O)$_b$NR$_{11}$R$_{12}$, —(CH$_2$)$_{0-4}$N(R$_{11}$)S(O)$_b$R$_{12}$, —(CH$_2$)$_{0-4}$S(O)$_2$ONR$_{11}$, —(CH$_2$)$_{0-4}$OS(O)$_2$NR$_{11}$, —N(R$_{11}$)C(S)R$_{12}$, —C(S)NR$_{11}$, —C(S)SR$_{11}$, —(CH$_2$)$_{0-4}$N(R$_{11}$)C(S)NR$_{12}$R$_{13}$, —(CH$_2$)$_{0-4}$S(O)$_2$OR$_{11}$, —(CH$_2$)$_{0-4}$OS(O)R$_{11}$, —(CH$_2$)$_{0-4}$C(O)NR$_{11}$R$_{12}$, —(CH$_2$)$_{0-4}$NR$_{11}$C(O)R$_{12}$, —(CH$_2$)$_{0-4}$(carbocycle), —S(O)$_m$(CH$_2$)$_{0-4}$(carbocycle), —(CH$_2$)$_{0-4}$(heterocycle), —O(CH$_2$)$_{0-4}$(heterocycle), and —S(O)$_m$(CH$_2$)$_{0-4}$(heterocycle).

In an embodiment (ix) has the following definition (ix) C$_2$-C$_8$alkenyl, C$_2$-C$_8$alkynyl, —(CH$_2$)$_{0-4}$C(O)R$_{11}$, —(CH$_2$)$_{0-4}$C(S)R$_{11}$, —(CH$_2$)$_{0-4}$NR$_{11}$R$_{12}$, —(CH$_2$)$_{0-4}$C(O)OR$_{11}$, —(CH$_2$)$_{0-4}$OC(O)R$_{11}$, —(CH$_2$)$_{0-4}$C(S)SR$_{11}$, —(CH$_2$)$_{0-4}$SC(S)R$_{11}$, —(CH$_2$)$_{0-4}$OC(O)NR$_{11}$R$_{12}$, —(CH$_2$)$_{0-4}$N(R$_{11}$)C(O)OR$_{12}$, —(CH$_2$)$_{0-4}$N(R$_{11}$)C(O)NR$_{12}$R$_{13}$, —(CH$_2$)$_{0-4}$N(R$_{11}$)OC(O)R$_{12}$, —(CH$_2$)$_{0-4}$C(O)SR$_{11}$, —(CH$_2$)$_{0-4}$S(O)$_b$R$_{11}$, —(CH$_2$)$_{0-4}$N(R$_{11}$)NR$_{12}$R$_{13}$, —(CH$_2$)$_{0-4}$S(O)$_b$NR$_{11}$R$_{12}$, —(CH$_2$)$_{0-4}$N(R$_{11}$)S(O)$_b$R$_{12}$, —(CH$_2$)$_{0-4}$S(O)$_2$ONR$_{11}$, —(CH$_2$)$_{0-4}$OS(O)$_2$NR$_{11}$, —N(R$_{11}$)C(S)R$_{12}$, —C(S)NR$_{11}$, —C(S)SR$_{11}$, —(CH$_2$)$_{0-4}$N(R$_{11}$)C(S)NR$_{12}$R$_{13}$, —(CH$_2$)$_{0-4}$S(O)$_2$OR$_{11}$, —(CH$_2$)$_{0-4}$OS(O)R$_{11}$, —(CH$_2$)$_{0-4}$C(O)NR$_{11}$R$_{12}$, —(CH$_2$)$_{0-4}$NR$_{11}$C(O)R$_{12}$, —S(O)$_m$(CH$_2$)$_{0-4}$(carbocycle), and —S(O)$_m$(CH$_2$)$_{0-4}$(heterocycle) each of (ix) is optionally substituted with one or more substituents independently chosen from: halogen, hydroxyl, vinyl, allenyl, oxo, cyano, amino, —COOH, C$_1$-C$_6$alkyl, C$_1$-C$_6$alkoxy, (mono- and di-C$_1$-C$_6$alkylamino)C$_0$-C$_2$alkyl, C$_1$-C$_6$alkylester, C$_1$-C$_6$alkylthio, C$_1$-C$_2$haloalkyl, and C$_1$-C$_2$haloalkoxy;

Each of (ix) is optionally substituted with one or more substituents independently chosen from: halogen, hydroxyl, vinyl, allenyl, oxo, cyano, amino, —COOH, C$_1$-C$_6$alkyl, C$_1$-C$_6$alkoxy, (mono- and di-C$_1$-C$_6$alkylamino)C$_0$-C$_2$alkyl, C$_1$-C$_6$alkylester, C$_1$-C$_6$alkylthio, C$_1$-C$_2$haloalkyl, and C$_1$-C$_2$haloalkoxy.

(x) is C$_1$-C$_8$alkyl and C$_1$-C$_8$alkoxy, each of which is substituted with one or more substituents independently chosen from halogen, hydroxyl, vinyl, allenyl, —COOH, oxo, cyano, amino, C$_1$-C$_6$alkoxy, (mono- and di-C$_1$-C$_6$alkylamino)C$_0$-C$_2$alkyl, C$_1$-C$_6$alkylester, C$_1$-C$_6$alkylthio, C$_1$-C$_2$haloalkyl, and C$_1$-C$_2$haloalkoxy.

In addition, any two R$_{10}$ bound to adjacent ring carbon atoms may be joined to one another to form a 5- to 7-membered carbocyclic ring that is optionally substituted with one or more substituents independently chosen from (vi) and (vii).

The disclosure includes an eighth embodiment directed to compounds and pharmaceutically acceptable salts of Formula (V).

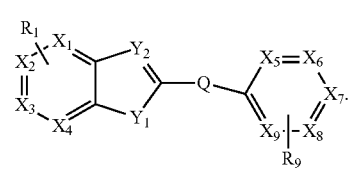

Within Formula (V) all variables carry the definitions set forth above in the description of Formula (II).

The disclosure also includes pharmaceutical compositions and solid dosage forms containing a compound of any one of Formulae (I), (II), (III), (IV), or (V) together with a pharmaceutically acceptable carrier.

The disclosure further includes a method of treating a bacterial infection in a patient, comprising administering a therapeutically effective amount of a compound or salt of any one of Formulae (I) to (V) to a patient in need of such treatment. The compound of Formulae (I) to (V) may be administered as the only active agent or may be administered together with one or more additional active agents.

DETAILED DESCRIPTION

Chemical Description and Terminology

Compounds are described using standard nomenclature. Unless defined otherwise, all technical and scientific terms used herein have the same meaning as is commonly understood by one of skill in the art to which this invention belongs. Unless clearly contraindicated by the context each compound name includes the free acid or free base form of the compound as well as all pharmaceutically acceptable salts of the compound.

The term "Formula (I)" encompasses all compounds that satisfy Formula (I), including any enantiomers, racemates and stereoisomers, as well as all pharmaceutically acceptable salts of such compounds. "Formula (I)" includes all subgeneric groups of Formula (I) unless clearly contraindicated by the context in which this phrase is used.

The terms "a" and "an" do not denote a limitation of quantity, but rather denote the presence of at least one of the referenced item. The term "or" means "and/or". The open-ended transitional phrase "comprising" encompasses the intermediate transitional phrase "consisting essentially of" and the close-ended phrase "consisting of." Claims reciting one of these three transitional phrases, or with an alternate transitional phrase such as "containing" or "including" can be written with any other transitional phrase unless clearly precluded by the context or art. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein. Unless defined otherwise, technical and scientific terms used herein have the same meaning as is commonly understood by one of skill in the art to which this invention belongs.

Compounds of Formula (I) include all compounds of Formula (I) having isotopic substitutions at any position. Isotopes include those atoms having the same atomic number but different mass numbers. By way of general example, and without limitation, isotopes of hydrogen include tritium and deuterium and isotopes of carbon include $^{11}C$, $^{13}C$, and $^{14}C$.

An "active agent" means a compound (including a compound disclosed herein), element, or mixture that when administered to a patient, alone or in combination with another compound, element, or mixture, confers, directly or indirectly, a physiological effect on the patient. The indirect physiological effect may occur via a metabolite or other indirect mechanism.

A dash ("-") that is not between two letters or symbols is used to indicate a point of attachment for a substituent. For example, —(C═O)NH$_2$ is attached through carbon of the keto (C═O) group.

An "aliphatic group" is a hydrocarbon group having the indicated number of carbon atoms in which the carbon atoms are covalently bound in single, double or triple covalent bonds in straight chains, branched chains, or non-aromatic rings. Aliphatic groups may be substituted.

"Alkyl" is a branched or straight chain saturated aliphatic hydrocarbon group, having the specified number of carbon atoms, generally from 1 to about 8 carbon atoms. The term $C_1$-$C_6$alkyl as used herein indicates an alkyl group having from 1, 2, 3, 4, 5, or 6 carbon atoms. Other embodiments include alkyl groups having from 1 to 6 carbon atoms, 1 to 4 carbon atoms or 1 or 2 carbon atoms, e.g. $C_1$-$C_8$alkyl, $C_1$-$C_4$alkyl, and $C_1$-$C_2$alkyl. When $C_0$-$C_n$ alkyl is used herein in conjunction with another group, for example, ($C_3$-$C_7$cycloalkyl)$C_0$-$C_4$ alkyl, the indicated group, in this case cycloalkyl, is either directly bound by a single covalent bond ($C_0$alkyl), or attached by an alkyl chain having the specified number of carbon atoms, in this case 1, 2, 3, or 4 carbon atoms. Examples of alkyl include, but are not limited to, methyl, ethyl, n-propyl, isopropyl, n-butyl, 3-methylbutyl, t-butyl, n-pentyl, and sec-pentyl.

"Alkenyl" is a branched or straight chain aliphatic hydrocarbon group having one or more double carbon-carbon bonds that may occur at any stable point along the chain, having the specified number of carbon atoms. Examples of alkenyl include, but are not limited to, ethenyl and propenyl.

"Alkynyl" is a branched or straight chain aliphatic hydrocarbon group having one or more triple carbon-carbon bonds that may occur at any stable point along the chain, having the specified number of carbon atoms. Examples of alkynyl include, but are not limited to, ethynyl and propynyl.

"Alkenyl" is an alkenyl group having two consecutive double bonds, i.e., a group of formula —C═C═CH$_2$.

"Alkoxy" is an alkyl group as defined above with the indicated number of carbon atoms covalently bound to the group it substitutes by an oxygen bridge (—O—). Examples of alkoxy include, but are not limited to, methoxy, ethoxy, n-propoxy, i-propoxy, n-butoxy, 2-butoxy, t-butoxy, n-pentoxy, 2-pentoxy, 3-pentoxy, isopentoxy, neopentoxy, n-hexoxy, 2-hexoxy, 3-hexoxy, and 3-methylpentoxy.

"Alkylthio" indicates an alkyl group as defined above attached through a sulfur linkage, i.e. a group of the formula alkyl-S—. Examples include ethylthio and pentylthio.

"Alkanoyl" is an alkyl group as defined above with the indicated number of carbon atoms covalently bound to the group is substitutes through a carbonyl (C═O) bridge. The carbonyl carbon is included in the number of carbons, that is $C_2$alkanoyl is a $CH_3$(C═O)— group.

"Alkylester" is an alkyl group as defined herein covalently bound to the group it substitutes by an ester linkage. The ester linkage may be in either orientation, e.g., a group of the formula —O(C═O)alkyl or a group of the formula —(C═O)O-alkyl.

"Aryl" indicates aromatic groups containing only carbon in the aromatic ring or rings. Typical aryl groups contain 1 to 3 separate, fused, or pendant rings and from 6 to about 18 ring atoms, without heteroatoms as ring members. When indicated, such aryl groups may be further substituted with carbon or non-carbon atoms or groups. Such substitution may include fusion to a 5 to 7-membered saturated cyclic group that optionally contains 1 or 2 heteroatoms independently chosen from N, O, and S, to form, for example, a 3,4-methylenedioxy-phenyl group. Aryl groups include, for example, phenyl, naphthyl, including 1-naphthyl, 2-naphthyl, and bi-phenyl.

A "carbocyclic group" or a "carbocycle" is a monocyclic or bicyclic saturated, partially unsaturated, or aromatic ring system in which all ring atoms are carbon. Usually each ring of the carbocyclic group contains from 4-6 ring atoms and a bicyclic carbocyclic group contains from 7 to 10 ring atoms but some other number of ring atoms may be specified. Unless otherwise indicated, the carbocyclic group may be attached to the group it substitutes at any carbon atom that results in a stable structure. When indicated the carbocyclic rings described herein may be substituted at any carbon atom if the resulting compound is stable. Examples of carbocycles include phenyl, naphthyl, tetrahydronaphthyl, cyclopropyl, cyclohexyl, and cyclohexenyl.

"Cycloalkyl" is a saturated hydrocarbon ring group, having the specified number of carbon atoms. Monocyclic cycloalkyl groups typically have from 3 to about 8 carbon ring atoms or from 3 to 7 (3, 4, 5, 6, or 7) carbon ring atoms. Cycloalkyl substituents may be pendant from a substituted nitrogen, oxygen, or carbon atom, or a substituted carbon atom that may have two substituents may have a cycloalkyl group, which is attached as a spiro group. Examples of cycloalkyl groups include cyclopropyl, cyclobutyl, cyclopentyl, and cyclohexyl.

"Halo" or "halogen" indicates any of fluoro, chloro, bromo, and iodo.

"Haloalkyl" indicates both branched and straight-chain alkyl groups having the specified number of carbon atoms, substituted with 1 or more halogen atoms, up to the maximum allowable number of halogen atoms. Examples of haloalkyl include, but are not limited to, trifluoromethyl, difluoromethyl, 2-fluoroethyl, and penta-fluoroethyl.

"Haloalkoxy" indicates a haloalkyl group as defined herein attached through an oxygen bridge (oxygen of an alcohol radical).

The term "heterocyclic group" or "heterocycle" indicates a monocyclic saturated, partially unsaturated, or aromatic ring containing from 1 to about 4 heteroatoms chosen from N, O, and S, with remaining ring atoms being carbon, or a bicyclic saturated, partially unsaturated, or aromatic heterocyclic ring system containing at least 1 heteroatom in the two ring system chosen from N, O, and S and containing up to about 4 heteroatoms independently chosen from N, O, and S in each ring of the two ring system. Usually each ring of the heterocyclic group contains from 4-6 ring atoms but some other number of ring atoms may be specified. Unless otherwise indicated, the heterocyclic ring may be attached to its pendant group at any heteroatom or carbon atom that results in a stable structure. When indicated the heterocyclic rings described herein may be substituted on carbon, sulfur, or nitrogen atom if the resulting compound is stable. It is preferred that the total number of heteroatoms in a heterocyclic groups is not more than 4 and that the total number of S and O atoms in a heterocyclic group is not more than 2, more preferably not more than 1. Examples of heterocyclic groups include, pyridyl, indolyl, pyrimidinyl, pyridazinyl, pyrazinyl, imidazolyl, oxazolyl, furanyl, thiophenyl, thiazolyl, triazolyl, tetrazolyl, isoxazolyl, quinolinyl, pyrrolyl, pyrazolyl, benz[b]thiophenyl, isoquinolinyl, quinazolinyl, quinoxalinyl, thienyl, isoindolyl, dihydroisoindolyl, 5,6,7,8-tetrahydroisoquinoline, pyrazolyl, pyrrolidinyl, morpholinyl, piperazinyl, piperidinyl, and pyrrolidinyl. In certain embodiments a heterocyclic group is chosen from pyridinyl, pyrimidinyl, furanyl, thienyl, and pyrrolyl.

Additional examples heterocyclic groups include, but are not limited to, phthalazinyl, indolizinyl, indazolyl, benzothiazolyl, benzimidazolyl, benzofuranyl, benzoisoxolyl, dihydro-benzodioxinyl, oxadiazolyl, thiadiazolyl, triazolyl, tetrazolyl, oxazolopyridinyl, imidazopyridinyl, isothiazolyl, naphthyridinyl, cinnolinyl, carbazolyl, beta-carbolinyl, isochromanyl, chromanonyl, chromanyl, tetrahydroisoquinolinyl, isoindolinyl, isobenzotetrahydrofuranyl, isobenzotetrahydrothienyl, isobenzothienyl, benzoxazolyl, pyridopyridinyl, benzotetrahydrofuranyl, benzotetrahydrothienyl, purinyl, benzodioxolyl, triazinyl, phenoxazinyl, phenothiazinyl, 5 pteridinyl, benzothiazolyl, imidazopyridinyl, imidazothiazolyl, dihydrobenzisoxazinyl, benzisoxazinyl, benzoxazinyl, dihydrobenzisothiazinyl, benzopyranyl, benzothiopyranyl, coumarinyl, isocoumarinyl, chromanyl, tetrahydroquinolinyl, dihydroquinolinyl, dihydroquinolinonyl, dihydroisoquinolinonyl, dihydrocoumarinyl, dihydroisocoumarinyl, isoindolinonyl, benzodioxanyl, benzoxazolinonyl, pyrrolyl N-oxide, pyrimidinyl N-oxide, pyridazinyl N-oxide, pyrazinyl N-oxide, quinolinyl N-oxide, indolyl N-oxide, indolinyl N oxide, isoquinolyl N-oxide, quinazolinyl N-oxide, quinoxalinyl N-oxide, phthalazinyl N-oxide, imidazolyl N-oxide, isoxazolyl N-oxide, oxazolyl N-oxide, thiazolyl N-oxide, indolizinyl N oxide, indazolyl N-oxide, benzothiazolyl N-oxide, benzimidazolyl N-oxide, pyrrolyl N-oxide, oxadiazolyl N-oxide, thiadiazolyl N-oxide, tetrazolyl N-oxide, benzothiopyranyl S-oxide, and benzothiopyranyl S,S-dioxide.

"Heteroaryl" is a stable monocyclic aromatic ring having the indicated number of ring atoms which contains from 1 to 3, or in some embodiments from 1 to 2, heteroatoms chosen from N, O, and S, with remaining ring atoms being carbon, or a stable bicyclic or tricyclic system containing at least one 5- to 7-membered aromatic ring which contains from 1 to 3, or in some embodiments from 1 to 2, heteroatoms chosen from N, O, and S, with remaining ring atoms being carbon. Monocyclic heteroaryl groups typically have from 5 to 7 ring atoms. In some embodiments bicyclic heteroaryl groups are 9- to 10-membered heteroaryl groups, that is, groups containing 9 or 10 ring atoms in which one 5- to 7-member aromatic ring is fused to a second aromatic or non-aromatic ring. When the total number of S and O atoms in the heteroaryl group exceeds 1, these heteroatoms are not adjacent to one another. It is preferred that the total number of S and O atoms in the heteroaryl group is not more than 2. It is particularly preferred that the total number of S and O atoms in the aromatic heterocycle is not more than 1. Examples of heteroaryl groups include, but are not limited to, oxazolyl, pyranyl, pyrazinyl, pyrazolopyrimidinyl, pyrazolyl, pyridazinyl, pyridyl, pyrimidinyl, pyrrolyl, quinolinyl, tetrazolyl, thiazolyl, thienylpyrazolyl, thiophenyl, triazolyl, benzo[d]oxazolyl, benzofuranyl, benzothiazolyl, benzothiophenyl, benzoxadiazolyl, dihydrobenzodioxynyl, furanyl, imidazolyl, indolyl, and isoxazolyl.

"Heterocycloalkyl" is a saturated ring group, having 1, 2, 3, or 4 heteroatoms independently chosen from N, S, and O, with remaining ring atoms being carbon. Monocyclic heterocycloalkyl groups typically have from 3 to about 8 ring atoms or from 4 to 6 ring atoms. Examples of heterocycloalkyl groups include morpholinyl, piperazinyl, piperidinyl, and pyrrolinyl.

The term "mono- and/or di-alkylamino" indicates secondary or tertiary alkyl amino groups, wherein the alkyl groups are independently chosen alkyl groups, as defined herein, having the indicated number of carbon atoms. The point of attachment of the alkylamino group is on the nitrogen. Examples of mono- and di-alkylamino groups include ethylamino, dimethylamino, and methyl-propyl-amino.

"Mono- and/or di-alkylcarbamate" includes mono-alkylcarbamate radical of formula $(alkyl_1)O(C=O)NH-$ or a dialkylcarbamate radical of the formula $(alkyl_1)O(C=O)N(alkyl_2)-$ in which the point of attachment of the mono- or dialkylcarbamate substituent to the molecule it substitutes is on the nitrogen of the carbamate amino. The term "mono and/or di-alkylcarbamate" also includes groups of the formula $(alkyl_1)NH(C=O)O-$ and $(alkyl_1)N(alkyl_2)(C=O)O-$ in which the carbamate is covalently bound to the group it substitutes by its non-keto oxygen atom. The groups $alkyl_1$ and $alkyl_2$ are independently chosen alkyl groups, carrying the alkyl definition set forth in this disclosure and having the indicated number of carbon atoms.

The term "substituted", as used herein, means that any one or more hydrogens on the designated atom or group is replaced with a selection from the indicated group, provided that the designated atom's normal valence is not exceeded. When the substituent is oxo (i.e., $=O$) then 2 hydrogens on the atom are replaced. When an oxo group substitutes aromatic moieties, the corresponding partially unsaturated ring replaces the aromatic ring. For example a pyridyl group substituted by oxo is a pyridone. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation into an effective therapeutic agent. Unless otherwise specified substituents are named into the core structure. For example, it is to be understood that when aminoalkyl is means the point of attachment of this substituent to the core structure is in the alkyl portion and when alkylamino means the point of attachment is a bond to the nitrogen of the amino group.

Suitable groups that may be present on a "substituted" or "optionally substituted" position include, but are not limited to, e.g., halogen; cyano; hydroxyl; nitro; azido; alkanoyl (such as a $C_2$-$C_6$ alkanoyl group); carboxamide; alkyl groups (including cycloalkyl groups) having 1 to about 8 carbon atoms, or 1 to about 6 carbon atoms; alkenyl and alkynyl groups including groups having one or more unsaturated linkages and from 2 to about 8, or 2 to about 6 carbon atoms; alkoxy groups having one or more oxygen linkages and from 1 to about 8, or from 1 to about 6 carbon atoms; aryloxy such as phenoxy; alkylthio groups including those having one or more thioether linkages and from 1 to about 8 carbon atoms, or from 1 to about 6 carbon atoms; alkylsulfinyl groups including those having one or more sulfinyl linkages and from 1 to about 8 carbon atoms, or from 1 to about 6 carbon atoms; alkylsulfonyl groups including those having one or more sulfonyl linkages and from 1 to about 8 carbon atoms, or from 1 to about 6 carbon atoms; aminoalkyl groups including groups having one or more N atoms and from 1 to about 8, or from 1 to about 6 carbon atoms; aryl having 6 or more carbons and one or more rings, (e.g., phenyl, biphenyl, naphthyl, or the like, each ring either substituted or unsubstituted aromatic); arylalkyl having 1 to 3 separate or fused rings and from 6 to about 18 ring carbon atoms, with benzyl being an exemplary arylalkyl group; arylalkoxy having 1 to 3 separate or fused rings and from 6 to about 18 ring carbon atoms, with benzyloxy being an exemplary arylalkoxy group; or a saturated, unsaturated, or aromatic heterocyclic group having 1 to 3 separate or fused rings with 3 to about 8 members per ring and one or more N, O or S atoms, e.g. coumarinyl, quinolinyl, isoquinolinyl, quinazolinyl, pyridyl, pyrazinyl, pyrimidinyl, furanyl, pyrrolyl, thienyl, thiazolyl, triazinyl, oxazolyl, isoxazolyl, imidazolyl, indolyl, benzofuranyl, benzothiazolyl, tetrahydrofuranyl, tetrahydropyranyl, piperidinyl, morpholinyl, piperazinyl, and pyrrolidinyl. Such heterocyclic groups may be further substituted, e.g. with hydroxy, alkyl, alkoxy, halogen and amino. In certain embodiments "optionally substituted" includes one or more substituents independently chosen from halogen, hydroxyl, amino, cyano, —CHO, —COOH, —CONH$_2$, $C_1$-$C_6$alkyl, $C_2$-$C_6$alkenyl, $C_1$-$C_6$alkoxy, $C_2$-$C_6$alkanoyl, $C_1$-$C_6$alkylester, (mono- and di-$C_1$-$C_6$alkylamino)$C_0$-$C_2$alkyl, $C_1$-$C_2$haloalkyl, and $C_1$-$C_2$haloalkoxy.

A "dosage form" means a unit of administration of an active agent. Examples of dosage forms include tablets, capsules, injections, suspensions, liquids, emulsions, creams, ointments, suppositories, inhalable forms, transdermal forms, and the like.

"Pharmaceutical compositions" are compositions comprising at least one active agent, such as a compound or salt of Formula I, and at least one other substance, such as a carrier. Pharmaceutical compositions optional contain one or more additional active agents. When specified, pharmaceutical compositions meet the U.S. FDA's GMP (good manufacturing practice) standards for human or non-human drugs. "Pharmaceutical combinations" are combinations of at least two active agents which may be combined in a single dosage form or provided together in separate dosage forms with instructions that the active agents are to be used together to treat a disorder, such as a Gram-negative bacterial infection.

"Pharmaceutically acceptable salts" includes derivatives of the disclosed compounds in which the parent compound is modified by making inorganic and organic, non-toxic, acid or base addition salts thereof. The salts of the present compounds can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are preferred, where practicable. Salts of the present compounds further include solvates of the compounds and of the compound salts.

Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—$(CH_2)_n$—COOH where n is 0-4, and the like. Lists of additional suitable salts may be found, e.g., in *Remington's Pharmaceutical Sciences,* 17th ed., Mack Publishing Company, Easton, Pa., p. 1418 (1985).

The term "carrier" applied to pharmaceutical compositions/combinations of the invention refers to a diluent, excipient, or vehicle with which an active compound is provided.

A "pharmaceutically acceptable excipient" means an excipient that is useful in preparing a pharmaceutical composition/combination that is generally safe, non-toxic and neither biologically nor otherwise undesirable, and includes an excipient that is acceptable for veterinary use as well as human pharmaceutical use. A "pharmaceutically acceptable excipient" as used in the present application includes both one and more than one such excipient.

A "patient" is a human or non-human animal in need of medical treatment. Medical treatment can include treatment of an existing condition, such as a disease or disorder, prophylactic or preventative treatment, or diagnostic treatment. In some embodiments the patient is a human patient.

"Providing" means giving, administering, selling, distributing, transferring (for profit or not), manufacturing, compounding, or dispensing.

"Treatment," as used herein includes providing a compound of this disclosure such as a compound of any of Formulae (I)-(VIII), either as the only active agent or together with at least one additional active agent sufficient to: (a) inhibiting the disease, i.e. arresting its development; and (b) relieving the disease, i.e., causing regression of the disease and in the case of a bacterial infection to eliminate the infection in the patient. "Treating" and "treatment" also means providing a therapeutically effective amount of a compound of the invention as the only active agent or together with at least one additional active agent to a patient having or susceptible to a bacterial infection. "Prophylactic treatment" includes administering an amount of a compound of the disclosure sufficient to significantly reduce the likelihood of a disease from occurring in a patient who may be predisposed to the disease but who does not have it.

A "therapeutically effective amount" of a pharmaceutical composition/combination of this invention means an amount effective, when administered to a patient, to provide a therapeutic benefit such as an amelioration of symptoms, e.g., an amount effective to decrease the symptoms of a bacterial infection and/or effect a cure. In certain circumstances a patient suffering from a microbial infection may not present symptoms of being infected. Thus a therapeutically effective amount of a compound is also an amount sufficient to significantly reduce the detectable level of microorganism in the patient's blood, serum, other bodily fluids, or tissues. The disclosure also includes, in certain embodiments, using compounds of the disclosure in prophylactic treatment and therapeutic treatment. In the context of prophylactic or preventative treatment a "therapeutically effective amount" is an amount sufficient to significantly decrease the treated patient's risk of contracting a bacterial infection. For example, prophylactic treatment may be administered when a subject will knowingly be exposed to infectious microbes. A significant reduction is any detectable negative change that is statistically significant in a standard parametric test of statistical significance such as Student's T-test, where $p<0.05$.

Chemical Description

Formulae (I)-(VIII) include all subformulae thereof. In certain situations, the compounds of any of Formulae (I)-(VIII) may contain one or more asymmetric elements such as stereogenic centers, stereogenic axes and the like, e.g. asymmetric carbon atoms, so that the compounds can exist in different stereoisomeric forms. These compounds can be, for example, racemates or optically active forms. For compounds with two or more asymmetric elements, these compounds can additionally be mixtures of diastereomers. For compounds having asymmetric centers, it should be understood that all of the optical isomers and mixtures thereof are encompassed. In addition, compounds with carbon-carbon double bonds may occur in Z- and E-forms, with all isomeric forms of the compounds being included in the present disclosure. In these situations, single enantiomers, i.e., optically active forms, can be obtained by asymmetric synthesis, synthesis from optically pure precursors, or by resolution of the racemates. Resolution of the racemates can also be accomplished, for example, by conventional methods such as crystallization in the presence of a resolving agent, or chromatography, using, for example using a chiral HPLC column.

Where a compound exists in various tautomeric forms, the invention is not limited to any one of the specific tautomers, but rather includes all tautomeric forms.

Certain compounds are described herein using a general formula that includes variables, e.g. $R_1$-$R_9$. Unless otherwise specified, each variable within such a formula is defined independently of other variables. Thus, if a group is said to be substituted, e.g. with 0-2 R*, then the group may be substituted with up to two R* groups and R* at each occurrence is selected independently from the definition of R*. Also, combinations of substituents and/or variables are permissible only if such combinations result in stable compounds.

The disclosure includes method of treating a bacterial infection in a subject comprising administering to the subject a compound or a pharmaceutically acceptable salt thereof, of Formula (VI)

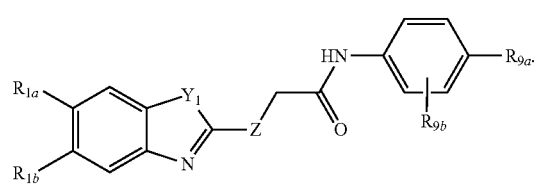

(VI)

In Formula (VI) in this method of treatment the variables $R_{1a}$, $R_{1b}$, $R_{9b}$, and $R_{9a}$ have the following values.

Each of $R_{1a}$ and $R_{1b}$ is independently selected from hydrogen, halogen, cyano, —OCHF$_2$, and CF$_3$, wherein at least one of $R_{1a}$ or $R_{1b}$ is other than hydrogen;

$Y_1$ is selected from NH, O and S;

Z is selected from CH$_2$, NH and S;

$R_{9a}$ is selected from halogen, cyano, —OCH$_3$, optionally substituted pyridinyloxy, optionally substituted pyrimidinyloxy, optionally substituted pyrazinyloxy, and optionally substituted pyridazinyl; and $R_{9b}$ is selected from hydrogen and halogen.

When $R_{9a}$ is optionally substituted pyridinyloxy, optionally substituted pyrimidinyloxy, optionally substituted pyrazinyloxy, or optionally substituted pyridazinyl, $R_{9b}$ is hydrogen, Z is S and $Y_1$ is NH, then at least one of $R_{1a}$ and $R_{1b}$ is other than hydrogen or cyano.

The disclosure includes a method of treating a bacterial infection in a subject comprising administering to the subject a compound or a pharmaceutically acceptable salt thereof, of Formula (VI) in which the variables have the following values.

$R_{1a}$ is selected from hydrogen, bromo, chloro, fluoro, and cyano.

$R_{1b}$ is selected from hydrogen, bromo, fluoro, chloro, cyano, OCHF$_2$, CF$_3$.

$R_{9a}$ is selected from chloro, fluoro, bromo, cyano, —OCH$_3$, pyridin-3-yloxy, 4-methylpyridin-3-yloxy, 5-methylpyridin-3-yloxy, 6-methylpyridin-3-yloxy, 6-chloropyridin-3-yloxy, pyridin-4-yloxy, pyrazin-4-yloxy, pyrazin-2-yloxy, and pyrimidin-2-yloxy.

The disclosure also includes a pharmaceutical composition comprising a compound of Formula (VI) in which the variables carry the following definitions.

Each of $R_{1a}$ and $R_{1b}$ is independently selected from hydrogen, halogen, cyano, —OCHF$_2$, and CF$_3$, wherein at least one of $R_{1a}$ or $R_{1b}$ is other than hydrogen.

$Y_1$ is selected from NH, O and S.

Z is selected from CH$_2$, NH and S.

$R_{9a}$ is selected from halogen, CN, —OCH$_3$, optionally substituted pyridinyloxy, optionally substituted pyrimidinyloxy, optionally substituted pyrazinyloxy, and optionally substituted pyridazinyl; and $R_{9b}$ is selected from hydrogen and halogen.

When $R_{9a}$ is optionally substituted pyridinyloxy, optionally substituted pyrimidinyloxy, optionally substituted pyrazinyloxy, or optionally substituted pyridazinyl, $R_{9b}$ is hydrogen, Z is S and $Y_1$ is NH, then at least one of $R_{1a}$ and $R_{1b}$ is other than hydrogen or cyano.

Wherein the compound is other than

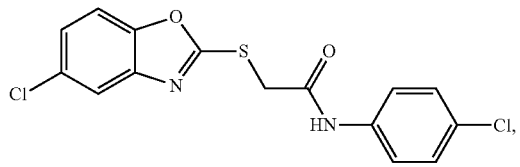

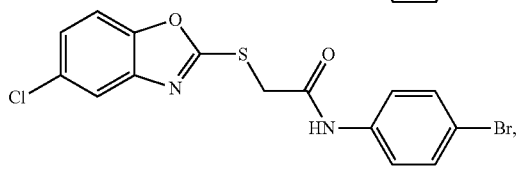

-continued

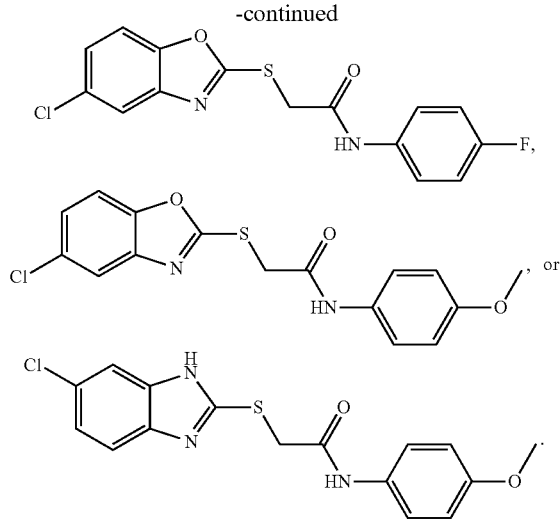

In an embodiment the disclosure includes compounds and salts of Formula (VI) in which the variables have the following values.

$R_{1a}$ is selected from hydrogen, bromo, chloro, fluoro, and cyano.

$R_{1b}$ is selected from hydrogen, bromo, fluoro, chloro, cyano, $OCHF_2$, and $CF_3$.

$R_{9a}$ is selected from chloro, fluoro, bromo, cyano, —$OCH_3$, pyridin-3-yloxy, 4-methylpyridin-3-yloxy, 5-methylpyridin-3-yloxy, 6-methylpyridin-3-yloxy, 6-chloropyridin-3-yloxy, pyridin-4-yloxy, pyrazin-4-yloxy, pyrazin-2-yloxy, and pyrimidin-2-yloxy.

The disclosure also includes compounds and pharmaceutically acceptable salts of Formula (VII)

(VII)

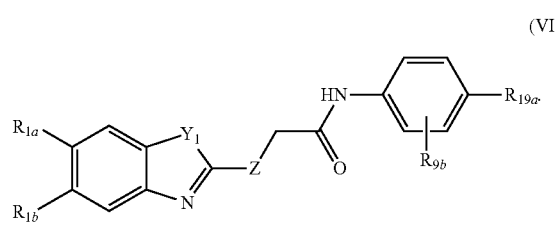

In Formula (VII) the variables have the following definitions.

each of $R_{1a}$ and $R_{1b}$ is independently selected from hydrogen, halogen, cyano, —$OCHF_2$, and $CF_3$, wherein at least one of $R_{1a}$ or $R_{1b}$ is other than hydrogen;

$Y_1$ is selected from NH, O and S;

Z is selected from $CH_2$, NH and S;

$R_{19a}$ is selected from CN, optionally substituted pyridinyloxy, optionally substituted pyrimidinyloxy, optionally substituted pyrazinyloxy, and optionally substituted pyridazinyl; and $R_{9b}$ is selected from hydrogen and halogen.

When $R_{19a}$ is optionally substituted pyridinyloxy, optionally substituted pyrimidinyloxy, optionally substituted pyrazinyloxy, or optionally substituted pyridazinyl, $R_{19b}$ is hydrogen, Z is S and $Y_1$ is NH, then at least one of $R_{1a}$ and $R_{1b}$ is other than hydrogen or cyano.

Wherein the compound of Formula (VII) is other than

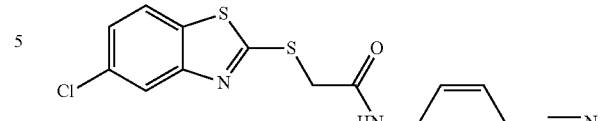

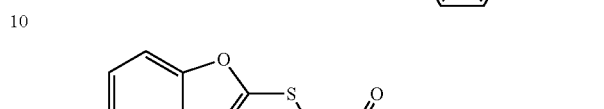

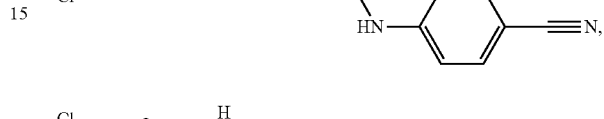

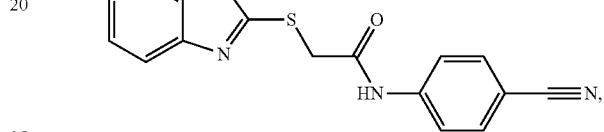

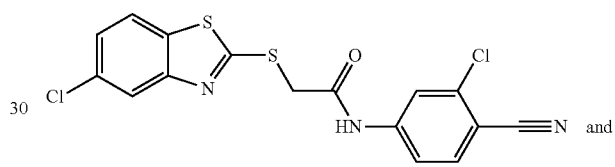

and

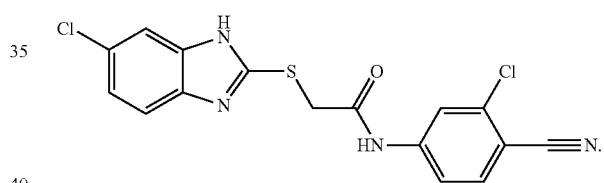

In some embodiments the disclosure includes a compound or salt of Formula (VII) in which the following conditions are met.

$R_{1a}$ is selected from hydrogen, bromo, chloro, fluoro, and cyano;

$R_{1b}$ is selected from hydrogen, bromo, fluoro, chloro, cyano, $OCHF_2$, and $CF_3$.

$R_{19a}$ is selected from cyano, —$OCH_3$, pyridin-3-yloxy, 4-methylpyridin-3-yloxy, 5-methylpyridin-3-yloxy, 6-methylpyridin-3-yloxy, 6-chloropyridin-3-yloxy, pyridin-4-yloxy, pyrazin-4-yloxy, pyrazin-2-yloxy, and pyrimidin-2-yloxy.

In still other embodiments, the disclosure provides a compound of Formula VIII, or a pharmaceutically acceptable salt thereof; a pharmaceutical composition comprising a compound of Formula VIII or a pharmaceutically acceptable salt thereof and a pharmaceutically acceptable carrier; and a method of treating a bacterial infection in a subject comprising administering to the subject a compound of Formula VIII or a pharmaceutically acceptable salt thereof or a pharmaceutical composition comprising a compound of Formula VIII or a pharmaceutically acceptable salt thereof.

The compound of Formula VIII has the structure:

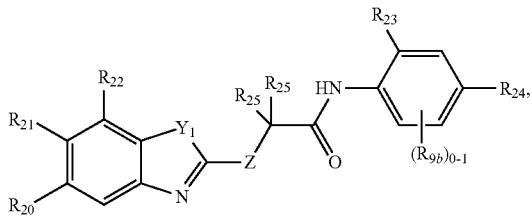

wherein:
each of $R_{20}$ and $R_{21}$ is independently selected from hydrogen, chloro, fluoro, bromo, cyano, —$OCHF_2$, and $CF_3$, wherein at least one of $R_{20}$ or $R_{21}$ is other than hydrogen;
$R_{22}$ is selected from hydrogen, chloro, fluoro, bromo, methyl, ethyl, —$OCH_3$, —$OCH_2CH_3$, $CF_3$, and $CHF_2$
$Y_1$ is selected from NH, O and S;
Z is selected from $CH_2$, NH and S;
$R_{23}$ is selected from hydrogen, chloro, fluoro, bromo, methyl, ethyl, hydroxy, —$OCH_3$, —$OCH_2CH_3$, $CF_3$, and $CHF_2$
$R_{24}$ is selected from chloro, fluoro, bromo, cyano, —$OCH_3$, optionally substituted pyridinyloxy, optionally substituted pyrimidinyloxy, optionally substituted pyrazinyloxy, and optionally substituted pyridazinyl;
each $R_{25}$ is independently selected from hydrogen, hydroxy, halogen, $C_1$-$C_4$ alkyl, and $C_1$-$C_4$ haloalkyl; and
$R_{9b}$, if present, is selected from bromo, chloro and fluoro, wherein:
when $R_{24}$ is optionally substituted pyridinyloxy, optionally substituted pyrimidinyloxy, optionally substituted pyrazinyloxy, or optionally substituted pyridazinyl, Z is S and $Y_1$ is NH, then each of $R_{20}$ and $R_{21}$ is other than hydrogen or cyano.

In certain embodiments of Formula VIII:
$R_{9b}$ is absent or chloro;
$R_{20}$ is selected from hydrogen, bromo, fluoro, chloro, cyano, $OCHF_2$, $CF_3$;
$R_{21}$ is selected from hydrogen, bromo, chloro, fluoro, and cyano;
$R_{22}$ is selected from hydrogen and —$OCH_3$;
$R_{23}$ is selected from hydrogen, chloro, hydroxy, methyl, —$OCH_3$;
$R_{24}$ is selected from chloro, fluoro, bromo, cyano, —$OCH_3$, pyridin-3-yloxy, 4-methylpyridin-3-yloxy, 5-methylpyridin-3-yloxy, 6-methylpyridin-3-yloxy, 6-chloropyridin-3-yloxy, pyridin-4-yloxy, pyrazin-4-yloxy, pyrazin-2-yloxy, and pyrimidin-2-yloxy; and
each $R_{25}$ is hydrogen.

In other embodiments of Formula VIII, the compound is other than

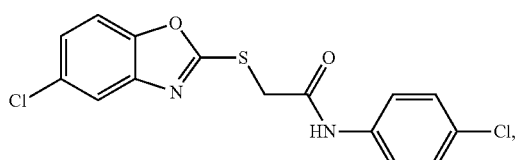

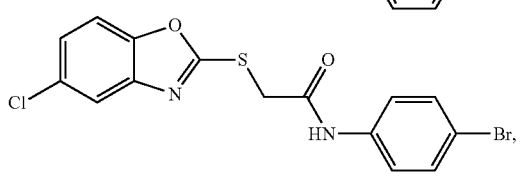

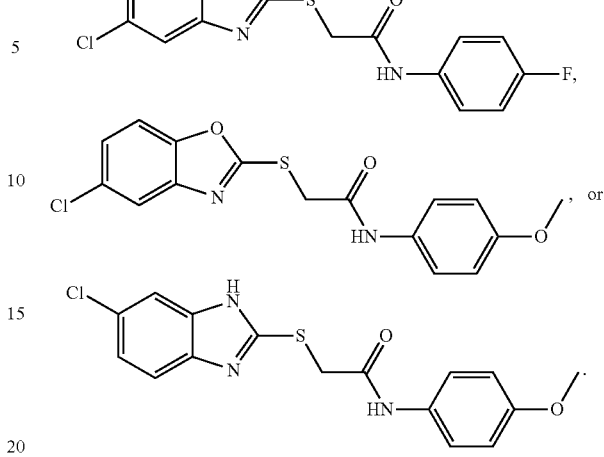

In still other embodiments of Formula VIII:
when $R_{24}$ is chloro, fluoro, bromo, or —$OCH_3$, $R_{22}$ is hydrogen, and Z is S, neither of $R_{20}$ or $R_{21}$ is chloro, fluoro, or bromo; and
the compound is other than.

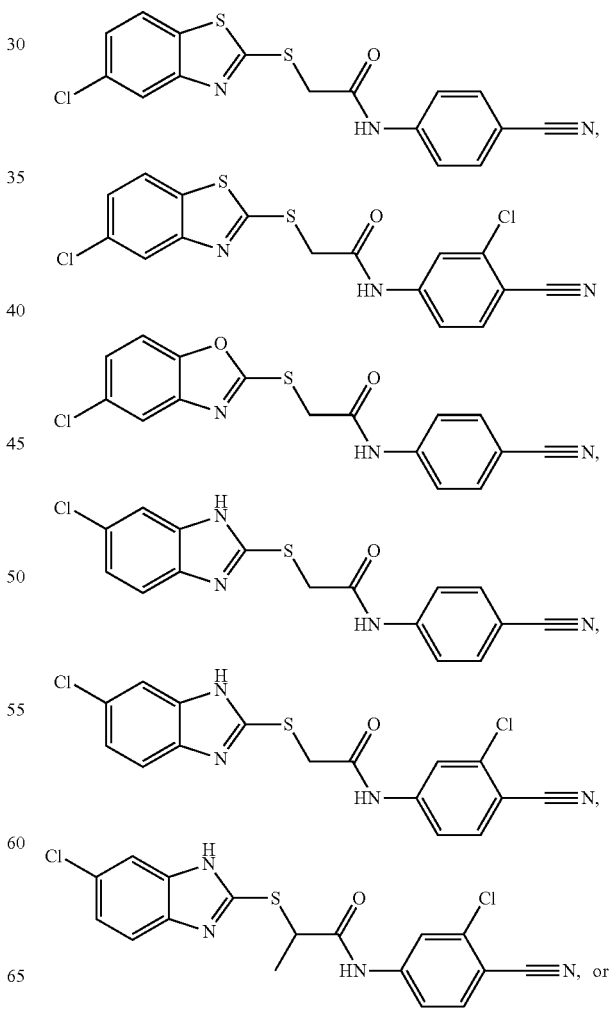

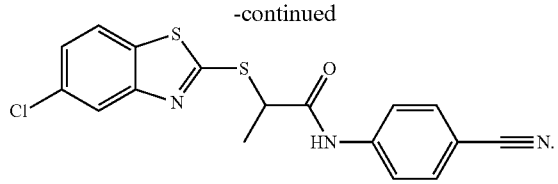

In certain embodiments of Formula VIII, Z is S.

In certain embodiments of Formula VIII, Z is NH or CH$_2$.

Methods of Treatment

The disclosure includes a method of treating a bacterial infection in a patient by administering an effective amount of one or more compounds of the disclosure to a patient at risk for a bacterial infection or suffering from a microorganism infection. Treatment of human patients is particularly contemplated. However, treatment of non-human patients is within the scope of the disclosure. The disclosure includes treatment or prevention of microbial infections in fish, amphibians, reptiles or birds, but a preferred embodiment of the disclosure includes treating mammals.

In some embodiments, the bacterial infection or antibiotic-tolerant infection is caused by a Gram-negative bacterium.

In an embodiment of any of the methods of this disclosure, the microbial infection is the result of a pathogenic bacterial infection. Examples of pathogenic bacteria include, without limitation, bacteria within the genera *Aerobacter, Aeromonas, Acinetobacter, Agrobacterium, Bacillus, Bacteroides, Bartonella, Bordetella, Brucella, Burkholderia Calymmatobacterium, Campylobacter, Citrobacter, Clostridium, Corynebacterium, Enterobacter, Enterococcus, Escherichia, Francisella, Haemophilus, Hafnia, Helicobacter, Klebsiella, Legionella, Listeria, Morganella, Moraxella, Proteus, Providencia, Pseudomonas, Salmonella, Serratia, Shigella, Staphylococcus, Streptococcus, Treponema, Xanthomonas, Vibrio,* and *Yersinia*. Specific examples of such bacteria include *Vibrio harveyi, Vibrio cholerae, Vibrio parahemolyticus, Vibrio alginolyticus, Pseudomonas phosphoreum, Pseudomonas aeruginosa, Yersinia enterocolitica, Escherichia coli, Salmonella typhimurium, Haemophilus influenzae, Helicobacter pylori, Bacillus subtilis, Borrelia burgdorferi, Neisseria meningitidis, Neisseria gonorrhoeae, Yersinia pestis, Campylobacter jejuni, Mycobacterium tuberculosis, Enterococcus faecalis, Streptococcus pneumoniae, Streptococcus pyogenes, Klebsiella pneumoniae, Acinetobacter baumannii, Staphylococcus epidermidis,* and *Staphylococcus aureus.*

In some embodiments, the gram-negative bacterium is a *Pseudomonas*, e.g., *P. aeruginosa*.

In some embodiments, the gram-negative bacterium is *Burkholderia* species.

In some embodiments, the gram-negative bacterium is *Acinetobacter*, e.g., *A. baumannii*.

In some embodiments, the gram-negative bacterium is an Enterobacteriaceae, e.g., *Klebsiella pneumonia*, e.g., *Escherichia coli*, e.g., *Enterobacter cloacae*, e.g., *Serratia marcescens*, e.g., *Salmonella typhimurium*, e.g., *Shigella dysenteriae*, e.g., *Proteus mirabilis*, e.g., *Citrobacter freundii*, e.g., *Yersinia pestis*.

In some embodiments, the infection is a polymicrobial infection, e.g., an infection comprising more than one organism. In some embodiments, the infection comprises at least one of the organisms listed above, e.g., one or more of *Pseudomonas*, e.g., *P. aeruginosa, Kelbsiella*, e.g., *Klebsiella pneumoniae*, and/or *Acinetobacter*, e.g., *A. baumannii*.

In some embodiments, the methods further include administering an additional active agent in combination with a compound of the disclosure, such as an antibiotic selected from the group consisting of: penicillins, cephalosporins, carbacephems, cephamycins, carbapenems, monobactams, quinolones, tetracyclines, aminoglycosides, macrolides, glycopeptides, chloramphenicols, glycylcyclines, lincosamides, lipopeptides, oxazolidinones and fluoroquinolones.

In some embodiments, the bacterial infection is an upper respiratory tract infection, pneumonia, a systemic infection, sepsis and septic shock, a urinary tract infection, a gastrointestinal infection, endocarditis, a bone infection, or an infection of the skin and soft tissue.

In some embodiments, the subject is a mammal, e.g., a human or non-human mammal. In some embodiments, the methods include treating one or more cells, e.g., cells in a culture dish.

In one aspect, the present disclosure features a method of treating a Gram-negative infection in a subject, the method comprising administering to said subject in need of such treatment a therapeutically effective amount of a compound described herein.

In some embodiments, the Gram-negative infection is caused by *Pseudomonas aeruginosa*.

In other embodiments the disclosure includes treating an infection caused by gram positive bacteria, such as *Staphylococcus epidermidis* and *Staphylococcus aureus*.

In some embodiments, the subject is a trauma patient or a burn patient suffering from a burn or skin wound.

In a further aspect, the present disclosure features a method of reducing bacterial tolerance in a subject, the method comprising administering to said subject a therapeutically effective amount of a compound described herein.

In some embodiments, the method further includes identifying said subject suffering from a bacteria tolerant infection.

Dosage levels of the order of from about 0.1 mg to about 140 mg per kilogram of body weight per day, and about 1 mg to about 20 mg per kg body weight, and about 1 mg to 10 mg per kg body weight, and about 4 mg per kg body weight are useful in the treatment of the above-indicated conditions (about 10 mg to about 7 g per patient per day). In certain embodiments about 100 mg to about 5 g of an active agent of this disclosure will be administered per day. In other embodiments about 200 mg to about 3 g, or about 500 mg to about 2 g of active agent will be administered per day. Dosing schedules in which a compound of the disclosure is administered less than once per day are also included in the disclosure. For example controlled release dosage form in which the compound is administered once every 48 hours, twice weekly, or once weekly are also within the scope of the disclosure. The amount of active agent that may be combined with the carrier materials to produce a single dosage form will vary depending upon the host treated and the particular mode of administration. Dosage unit forms will generally contain between from about 50 mg to about 1 g of an active ingredient.

In certain embodiments a therapeutically effective amount of a compound of the disclosure is an amount sufficient to maintain in a patient a serum concentration that is above the minimal inhibitory concentration (MIC) against the bacterium with which the patient is infected until the next dosing of the compound. For example a therapeutically effective amount may be an amount that maintains in a patient a serum concentration of the compound of 0.1 micromolar to 10 micromolar until the next dosing of the compound.

Frequency of dosage may also vary depending on the compound used, the particular disease treated and MIC of the bacteria causing the disease. However, for treatment of most infectious disorders, a dosage regimen of 4 times daily or less is preferred and a dosage regimen of 1 or 2 times daily is particularly preferred.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

EXAMPLES

Abbreviations

| | |
|---|---|
| Ac | acetyl |
| AcOH | acetyl alcohol |
| AcOEt | ethyl acetate |
| aq. | aqueous |
| Bn | benzyl |
| Boc | tert-butoxy carbonyl |
| Cy/CyHex | cyclohexane |
| DCC | N,N'-Dicyclohexylcarbodiimide |
| DCM | dichloromethane |
| DIBAL-H | diisobutylaluminium hydride |
| DIPEA | N,N-Diisopropyl ethylamine |
| DMF | Dimethylformamide |
| DMSO | dimethylsulfoxide |
| EDCI/EDC | 3-(ethyliminomethyleneamino)-N,N-dimethylpropan-1-amine |
| EDTA | ethylenediamine tetraacetic acid |
| eq(s). | equivalent(s) |
| EtOAc | ethyl acetate |
| Et | Ethyl |
| Et$_3$N | triethylamine |
| g | gram(s) |
| h | hour(s) |
| HATU | (Dimethylamino)-N,N-dimethyl(3H-[1,2,3]triazolo[4,5-b]pyridin-3-yloxy)methaniminium hexafluorophosphate |
| HOBt | 1-Hydroxybenzotriazole |
| HPLC | High pressure liquid chromatography |
| LCMS; LC-MS | liquid chromatography mass spectrometry |
| MeOH | Methanol |
| mg | milligram(s) |
| min | Minute(s) |
| mL; ml | milliliter(s) |
| NMe | N-methyl |
| NMR | Nuclear magnetic resonance |
| Ph | Phenyl |
| r.t./RT | Room temperature |
| S. | Saturated |
| SEMCl | 2-(Trimethylsilyl)ethoxymethyl chloride |
| TEA | triethylamine |
| TFA | trifluoroacetic acid |
| THF | Tetrahydrofuran |
| TLC | Thin layer chromatography |
| UPLC | Ultra performance liquid chromatography |

General Methods

The compounds of and useful in the invention can be prepared according to one or more of the General Schemes 1, 2, 3 and 4:

General Scheme 1

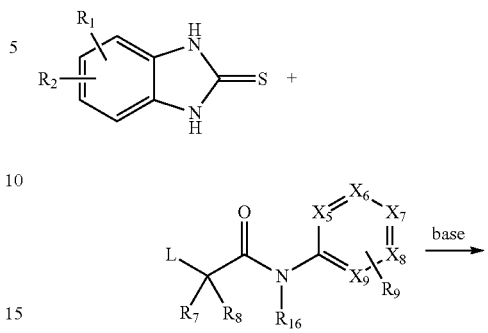

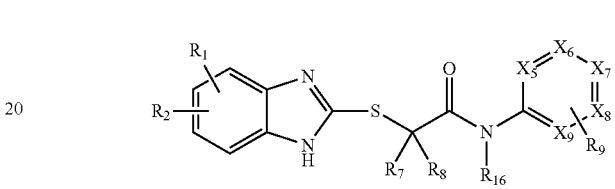

General Scheme 2

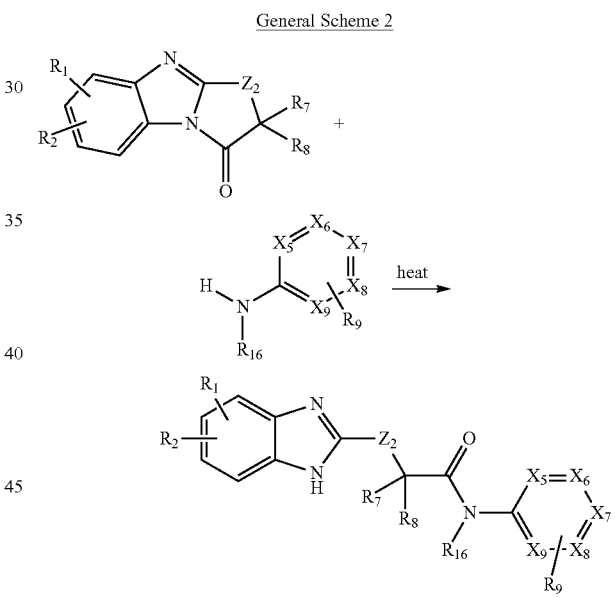

General Scheme 3

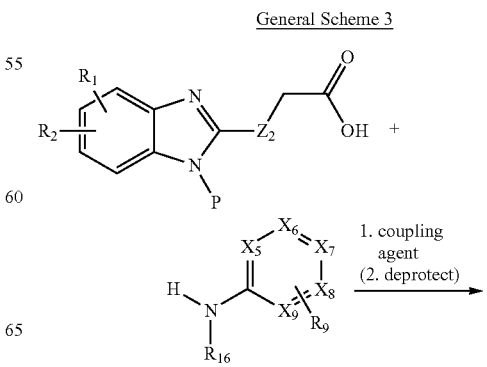

-continued

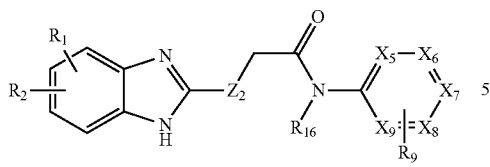

General Scheme 4

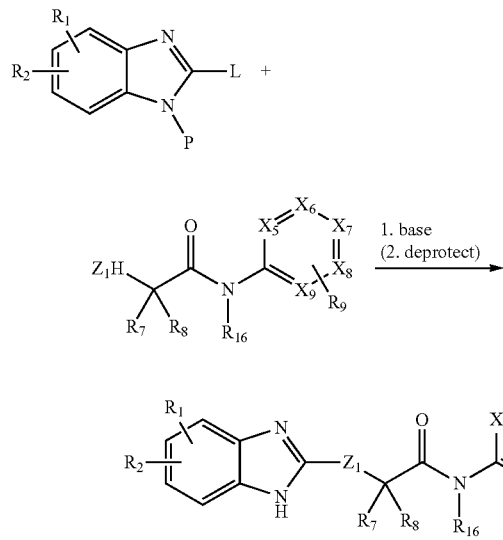

General Scheme 5

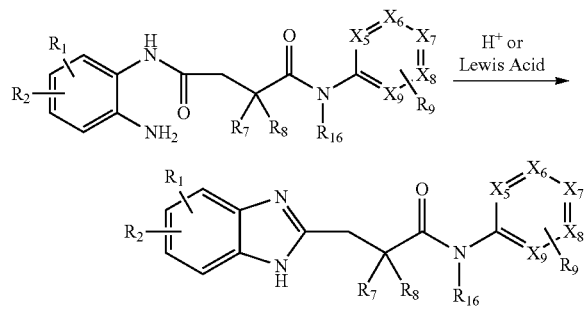

General Scheme 6

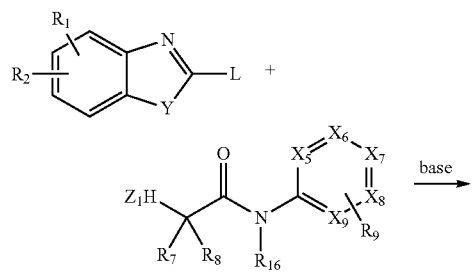

-continued

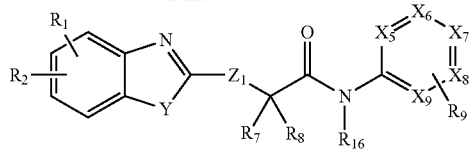

wherein:

L is a leaving group;

$Z_1$ is S, O, or NH;

$Z_2$ is S, O, $NH_2$, or $CH_2$;

Y is O or S;

P is an optional protecting group known in the art, or an N-substituent, such as an alkyl, that is present in a final product; and $R^1$, $R^2$, $R^7$, $R^8$, $R^9$, $R^{16}$, $X^5$, $X^6$, $X^7$, $X^8$, and $X^9$, are as defined herein for any of Formulae I-VIII set forth herein.

Other compounds of the invention can be synthesized by methods related to those described above, known in the art, or otherwise exemplified below.

Biological Methods

Experiments were performed to identify compounds that inhibit the MvfR regulon without altering growth, ultimately attenuating infection. MvfR is a LysR-type transcriptional regulator that directs 4-hydroxy-2-alkylquinolines (HAQs) synthesis, including that of its ligands, 4-hydroxy-2-heptylquinoline (HHQ) and 3,4-dihydroxy-2-heptylquinoline (PQS). MvfR regulates the production of many virulence factors including pyocyanin, one of the many toxins secreted by *Pseudomonas aeruginosa*. Both MvfR and PQS have been demonstrated as essential for pathogenesis in several host models.

MvfR promotes the production of HAQs by binding to and activating the pqs operon, which encodes enzymes for HAQ synthesis. Anthranilic acid (AA), derived from the phnAB, kynABU, and trpEG pathways, is the precursor for HAQs. Pqs A encodes an anthranilate-coenzyme A ligase, which activates anthranilic acid and catalyzes the first committed step to HAQ production. The exact roles of PqsB and PqsC are unknown, though both show homology to acyl-carrier-proteins and both are required for HHQ and PQS production. PqsD is a condensing enzyme that along with PqsA has been shown to be necessary and sufficient for the production of 2,4-dihydroxyquinoline (DHQ), a molecule whose biological role has yet to be determined. The final gene of the operon, PqsE encodes for a putative hydrolase, and while the protein is not required for the synthesis of HAQs, it is necessary for pyocyanin production.

Inhibition of Pyocyanin production is correlated with reduced *P. aeruginosa* infectivity. HHQ and PQS inhibition is also correlated with reduced *P. aeruginosa* infectivity. PQS inhibition is correlated with reduced infectivity of other bacterial pathogens as PQS is known to affect oxygen consumption and cell to cell communication of other Gram-negative and Gram-positive bacteria (Toyofuku, M. et al., Microbes Environ. (2010) 25(1): 1-7).

Example 1

Synthesis of N-(4-phenoxyphenyl)-2-((5-(trifluoromethyl)-1H-benzo[d]imidazol-2-yl)thio)acetamide

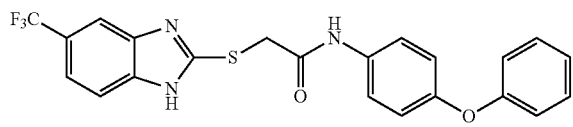 [SMILES: O=C(CSc1nc2cc(C(F)(F)F)ccc2[nH]1)Nc1ccc(Oc2ccccc2)cc1]

Chloroacetyl chloride (1.6 ml) in 20 ml of methylene chloride is added to 3.55 g of 4-phenoxyaniline in 40 ml of methylene chloride containing 2.9 ml of triethylamine. After two hours at room temperature, the mixture is extracted with water to yield 2.74 g of N-(4-phenoxy)-2-chloro-acetamide.

To 2.74 g of N-(4-phenoxy)-2-chloro-acetamide in 180 ml of a 1M NaOH solution containing 130 ml of methanol and 60 ml of water is added 2.82 g of 6-trifluoromethyl-2-thiobenzimidazole and the mixture is heated at 70° C. for 3 hours. The mixture is extracted with ethyl acetate and hexane and the extract is concentrated under reduced pressure to produce N-(4-phenoxyphenyl)-2-((6-nitro-1H-benzo[d]imidazol-2-yl)thio)acetamide.

Example 2

Synthesis of 2-((5-chlorobenzo[d]thiazol-2-yl)amino)-N-(4-(pyridin-3-yloxy)phenyl)acetamide (Compound 71), 2-(5-chlorobenzo[d]thiazol-2-ylamino)-N-(4-cyanophenyl)acetamide (Compound 72) and 2-((6-chlorobenzo[d]thiazol-2-yl)amino)-N-(4-(pyridin-3-yloxy)phenyl)acetamide (Compound 73)

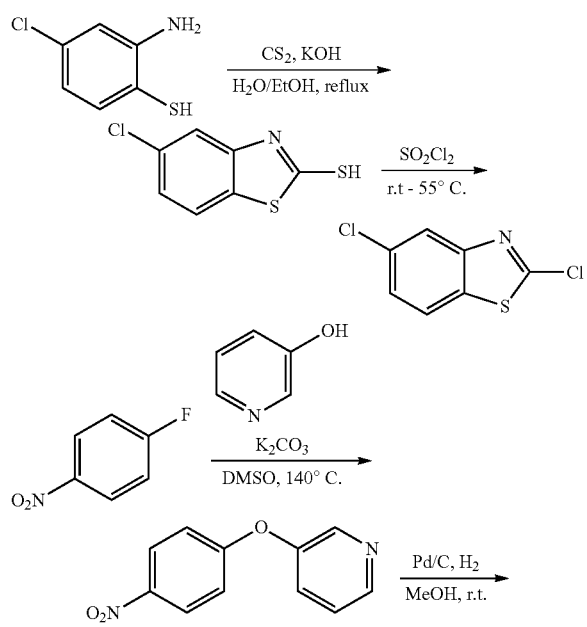

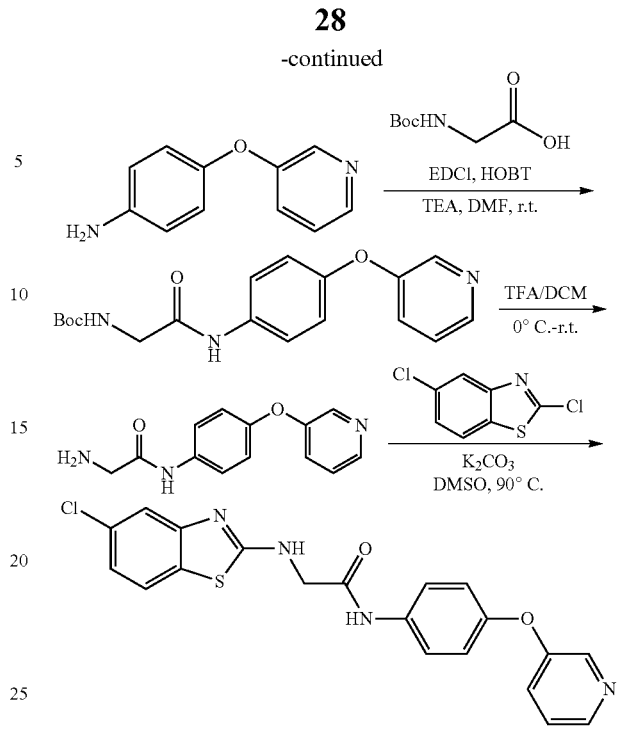

Step 1. 5-Chlorobenzo[d]thiazole-2-thiol

To a solution of 2-amino-4-chlorobenzenethiol (5.0 g, 31.3 mmol) in 100 mL of EtOH and 20 mL of $H_2O$ were added $CS_2$ (1.9 mL, 31.3 mmol) and KOH (1.76 g, 31.3 mmol). The mixture was refluxed overnight and cooled to r.t., followed by addition of active carbon (5 g). The resulting mixture was stirred at r.t. for 1 hr and filtered through Celite. The filtrate was concentrated under reduced pressure to give 5-chlorobenzo[d]thiazole-2-thiol (6.3 g, 99% yield) as yellow solid. LC-MS: m/z: 202 $(M+H)^+$.

Step 2. 2,5-Dichlorobenzo[d]thiazole

5-Chloro-2-mercaptobenzothiazole (1 g, 4.96 mmol) was added in portions over 0.5 hour to 10 mL of sulfuryl chloride at r.t. After addition, the reaction mixture was stirred at r.t. for 1 hr, and then heated to 60° C. for 0.5 hr. The resulting mixture was cooled to r.t. and added slowly to ice. The mixture was stirred for 0.5 hr and extracted with EtOAc. Combined organic layers were dried over anhydrous $Na_2SO_4$ and concentrated. The residue was purified by column chromatography to give 2,5-dichlorobenzo[d]thiazole (0.62 g, 61% yield) as a grey solid. LC-MS: m/z: 204 $(M+H)^+$.

Step 3. 3-(4-Nitrophenoxy)pyridine

To a solution of 1-fluoro-4-nitrobenzene (14.1 g, 0.1 mol) and pyridin-3-ol (12.35 g, 0.13 mol) in DMSO was added $K_2CO_3$ (20.72 g, 0.15 mol). The reaction mixture was heated at 140° C. for 2 hr and cooled down to r.t. The mixture was diluted with water, and extracted with EtOAc. Combined organic layers were dried over anhydrous $Na_2SO_4$ and concentrated. The residue was purified by column chromatography to give 3-(4-nitrophenoxy)pyridine (20.7 g, 96% yield) as yellow solid.

Step 4. 4-(Pyridin-3-yloxy)aniline 3-(4-nitrophenoxy)pyridine (10.2 g, 47.18 mmol) was dissolved in 100 mL MeOH, followed by addition of Pd/C powder (10% wt, 1.1 g). The reaction mixture was stirred at r.t. under $H_2$ atmosphere overnight and filtered through Celite. The filtrate was concentrated to afford 4-(pyridin-3-yloxy)aniline (17.45 g, 98% yield) as grey solid. LC-MS: m/z: 187 $(M+H)^+$.

Step 5. Tert-butyl 2-oxo-2-(4-(pyridin-3-yloxy)phenylamino)ethyl carbamate

To a reaction mixture of 4-(pyridin-3-yloxy)aniline (1.0 g, 5.37 mmol), 2-(tert-butoxycarbonylamino)acetic acid (1.13 g, 6.45 mmol), EDCI (1.03 g, 5.37 mmol), HOBT (1.45 g, 10.74 mmol) in DMF (15 mL) was added TEA (2.2 mL, 16.12 mmol). The mixture was stirred at r.t. overnight, diluted with water, and extracted with EtOAc. Combined organic layers were dried over anhydrous $Na_2SO_4$ and concentrated. The residue was purified by column chromatography to give tert-butyl 2-oxo-2-(4-(pyridin-3-yloxy)phenylamino)ethyl carbamate (1.5 g, 82% yield) as a yellow foam solid. LC-MS: m/z: 344 $(M+H)^+$.

Step 6. 2-Amino-N-(4-(pyridin-3-yloxy)phenyl)acetamide

Tert-butyl-2-oxo-2-(4-(pyridin-3-yloxy)phenylamino) ethyl carbamate (1.05 g, 3.06 mmol) was dissolved in 10 mL DCM at 0° C., followed by slow addition of TFA (2.5 mL). The mixture was stirred at r.t. for 1 hr and concentrated. The residue was carefully quenched with S. aq. $NaHCO_3$ and extracted with EtOAc. Combined organic layers were dried over anhydrous $Na_2SO_4$ and concentrated to give 2-amino-N-(4-(pyridin-3-yloxy)phenyl)acetamide (0.7 g, 94% yield) as yellow oil. LC-MS: m/z: 244 $(M+H)^+$.

Step 7. 2-(5-Chlorobenzo[d]thiazol-2-ylamino)-N-(4-(pyridin-3-yloxy)phenyl)acetamide To a solution of 2-amino-N-(4-(pyridin-3-yloxy)phenyl) acetamide (100 mg, 0.49 mmol) in 2 mL of DMSO was added $K_2CO_3$ (270 mg, 1.96 mmol), followed by addition of 2,5-dichlorobenzo[d]thiazole (119 mg, 0.49 mmol). The reaction mixture was stirred at 90° C. for 2 hr and cooled to r.t. The resulting mixture was diluted with water and extracted with EtOAc. Combined organic layers were dried over anhydrous $Na_2SO_4$ and concentrated. The residue was purified by prep-HPLC to give 2-((5-chlorobenzo[d]thiazol-2-yl)amino)-N-(4-(pyridin-3-yloxy)phenyl)acetamide (16 mg, 8% yield) as a white solid. LC-MS: m/z: 411 $(M+H)^+$. $^1$H NMR (400 MHz, DMSO-$d_6$) δ 10.25 (s, 1H), 8.62 (t, J=5.7 Hz, 1H), 8.45-8.21 (m, 2H), 7.80-7.60 (m, 3H), 7.47-7.26 (m, 3H), 7.07 (dd, J=8.7, 3.1 Hz, 3H), 4.26 (d, J=5.7 Hz, 2H).

The procedure set forth above was used to produce the following compounds using the appropriate starting materials.

2-(5-Chlorobenzo[d]thiazol-2-ylamino)-N-(4-cyanophenyl)acetamide (Compound 72)

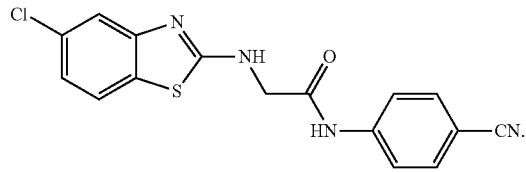 [SMILES: N#Cc1ccc(NC(=O)CNc2nc3cc(Cl)ccc3s2)cc1]

LC-MS: m/z: 343 $(M+H)^+$. $^1$H NMR (400 MHz, DMSO-$d_6$) δ 10.61 (s, 1H), 8.63 (t, J=5.8 Hz, 1H), 7.78 (s, 4H), 7.70 (d, J=8.4 Hz, 1H), 7.38 (d, J=2.0 Hz, 1H), 7.06 (dd, J=8.4, 2.1 Hz, 1H), 4.29 (d, J=5.8 Hz, 2H).

2-((6-chlorobenzo[d]thiazol-2-yl)amino)-N-(4-(pyridin-3-yloxy)phenyl)acetamide (Compound 73)

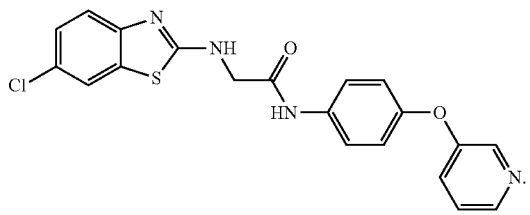 [SMILES: O=C(CNc1nc2ccc(Cl)cc2s1)Nc1ccc(Oc2cccnc2)cc1]

LC-MS: m/z: 411 $(M+H)^+$. $^1$H NMR (400 MHz, DMSO-$d_6$) δ 10.25 (s, 1H), 8.54 (t, J=5.6 Hz, 1H), 8.34 (dd, J=6.3, 3.4 Hz, 2H), 7.83 (d, J=2.0 Hz, 1H), 7.66 (d, J=8.9 Hz, 2H), 7.46-7.30 (m, 3H), 7.24 (dd, J=8.6, 2.1 Hz, 1H), 7.07 (d, J=8.9 Hz, 2H), 4.25 (d, J=5.7 Hz, 2H).

Example 3

Synthesis of 2-((5-chlorobenzo[d]oxazol-2-yl) amino)-N-(4-(pyridin-3-yloxy)phenyl)acetamide (Compound 74) and 2-((5-chlorobenzo[d]oxazol-2-yl)amino)-N-(4-cyanophenyl)acetamide (Compound 75)

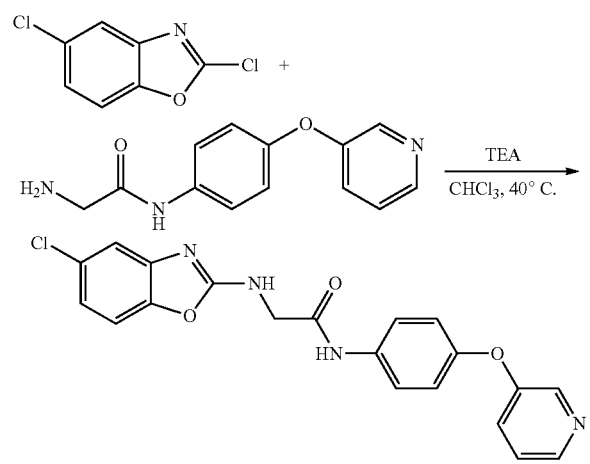

To a solution of 2-amino-N-(4-(pyridin-3-yloxy)phenyl)acetamide (129 mg, 0.5 mmol), 2,5-dichlorobenzo[d]oxazole (100 mg, 0.5 mmol) in 2 mL of CHCl₃ was added TEA (0.3 mL, 2.1 mmol). The reaction mixture was stirred at 40° C. for 2 hr and concentrated. The residue was purified by prep-HPLC to give 2-(5-chlorobenzo[d]oxazol-2-ylamino)-N-(4-(pyridin-3-yloxy)phenyl)acetamide (30 mg, 14% yield) as a white solid. LC-MS: m/z: 395 (M+H)⁺. ¹H NMR (400 MHz, DMSO-d₆) δ 10.23 (s, 1H), 8.57 (t, J=6.1 Hz, 1H), 8.41-8.26 (m, 2H), 7.66 (d, J=9.0 Hz, 2H), 7.46-7.26 (m, 4H), 7.13-6.97 (m, 3H), 4.14 (d, J=6.1 Hz, 2H).

The procedure set forth above was used to produce the following compound using the appropriate starting materials.

2-((5-chlorobenzo[d]oxazol-2-yl)amino)-N-(4-cyanophenyl)acetamide (Compound 75)

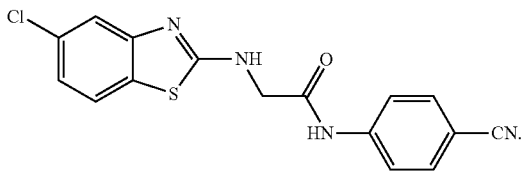 [SMILES: N#Cc1ccc(NC(=O)CNc2nc3cc(Cl)ccc3s2)cc1]

LC-MS: m/z: 327 (M+H)⁺. ¹H NMR (400 MHz, DMSO-d₆) δ 10.61 (s, 1H), 8.60 (t, J=6.2 Hz, 1H), 7.79 (s, 4H), 7.41 (d, J=8.5 Hz, 1H), 7.31 (d, J=2.0 Hz, 1H), 7.03 (dd, J=8.5, 2.1 Hz, 1H), 4.18 (d, J=6.2 Hz, 2H).

Example 4

2-((5-chloro-1H-benzo[d]imidazol-2-yl)thio)-N-(4-(pyridin-4-yloxy)phenyl)acetamide (Compound 76) and Structurally Related Compounds 77-84

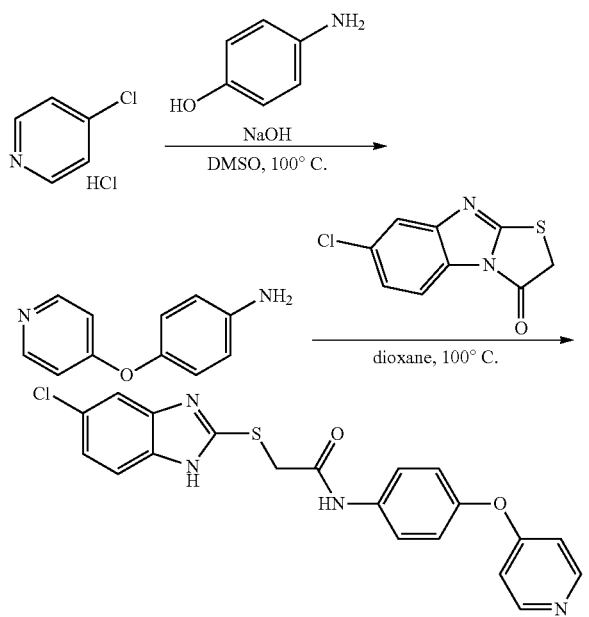

Step 1. 4-(Pyridin-4-yloxy)aniline

To a solution of 4-chloropyridine hydrochloride (1.0 g, 6.67 mmol), 4-aminophenol (0.73 g, 6.67 mmol) in 15 mL of DMSO was added NaOH (0.67 g, 16.67 mmol). The reaction mixture was stirred at 100° C. for 16 hr and cooled to r.t. The resulting mixture was diluted with water and extracted with EtOAc. Combined organic layers were dried over anhydrous Na₂SO₄ and concentrated. The residue was purified by column chromatography to give 4-(pyridin-4-yloxy)aniline (0.83 g, 67% yield) as a pale yellow solid. LC-MS: m/z: 187 (M+H)⁺.

Step 2. 2-(5-Chloro-1H-benzo[d]imidazol-2-ylthio)-N-(4-(pyridin-4-yloxy)phenyl)acetamide 4-(pyridin-4-yloxy)aniline (83 mg, 0.45 mmol) and 7-chlorobenzo[d]thiazolo[3,2-a]imidazol-3(2H)-one (100 mg, 0.45 mmol) were dissolved in dioxane. The reaction mixture was heated to 100° C. for 2 hr and cooled to r.t. The resulting mixture was concentrated and the residue was purified by prep-HPLC to afford 2-((5-chloro-1H-benzo[d]imidazol-2-yl)thio)-N-(4-(pyridin-4-yloxy)phenyl)acetamide (21 mg, 11% yield) as white solid. LC-MS: m/z: 411 (M+H)⁺. ¹H NMR (400 MHz, DMSO-d₆) δ 12.89 (s, 1H), 10.59 (s, 1H), 8.44 (dd, J=4.8, 1.5 Hz, 2H), 8.15 (s, 0.4H), 7.69 (d, J=8.9 Hz, 2H), 7.49 (d, J=24.1 Hz, 2H), 7.15 (d, J=9.0 Hz, 3H), 6.89 (dd, J=4.8, 1.5 Hz, 2H), 4.30 (s, 2H).

The procedure set forth above was used to produce the following compounds using the appropriate starting materials.

2-((5-chloro-1H-benzo[d]imidazol-2-yl)thio)-N-(4-(pyridin-3-yloxy)phenyl)acetamide (Compound 77)

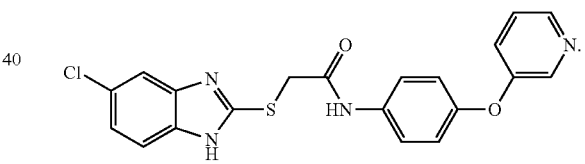

LC-MS: m/z: 411 (M+H)⁺. ¹H NMR (400 MHz, DMSO-d₆) δ 12.87 (s, 1H), 10.64 (s, 1H) 8.32-8.35 (m, 2H), 7.62 (d, J=8.8 Hz, 2H), 7.50 (s, 1H), 7.37-7.45 (m, 3H), 7.15 (d, J=2 Hz, 1H), 7.06 (d, J=8.8 Hz, 2H) 4.28 (s, 2H).

2-((5-chloro-1H-benzo[d]imidazol-2-yl)thio)-N-(4-(pyrazin-2-yloxy)phenyl)acetamide (Compound 78)

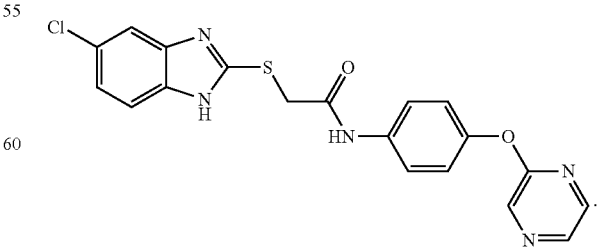

LC-MS: m/z: 412 (M+H)⁺. ¹H NMR (400 MHz, DMSO-d₆) δ 12.87 (s, 1H), 10.56 (s, 1H), 8.52 (d, J=1.2 Hz, 1H), 8.36 (d, J=2.7 Hz, 1H), 8.19 (dd, J=2.6, 1.4 Hz, 1H), 7.64 (d, J=9.0 Hz, 2H), 7.58-7.39 (m, 2H), 7.25-7.09 (m, 3H), 4.30 (s, 2H).

2-((5-chloro-1H-benzo[d]imidazol-2-yl)thio)-N-(4-(pyrimidin-5-yloxy)phenyl)acetamide (Compound 79)

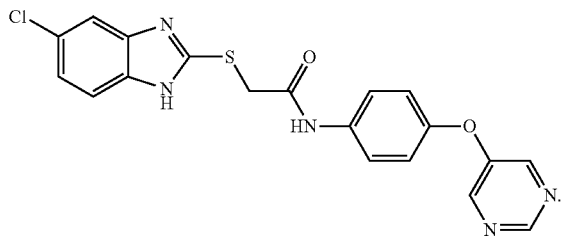 [SMILES: O=C(CSc1nc2cc(Cl)ccc2[nH]1)Nc1ccc(Oc2cncnc2)cc1]

LC-MS: m/z: 412 (M+H)⁺. ¹H NMR (400 MHz, DMSO-d₆) δ12.87 (s, 1H), 10.59 (s, 1H), 8.97 (s, 1H), 8.58 (s, 2H), 7.65 (d, J=9.0 Hz, 2H), 7.51 (s, 1H), 7.45 (d, J=8.5 Hz, 1H), 7.19-7.12 (m, 3H), 4.29 (s, 2H).

2-((5-chloro-1H-benzo[d]imidazol-2-yl)thio)-N-(4-((6-methylpyridin-3-yl)oxy)phenyl)acetamide (Compound 80)

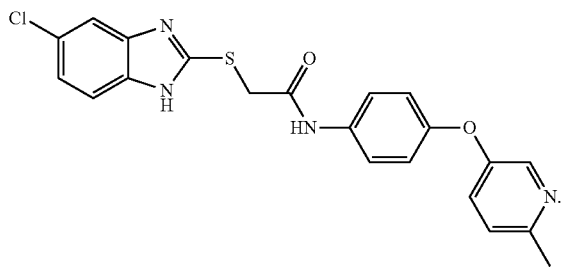 [SMILES: Cc1ccc(Oc2ccc(NC(=O)CSc3nc4cc(Cl)ccc4[nH]3)cc2)cn1]

LC-MS: m/z: 425 (M+H)⁺. ¹H NMR (400 MHz, DMSO-d₆) δ 12.85 (s, 1H), 10.51 (s, 1H), 8.23-8.15 (m, 1H), 7.61 (d, J=9.0 Hz, 2H), 7.55-7.40 (m, 2H), 7.28 (dt, J=21.2, 5.6 Hz, 2H), 7.15 (dd, J=8.5, 1.9 Hz, 1H), 7.01 (d, J=8.9 Hz, 2H), 4.28 (s, 2H), 2.44 (s, 3H).

2-(5-Chloro-1H-benzo[d]imidazol-2-ylthio)-N-(4-(5-methylpyridin-3-yloxy)phenyl)acetamide (Compound 81)

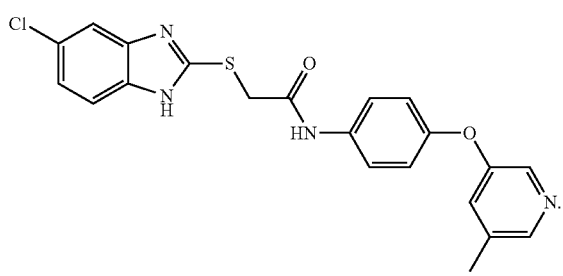 [SMILES: Cc1cncc(Oc2ccc(NC(=O)CSc3nc4cc(Cl)ccc4[nH]3)cc2)c1]

LC-MS: m/z: 425 (M+H)⁺. ¹H NMR (400 MHz, DMSO-d₆) δ 12.86 (s, 1H), 10.53 (s, 1H), 8.27-8.04 (m, 2H), 7.63 (d, J=9.0 Hz, 2H), 7.57-7.41 (m, 2H), 7.21-7.13 (m, 2H), 7.06 (d, J=8.9 Hz, 2H), 4.29 (s, 2H), 2.27 (s, 3H).

2-((5-chloro-1H-benzo[d]imidazol-2-yl)thio)-N-(4-((5-methylpyridin-3-yl)oxy)phenyl)acetamide (Compound 82)

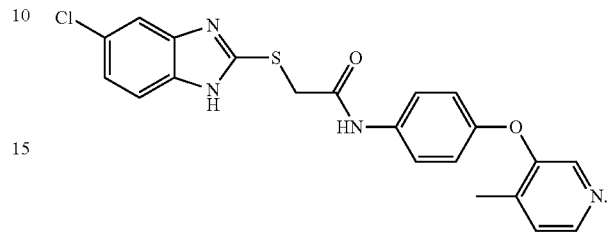

LC-MS: m/z: 425 (M+H)⁺. ¹H NMR (400 MHz, DMSO-d₆) δ 12.78 (s, 1H), 10.49 (s, 1H), 8.28 (d, J=4.8 Hz, 1H), 8.12 (s, 1H), 7.68-7.30 (m, 5H), 7.15 (dd, J=8.5, 1.9 Hz, 1H), 6.93 (d, J=8.9 Hz, 2H), 4.28 (s, 2H), 2.20 (s, 3H).

2-((5-chloro-1H-benzo[d]imidazol-2-yl)thio)-N-(4-((2-chloropyridin-3-yl)oxy)phenyl)acetamide (Compound 83)

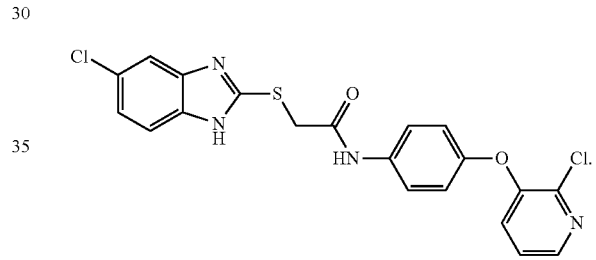

LC-MS: m/z: 445 (M+H)⁺. ¹H NMR (400 MHz, DMSO-d₆) δ 12.87 (s, 1H), 10.55 (s, 1H), 8.20 (dd, J=4.0, 2.2 Hz, 1H), 7.64 (d, J=9.0 Hz, 2H), 7.60-7.29 (m, 4H), 7.16 (dd, J=8.5, 1.9 Hz, 1H), 7.06 (d, J=9.0 Hz, 2H), 4.30 (s, 2H).

2-((5-chloro-1H-benzo[d]imidazol-2-yl)thio)-N-(4-((6-chloropyridin-3-yl)oxy)phenyl)acetamide (Compound 84)

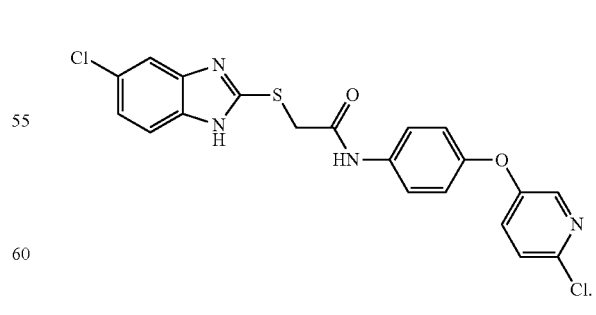

LC-MS: m/z: 445 (M+H)⁺. ¹H NMR (400 MHz, DMSO-d₆) δ 12.86 (s, 1H), 10.55 (s, 1H), 8.18 (d, J=2.7 Hz, 1H), 7.64 (d, J=8.9 Hz, 2H), 7.47 (dt, J=8.8, 5.8 Hz, 4H), 7.29-6.97 (m, 3H), 4.29 (s, 2H).

Example 5

Synthesis of 3-(5-chlorobenzo[d]thiazol-2-yl)-N-(4-(pyridin-3-yloxy)phenyl)propanamide (Compound 85) and 3-(6-chlorobenzo[d]thiazol-2-yl)-N-(4-(pyridin-3-yloxy)phenyl)propanamide (Compound 86)

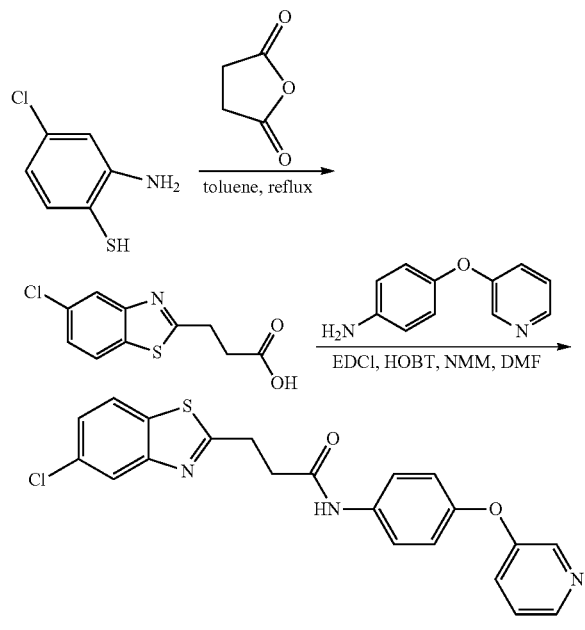

Step 1. 3-(5-Chlorobenzo[d]thiazol-2-yl)propanoic acid

To a solution of 2-amino-4-chlorobenzenethiol (1.6 g, 10 mmol) in toluene (30 mL) was added dihydrofuran-2,5-dione (1.0 g, 10 mmol) at r.t. The mixture was stirred at r.t. for 4 hr and then at reflux for another 2 hr. The resulting mixture was cooled and concentrated under reduced pressure. The residue was purified by re-crystallization from absolute EtOH (20 mL) to give 3-(5-chlorobenzo[d]thiazol-2-yl)propanoic acid (1.6 g, 67%) as white crystals. LC-MS: m/z: 242 (M+H)$^+$

Step 2. 3-(5-Chlorobenzo[d]thiazol-2-yl)-N-(4-(pyridin-3-yloxy)phenyl)propanamide To a solution of 3-(5-chlorobenzo[d]thiazol-2-yl)propanoic acid (120 mg, 0.5 mmol) in DMF (10 mL) were added EDCI (115 mg, 0.6 mmol), HOBT (135 mg, 1 mmol), 4-(pyridin-3-yloxy)aniline (111 mg, 0.6 mmol) and Et$_3$N (200 mg, 2 mmol) at r.t. The mixture was stirred at r.t. for 4 hr until LCMS showed the reaction completed. The resulting mixture was poured into S. aq. NaHCO$_3$ (30 mL) and extracted with DCM (2×20 mL). Combined organic layers were washed with S. aq. LiCl (30 mL), dried over anhydrous Na$_2$SO$_4$ and concentrated reduced pressure. The residue was purified by prep. HPLC to give 3-(5-chlorobenzo[d]thiazol-2-yl)-N-(4-(pyridin-3-yloxy)phenyl)propanamide (60 mg, 29%) as a white solid.

LC-MS: m/z: 410 (M+H)$^+$. $^1$H NMR (400 MHz, DMSO-d$_6$) δ 10.12 (s, 1H), 8.32-8.34 (m, 2H), 8.10 (d, J=8.4 Hz, 1H), 8.01 (s, 1H), 7.63 (d, J=8.8 Hz, 2H), 7.36-7.48 (m, 3H), 7.05 (d, J=8.8 Hz, 2H), 3.44 (t, J=7.2 Hz, 2H), 2.95 (t, J=7.2 Hz, 2H).

The procedure set forth above was used to produce the following compound using the appropriate starting materials.

3-(6-Chlorobenzo[d]thiazol-2-yl)-N-(4-(pyridin-3-yloxy)phenyl)propanamide (Compound 86)

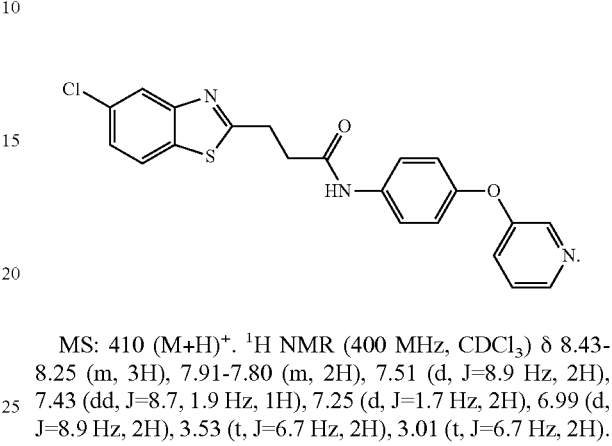

MS: 410 (M+H)$^+$. $^1$H NMR (400 MHz, CDCl$_3$) δ 8.43-8.25 (m, 3H), 7.91-7.80 (m, 2H), 7.51 (d, J=8.9 Hz, 2H), 7.43 (dd, J=8.7, 1.9 Hz, 1H), 7.25 (d, J=1.7 Hz, 2H), 6.99 (d, J=8.9 Hz, 2H), 3.53 (t, J=6.7 Hz, 2H), 3.01 (t, J=6.7 Hz, 2H).

Example 6

Synthesis of N-(2-((5-chloro-1H-benzo[d]imidazol-2-yl)thio)ethyl)-4-(pyridin-3-yloxy)benzamide (Compound 87) and N-(2-(5-chloro-1H-benzo[d]imidazol-2-ylthio)ethyl)-4-cyanobenzamide (Compound 88)

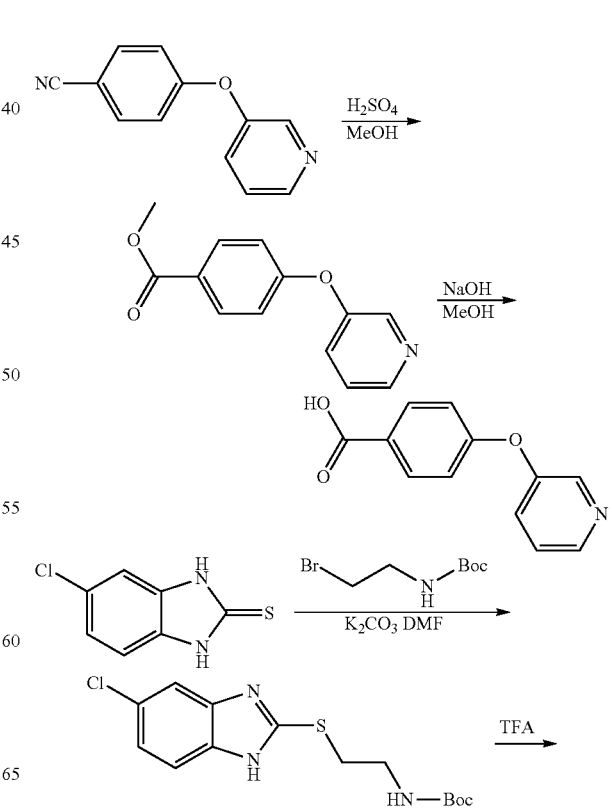

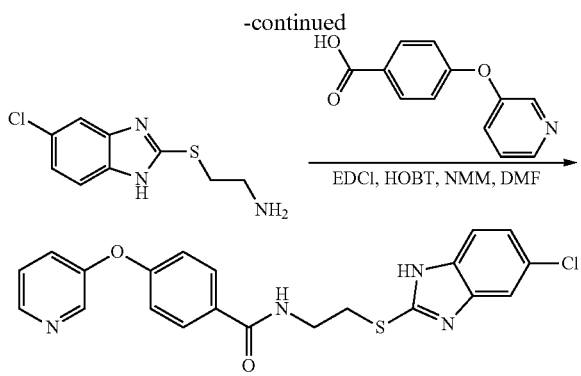

Step 1. Methyl 4-(pyridin-3-yloxy)benzoate

To a solution of 4-(pyridin-3-yloxy)benzonitrile (1 g, 5.1 mmol) in MeOH (10 mL) was added H$_2$SO$_4$ (2 mL). The mixture was stirred at 75° C. for 6 hr. The resulting mixture was diluted with S. aq. Na$_2$CO$_3$ (20 mL) and extracted with EtOAc. Combined organic layers were dried over anhydrous Na$_2$SO$_4$ and concentrated under reduced pressure to give methyl 4-(pyridin-3-yloxy)benzoate (0.9 g, 77.5% yield). LC-MS: m/z: 230 (M+H)$^+$.

Step 2. Methyl 4-(pyridin-3-yloxy)benzoic acid

To a solution of methyl 4-(pyridin-3-yloxy)benzoate in MeOH (10 mL) was added aq. NaOH (2 mL). The mixture was stirred at 75° C. for 1 hr, diluted with 1N HCl (10 ml), and extracted with EtOAc. Combined organic layers were dried over anhydrous Na$_2$SO$_4$ and concentrated under reduced pressure to give 4-(pyridin-3-yloxy)benzoic acid (0.8 g, 93% yield). LC-MS: m/z: 215 (M+H)$^+$.

Step 3: tert-Butyl 2-(5-chloro-1H-benzo[d]imidazol-2-ylthio)ethylcarbamate

To a solution of 5-chloro-1H-benzo[d]imidazole-2(3H)-thione (500 mg, 2.7 mmol), tert-butyl 2-bromoethylcarbamate (670 mg, 3.0 mmol) in 10 mL of DMF was added Cs$_2$CO$_3$ (1760 mg, 5.4 mmol). The reaction mixture was stirred at r.t. for 2 hr, diluted with water (10 mL), and extracted with EtOAc. Combined organic layers were dried over anhydrous Na$_2$SO$_4$ and concentrated under reduced pressure to give tert-butyl 2-(5-chloro-1H-benzo[d]imidazol-2-ylthio)ethylcarbamate (500 mg, 57% yield) as a white solid. LC-MS: m/z: 328 (M+H)$^+$.

Step 4: 2-(5-Chloro-1H-benzo[d]imidazol-2-ylthio)ethanamine

A solution of tert-butyl 2-(5-chloro-1H-benzo[d]imidazol-2-ylthio) ethylcarbamate (500 mg, 1.5 mmol) in 5 mL of TFA was stirred at r.t. for 4 h. The resulting mixture was concentrated under reduced pressure to give 2-(5-chloro-1H-benzo[d]imidazol-2-ylthio)ethanamine TFA salt (510 mg, 100% yield) as a white solid. LC-MS: m/z: 228 (M+H)$^+$.

Step 5: N-(2-((5-chloro-1H-benzo[d]imidazol-2-yl)thio)ethyl)-4-(pyridin-3-yloxy)benzamide To a mixture of 2-(5-chloro-1H-benzo[d]imidazol-2-ylthio)ethanamine (50 mg, 0.22 mmol), 4-(pyridin-3-yloxy)benzoic acid (52 mg, 0.24 mmol), EDCI (55 mg, 0.29 mmol), HOBT (39 mg, 0.29 mmol) in DMF (5 ml) was added NMM (0.1 ml). The reaction mixture was stirred at r.t. for 3 hr, diluted with water, and extracted with EtOAc. Combined organic layers were dried over anhydrous Na$_2$SO$_4$ and concentrated under reduced pressure. The residue was purified by flash column chromatography to give N-(2-((5-chloro-1H-benzo[d]imidazol-2-yl)thio)ethyl)-4-(pyridin-3-yloxy)benzamide (20 mg, 22% yield) as white foam solid. LC-MS: m/z: 425 (M+H)$^+$. $^1$H NMR (400 MHz, DMSO-d$_6$) δ 12.75 (s, 1H), 8.83 (t, J=5.7 Hz, 1H), 8.43 (m, 2H), 7.87 (m, 2H), 7.54-7.43 (m, 4H), 7.15-7.07 (m, 3H), 3.67-3.2828 (d, J=5.7 Hz, 4H).

The procedure set forth above was used to produce the following compound using the appropriate starting materials.

N-(2-((5-chloro-1H-benzo[d]imidazol-2-yl)thio)ethyl)-4-cyanobenzamide (Compound 88)

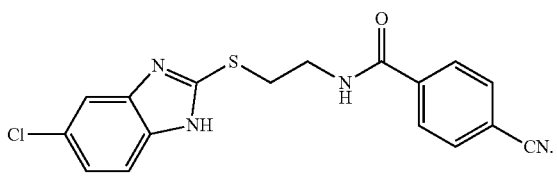 [SMILES: N#Cc1ccc(C(=O)NCCSc2nc3cc(Cl)ccc3[nH]2)cc1]

LC-MS: m/z: 357 (M−H)$^+$. $^1$H NMR (400 MHz, DMSO-d$_6$) δ 12.78 (s, 1H), 9.08 (s, 1H), 7.98-7.94 (m, 4H), 7.47 (m, 2H), 7.15 (m, 2H), 3.70-3.33 (d, J=5.7 Hz, 4H).

Example 7

2-((5-chloro-1H-indol-2-yl)thio)-N-(4-(pyridin-3-yloxy)phenyl)acetamide (Compound 89) and 2-((5-chloro-1H-indol-2-yl)thio)-N-(4-cyanophenyl)acetamide (Compound 90)

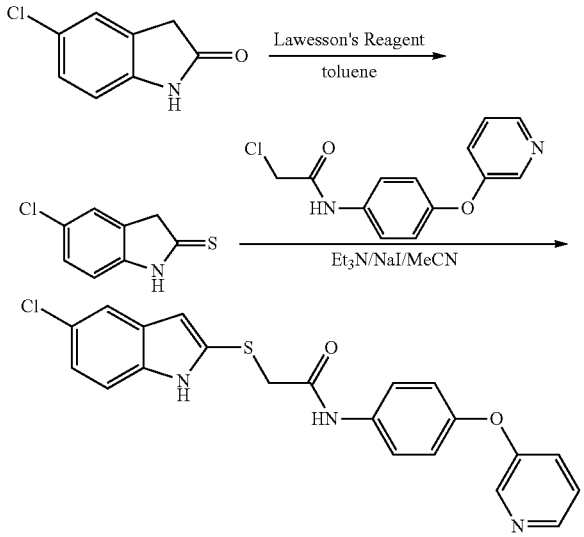

Step 1. 5-Chloroindoline-2-thione

To a solution of 5-chloroindolin-2-one (336 mg, 2 mmol) in toluene (12 ml) was added Lawesson's Reagent (1.2 g, 3 mmol). The mixture was stirred at 105° C. for 3 hr. The resulting mixture was cooled and concentrated under reduced pressure. The residue was diluted with water (40 mL) and extracted with DCM (40 mL). Combined organic layers were dried over anhydrous Na$_2$SO$_4$, and concentrated under reduced pressure. The residue was purified by flash column chromatography to give 5-chloroindoline-2-thione (270 mg, 75% yield) as a white solid. LC-MS: m/z: 184 (M+H)$^+$.

Step 2. 2-((5-chloro-1H-indol-2-yl)thio)-N-(4-(pyridin-3-yloxy)phenyl)acetamide

To a solution of 5-chloroindoline-2-thione (184 mg, 1 mmol) in MeCN (12 ml) was added 2-chloro-N-(4-(pyridin-3-yloxy)phenyl)acetamide (263 mg, 1 mmol), Et$_3$N (202 mg, 2 mmol) and NaI (15 mg, 0.1 mmol). The reaction mixture was stirred at 30° C. for 6 hr and concentrated. The residue was purified by flash column chromatography to give 2-((5-chloro-1H-indol-2-yl)thio)-N-(4-(pyridin-3-yloxy)phenyl)acetamide (50 mg, 13% yield) as a white solid. LC-MS: m/z: 410 (M+H)$^+$. $^1$H NMR (400 MHz, DMSO-d$_6$) δ 11.61 (s, 1H), 10.23 (s, 1H), 8.44-8.18 (m, 2H), 7.59 (d, J=8.9 Hz, 2H), 7.50 (d, J=1.8 Hz, 1H), 7.43-7.22 (m, 3H), 7.14-6.87 (m, 3H), 6.52 (d, J=1.5 Hz, 1H), 3.84 (s, 2H).

The procedure set forth above was used to produce the following compounds using the appropriate starting materials.

2-((5-Chloro-1H-indol-2-yl)thio)-N-(4-cyanophenyl)acetamide (Compound 90)

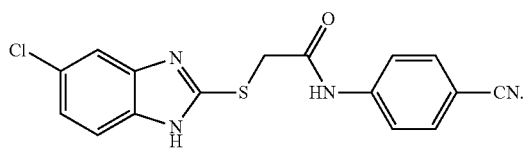 [SMILES: N#Cc1ccc(NC(=O)CSc2nc3cc(Cl)ccc3[nH]2)cc1]

LC-MS: m/z: 342 (M+H)$^+$. $^1$H NMR (400 MHz, DMSO-d$_6$) δ 11.62 (s, 1H), 10.63 (s, 1H), 7.74 (m, 4H), 7.49 (d, J=1.9 Hz, 1H), 7.31 (d, J=8.6 Hz, 1H), 7.07 (dd, J=8.6, 2.1 Hz, 1H), 6.52 (d, J=1.4 Hz, 1H), 3.85 (s, 2H).

Example 8

Synthesis of 1-((5-chloro-1H-benzo[d]imidazol-2-yl)thio)-N-(4-(pyridin-3-yloxy)phenyl)methanesulfonamide (Compound 91)

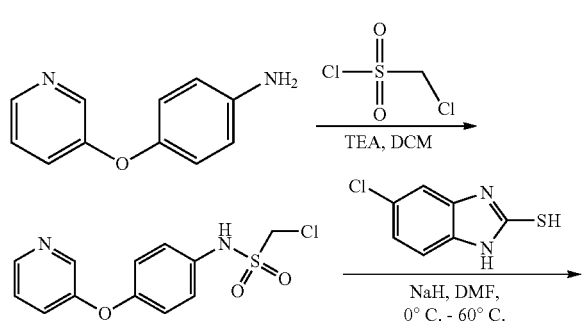

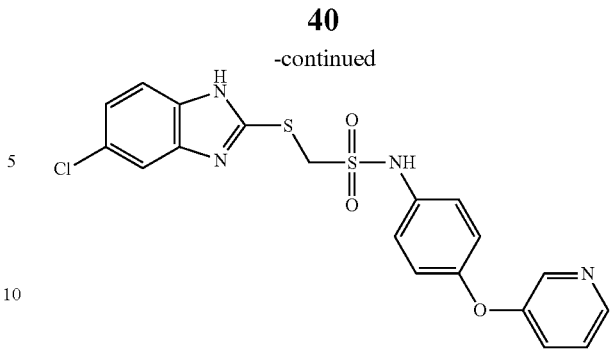

Step 1. 1-Chloro-N-(4-(pyridin-3-yloxy)phenyl)methanesulfonamide

To a stirred solution of 4-(pyridin-3-yloxy)aniline (500 mg, 5.4 mmol) in DCM (10 mL) at 0° C. was added TEA (1.5 mL, 10.8 mmol), followed by dropwise addition of a solution of chloromethanesulfonyl chloride (947 mg, 6.4 mmol) in DCM (2 mL). After addition, the reaction mixture was stirred at 10° C. for 0.5 hr then at r.t. overnight. The resulting mixture was concentrated under reduced pressure to dryness. The residue was purified by column chromatography to afford the desired product (300 mg, 37% yield). MS: 299 (M+H)$^+$.

Step 2. 1-((5-chloro-1H-benzo[d]imidazol-2-yl)thio)-N-(4-(pyridin-3-yloxy)phenyl)methanesulfonamide To a stirred solution of 5-chloro-1H-benzo[d]imidazole-2-thiol (566 mg, 3.03 mmol) in 5 mL DMF at 0° C. was added NaH (121 mg, 3.03 mmol). The mixture was kept stirring for 0.5 h at r.t. followed by addition of a solution of 1-chloro-N-(4-(pyridin-3-yloxy)phenyl)methanesulfonamide (300 mg, 1.01 mmol) in DMF. The reaction mixture was then stirred at 70° C. for 16 hr. The resulting mixture was poured into the ice-water and extracted with EtOAc. Combined organic layers were dried over anhydrous Na$_2$SO$_4$ and concentrated under reduced pressure. The residue was purified by prep-HPLC to give 1-((5-chloro-1H-benzo[d]imidazol-2-yl)thio)-N-(4-(pyridin-3-yloxy)phenyl)methanesulfonamide (200 mg, 45% yield). LC-MS: m/z: 447 (M+H)$^+$. $^1$H NMR (400 MHz, CDCl$_3$) δ 8.39 (dd, J=4.1, 1.7 Hz, 1H), 8.34 (d, J=1.8 Hz, 1H), 8.22 (s, 1H), 7.55-7.29 (m, 4H), 7.20 (d, J=8.7 Hz, 3H), 6.91 (d, J=8.8 Hz, 2H), 4.64 (s, 2H), 1.97 (s, 1H).

Example 9

Synthesis of 3-(6-chlorobenzo[d]oxazol-2-yl)-N-(4-(pyridin-3-yloxy)phenyl)propanamide (Compound 92)

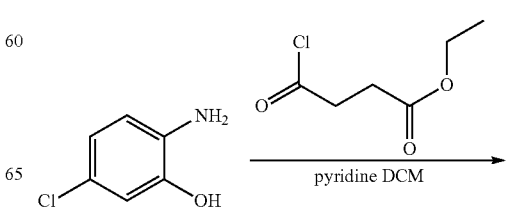

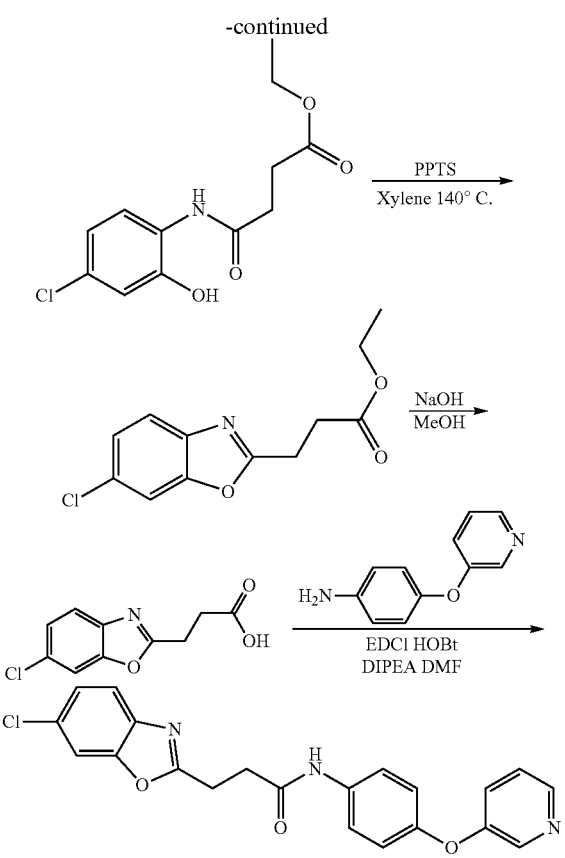

Step 1. Ethyl 4-((4-chloro-2-hydroxyphenyl)amino)-4-oxobutanoate

To a mixture of 2-amino-5-chlorophenol (3 g, 21 mmol), pyridine (3.3 g, 42 mmol) in DCM (20 mL) was added ethyl 4-chloro-4-oxobutanoate (4.1 g, 27 mmol). The mixture was stirred at r.t. for 1 hr and then diluted with water and extracted with EtOAc. The combined organic layers were dried over anhydrous Na$_2$SO$_4$ and concentrated under reduced pressure. The residue was purified by flash column chromatography to give ethyl 4-((4-chloro-2-hydroxyphenyl)amino)-4-oxobutanoate (2.2 g, 39% yield) as oil. LC-MS: m/z 272 (M+H)$^+$.

Step 2. Ethyl 3-(6-chlorobenzo[d]oxazol-2-yl)propanoate

A mixture of ethyl 4-((4-chloro-2-hydroxyphenyl) amino)-4-oxobutanoate (2 g, 7.3 mmol) and PPTS (3.7 g, 14.6 mmol) in xylene was stirred at 140° C. for 2 hr. The resulting mixture was cooled to r.t. and concentrated under reduced pressure. The residue was purified by flash column chromatography to give ethyl 3-(6-chlorobenzo[d]oxazol-2-yl) propanoate (0.8 g, 43.3% yield). LC-MS: m/z 254 (M+H)$^+$.

Step 3. 3-(6-Chlorobenzo[d]oxazol-2-yl)propanoic acid

A mixture of ethyl 3-(6-chlorobenzo[d]oxazol-2-yl)propanoate (0.8 g, 3.2 mmol) and NaOH (0.38 g, 9.6 mmol) in 10 ml of MeOH was stirred at 70° C. for 0.5 hr. The resulting mixture was cooled to r t, diluted with water, and extracted with EtOAc. The combined organic layers were dried over anhydrous Na$_2$SO$_4$ and concentrated under reduced pressure to give 3-(6-chlorobenzo[d]oxazol-2-yl)propanoic acid (0.5 g, 67.3% yield) as pale yellow solid which was used directly in the next step without any further purification. LC-MS: m/z 226 (M+H)$^+$.

Step 4. 3-(6-chlorobenzo[d]oxazol-2-yl)-N-(4-(pyridin-3-yloxy)phenyl)propanamide To a mixture of 3-(6-chlorobenzo[d]oxazol-2-yl)propanoic acid (100 mg, 0.44 mmol), 4-(pyridin-3-yloxy)benzenamine (90 mg, 0.48 mmol), EDCI (102 mg, 0.53 mmol), HOBT (72 mg, 0.53 mmol) in DMF (10 mL) was added DIPEA (114 mg, 0.88 mmol). The mixture was stirred at r.t. for 3 hr, then diluted with water and extracted with EtOAc. The combined organic layers were dried over anhydrous Na$_2$SO$_4$ and concentrated under reduced pressure. The residue was purified by flash column chromatography to give 3-(6-chlorobenzo[d]oxazol-2-yl)-N-(4-(pyridin-3-yloxy) phenyl)propanamide (30 mg, 18% yield) as a white foamy solid. LC-MS: m/z: 394 (M+H)$^+$. $^1$H NMR (400 MHz, DMSO-d$_6$) δ 10.19 (s, 1H), 8.32 (m, 2H), 7.90 (s, 1H), 7.70-7.61 (m, 3H), 7.40-7.34 (m, 3H), 7.03 (m, 2H), 3.34-2.94 (d, J=5.7 Hz, 4H).

Example 10

Intermediates and General Synthesis Scheme for Compounds 23, 56, 57 and 93-150

Preparation of Intermediates A

Intermediates A have the general formula:

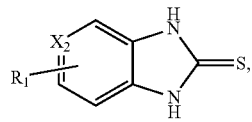

wherein R$_1$ is as defined for Formulae I-VIII. To a solution of the R$^1$-substituted 1,2-di-aniline (1 eq.) and DMAP (1.07 eq.) in MeCN (~0.05 M), at r.t., was added portion-wise a solution of 1,1'-thiocarbonyldiimidazole (2.5 to 1.5 eq.) in MeCN (~0.2 M) and the mixture was stirred at r.t. overnight. The resulting reaction mixture was either filtered (precipitate formation) or concentrated under vacuum, the obtained solid washed with DCM (5-10 vol) and dried under vacuum to give the target Intermediate A used in the next step without any further purification.

Isolation of the intermediates A was also alternatively achieved via flash chromatography on silica-gel (eluting with Cy/EtOAc) or via amine silica-gel (eluting with EtOAc/MeOH) to give the desired intermediate A. This general procedure was used to produce the following intermediates A:

TABLE 1

Intermediates A

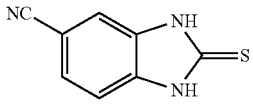  A1

TABLE 1-continued

Intermediates A

| | |
|---|---|
| 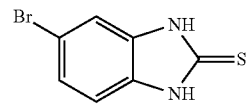 | A2 |
| 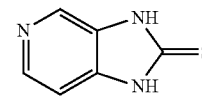 | A3 |
| 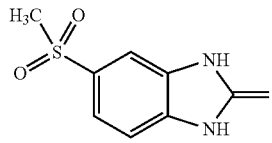 | A4 |
| 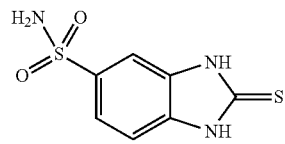 [SMILES: NS(=O)(=O)c1ccc2[nH]c(=S)[nH]c2c1] | A5 |
| 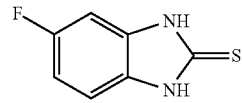 [SMILES: Fc1ccc2[nH]c(=S)[nH]c2c1] | A6 |
| 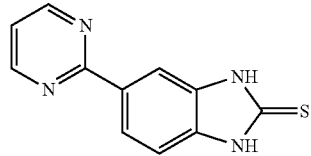 [SMILES: S=c1[nH]c2ccc(-c3ncccn3)cc2[nH]1] | A7 |
| 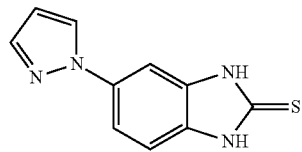 | A8 |
| 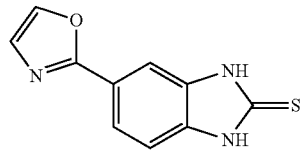 [SMILES: S=c1[nH]c2ccc(-c3ncco3)cc2[nH]1] | A9 |
| 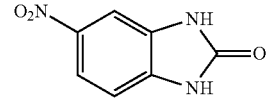 [SMILES: O=c1[nH]c2ccc([N+](=O)[O-])cc2[nH]1] | A10 |

Preparation of additional Intermediates A useful in producing the compounds of the invention, as well as commercially unavailable starting materials used to prepare certain of Intermediates A in the above table are described below.

Preparation of 2-sulfanylidene-2,3-dihydro-1H-1,3-benzodiazole-5-carboxylic acid (A/1137/5/1, Intermediate A13)

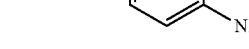

A/1137/5/1

A mixture of 3,4-diaminobenzoic acid (0.50 g, 3.29 mmol), potassium xanthogenate (0.53 g, 3.29 mmol) and AcNMe$_2$ (0.6 mL) in DMF (3 mL) was refluxed for 1.5 h then stirred at RT overnight. The mixture was filtered; the solid was washed with ethanol and dried under vacuum to give 0.62 g of Intermediate A13 (A/1137/5/1).

Preparation of Dianiline for Intermediate A7

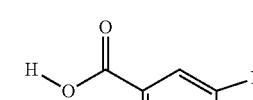
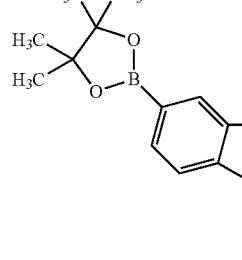
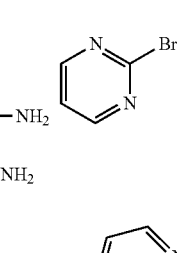
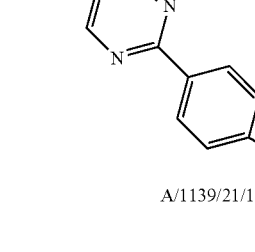

A/1139/21/1

A mixture of 4-(tetramethyl-1,3,2-dioxaborolan-2-yl)benzene-1,2-diamine (330 mg), 2-bromopyrimidine (247 mg), K$_2$CO$_3$ (585 mg) and PdCl$_2$(PPh$_3$)$_2$ (198 mg) in dioxane (9.0 mL) and water (4.5 mL) was flushed with nitrogen and shaken in a PLS apparatus at 90° C. for 4 h. The reaction mixture was partitioned between dichloromethane and water, and the organic layer was washed with brine, dried over sodium sulfate, filtered and evaporated in vacuum. The resulting residue was purified by amine-FC (Snap 25, eluting with DCM/MeOH from 100/0 to 98/2) to give 445 mg of A/1139/21/1, which was used as described previously to produce Intermediate A7.

Preparation of Dianiline for Intermediate A8

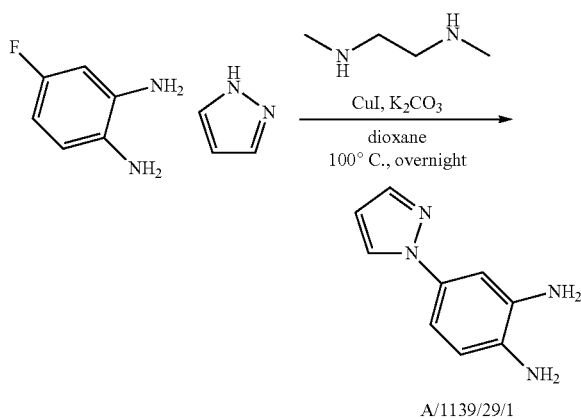

To a solution of 4-fluorobenzene-1,2-diamine (0.50 g) in dioxane (3 mL) were added potassium carbonate (1.11 g), copper iodide (0.51 g), pyrazole (0.36 g) and methyl[2-(methylamino)ethyl]amine (0.20 mL). The mixture was shaken at 100° C. overnight in a PLS apparatus. DCM and water were added to the mixture, the organic phase was washed with saturated sodium bicarbonate solution, water, dried over sodium sulfate and the solvent removed under vacuum to give 0.45 g of the crude product A/1139/29/1, which was used as described previously to produce Intermediate A8

Synthesis of Dianiline for Intermediate A9

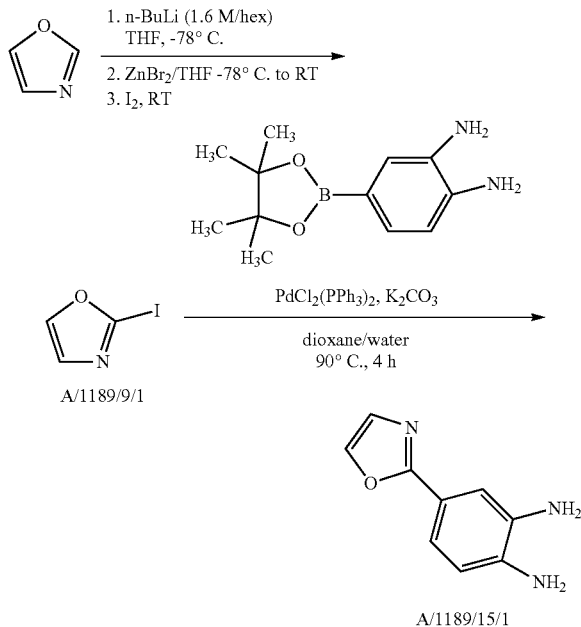

Step 1:
To a stirred solution of oxazole (0.50 g) in anhydrous THF (15 mL), at −78° C. and under a nitrogen atmosphere, 1.6M/THF of n-BuLi (5 mL) was added drop-wise over 5 min. The reaction mixture was stirred 0.5 h then a freshly prepared solution 1.13M/THF ZnBr$_2$ (7.7 mL) was added drop-wise over 5 min and the mixture was allowed to reach RT. I$_2$ (2.02 g) was added in one portion and the reaction mixture was stirred at RT for 1 h. Concentrated sodium bisulphite solution was added up till the violet colour disappeared, the mixture was extracted with EA, the organic phase was washed with water, dried under sodium sulfate and concentrated under vacuum (max water bath temperature 30° C.) to give (496 mg) the crude 2-iodo-oxazole A/1189/9/1 as light yellow oil that was used as such in Step 2.

Step 2:
A mixture of 4-(tetramethyl-1,3,2-dioxaborolan-2-yl)benzene-1,2-diamine (284 mg), A/1189/9/1 (260 mg), K$_2$CO$_3$ (502 mg) and PdCl$_2$(PPh$_3$)$_2$ (170 mg) in dioxane (8 mL) and water (4 mL) was flushed with nitrogen and shaken in a PLS apparatus at 90° C. for 4 h. The reaction mixture was partitioned between DCM and water, and the organic layer was washed with brine, dried over sodium sulfate, filtered and evaporated in vacuum. The resulting residue was purified by aminic FC (Snap 25, eluting with DCM/MeOH from 100/0 to 98/2) to give 151 mg of the product A/1189/15/1, which was used as described previously to produce Intermediate A9.

Synthesis of 5-[(tert-butyldimethylsilyl)oxy]-2,3-dihydro-1H-1,3-benzodiazole-2-thione (Intermediate A14)

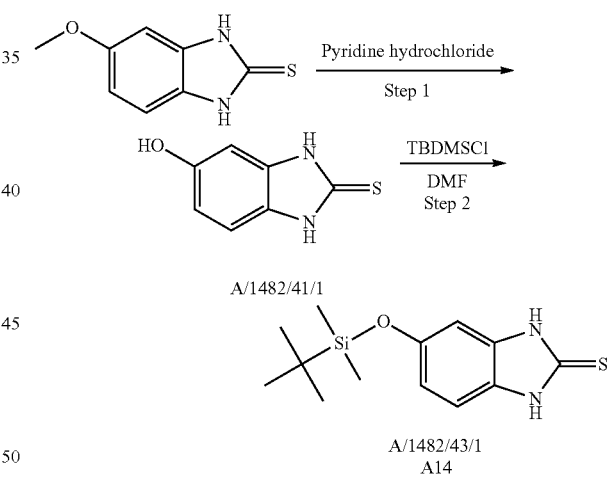

Step 1.
5-methoxy-2,3-dihydro-1H-1,3-benzodiazole-2-thione (CAS 37052-78-1) was combined with pyridine hydrochloride into a dried sealed tube, placed under N2, and stirred at 180° C. overnight. The resulting residue was dissolved in MeOH and purified by Si-column (NH) eluting with AcOEt to AcOEt/MeOH 9:1 to obtain 2.15 g of desired product 5-hydroxy-2,3-dihydro-1H-1,3-benzodiazole-2-thione (A/1482/41/1) with presence of pyridine. The product was used in the next step without further purification.

Step 2.
A solution of 5-hydroxy-2,3-dihydro-1H-1,3-benzodiazole-2-thione (A/1482/41/1), tert-butyldimethylsilyl chloride, and imidazole in DMF was stirred at RT overnight. AcOEt was added and the organic phase washed with brine. The organic phase was dried and evaporated in vacuo. The crude material was purified by Si-column (NH) eluting with DCM to afford desired product 5-[(tert-butyldimethylsilyl)oxy]-2,3-dihydro-1H-1,3-benzodiazole-2-thione.

Synthesis of Intermediate A15

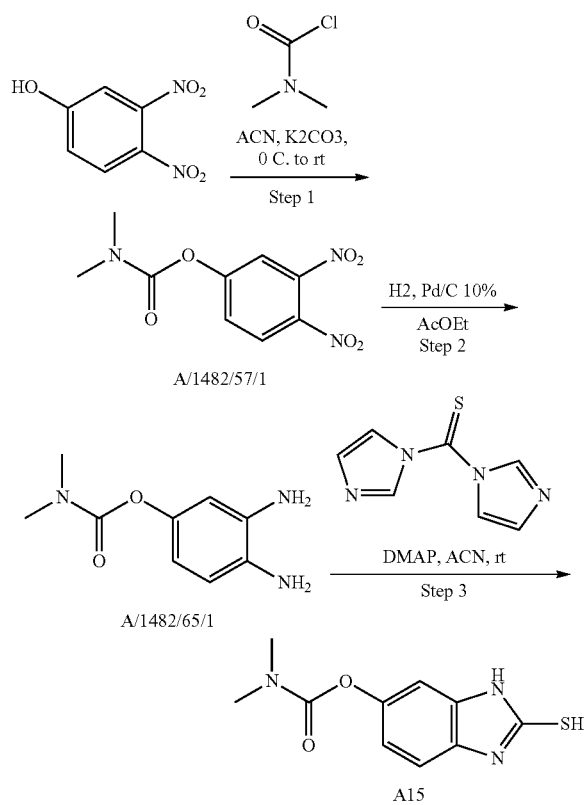

Step 1.

4-dinitrophenol (CAS 577-71-9) was dissolved in acetonitrile, potassium carbonate was added and the mixture cooled to 0° C. Dimethylcarbamoyl chloride was added dropwise, and the mixture stirred at r.t. for 1 h. UPLC analysis showed only traces of product, so the mixture was stirred at reflux overnight. The solvent was removed in vacuo, the residue dissolved in DCM and washed with brine. The organic phase separated, dried and evaporated in vacuo. The crude material was purified by Si-column to afford 1.3 g of desired product named A/1482/57/1 (Y=94%).

Step 2.

A/1482/57/1 was dissolved in AcOEt, Pd/C 10% was added and the mixture stirred at rt under hydrogen atmosphere (1 atm) overnight. The catalyst was filtered on Celite and the solvent evaporated in vacuo to obtain desired product named A/1482/65/1 (600 mg, Y=quant.)

Step 3.

To a solution of A/1482/65/1 and DMAP in MeCN (35 mL), at RT, was added a solution of 1-(1H-imidazole-1-carbothioyl)-1H-imidazole (CAS 6160-65-2) in MeCN (20 mL) and the mixture was stirred at RT for 4 h. The mixture was evaporated in vacuo, and purified by Si-column eluting with DCM to DCM/MeOH 95:5 to obtain 590 mg of Intermediate A15 (Y=83%).

Synthesis of Intermediate A16

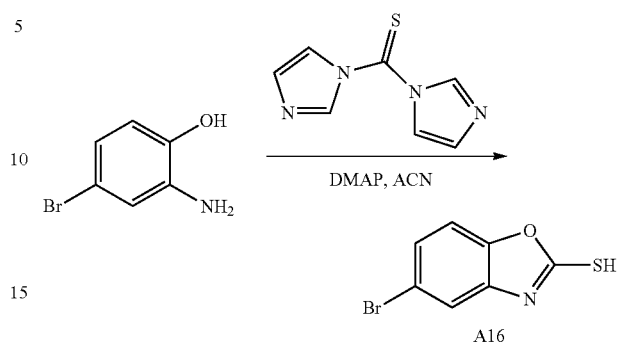

To a solution of 2-amino-4-bromophenol (CAS 40925-68-6) and DMAP in ACN (25 mL), at RT, was added 1-(1H-imidazole-1-carbothioyl)-1H-imidazole (CAS 6160-65-2) and the mixture was stirred at RT for 4 h. Then the solvent was evaporated in vacuo. The solid obtained was filtered, dissolved in DCM and washed with S. aq. NH₄Cl. The organic phase was separated and evaporated in vacuo to obtain 320 mg of Intermediate A16 with presence of DMAP.

Preparation of Intermediates B

Intermediates B have the general formula:

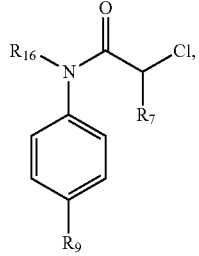

wherein $R_7$, $R_9$ and $R_{16}$ are as defined for Formulae I-VIII. An appropriately $R_9$ and $R_{16}$-containing aniline was dissolved in DCM dry (10 vol), TEA (2-3 eq) was added and the mixture was cooled to 0° C. An $R_7$-containing chloroacetyl chloride derivative (1.1 eq) was added drop-wise and the resulting mixture stirred at r.t. for 3 h. UPLC analysis showed that reaction was complete so the solvent was evaporated in vacuo, cold water was added and the precipitate collected by filtration obtaining the desired intermediates B reported in the table below:

TABLE 2

| Intermediates B | |
|---|---|
| 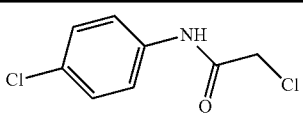 | B1 |
| 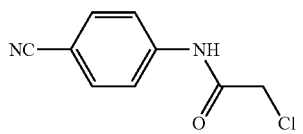 [SMILES: N#Cc1ccc(NC(=O)CCl)cc1] | B2 |

TABLE 2-continued

Intermediates B

B4: NC-C6H4-NH-C(=O)-CH(Cl)-CH3

General Experimental Procedure Combining Intermediates A and B to Produce Compounds of the Invention Intermediate A (1.2 eq.) and KOH (1.2 eq.) were dissolved in MeOH, then Intermediate B (1 eq.) was added portion-wise to the solution and the resulting reaction mixture was shaken (6 h to overnight) in a PLS apparatus at RT. When a precipitate formed, the mixture was filtered, the solid was washed with water and dried under vacuum (45° C., overnight) to give the final product. When a precipitate did not form, the reaction mixture was concentrated under reduced pressure, the crude material was taken up with DCM, the mixture was filtered, the solid was washed with DCM, water and dried under vacuum (at 45° C., overnight) to give the final product. Table 3, below, indicates the starting materials and any additional steps and/or modifications of the above protocol employed for specific compounds of the invention. Commercially available starting materials are indicated by their CAS number. The synthesis of compounds whose starting materials are indicated as "See specific chemical route" are set forth in the Examples following Table 3.

TABLE 3

Synthesis of Exemplary Compounds

| Cmpd No. | Starting Material(s) | Additional Steps and/or Modifications | MW | Amount and yield |
|---|---|---|---|---|
| 23 | 2-((6-nitro-lH-benzo[d]imidazol-2-yl)thio)-N-(4-phenoxyphenyl)acetamide (see WO2012116010) | To starting material dissolved in DMF cesium carbonate was added. MeI was added and the mixture was stirred at r.t. under $N_2$ atmosphere for 2 h. The mixture was quenched with water, the solvent was evaporated in vacuo and the crude material purified by Si-column eluting with Cy to Cy/ethyl acetate 6:4 | 434 | 45 mg 33% y |
| 56 | B2; CAS 86604-73-1 | The solid was further purified Si-column (NH) eluting with DCM to DCM/MeOH 95:5 | 376 | 77 mg 82% y |
| 57 | B2; A6 | The solid was further purified Si-column (NH) eluting with DCM to DCM/MeOH 95:5. | 326 | 86 mg 73% y |
| 93 | B2; A1 | A1 (100 mg) and B2 (93 mg) were mixed with $K_2CO_3$ (100 mg) in acetone (3 mL), was stirred at reflux for 2 h. The reaction mixture was concentrated under reduced pressure, the residue was taken up with EA and water, the organic phase was washed with water, dried over sodium sulfate and the solvent removed under vacuum. The crude product was purified by FC on silica (Snap 25, eluting with Cy/EA from 100/0 to 45/55) | 333 | 53 mg 27% y |
| 94 | B1; A1 | B1 was added at 0° C. The solid was further purified by FC on silica (Snap 25, eluting with Cy/EA from 100/0 to 55/45) | 342 | 44 mg 44% y |
| 95 | B1; CAS 97963-62-7 | | 383 | 44 mg 46% y |
| 96 | B2; A2 | | 387 | 310 mg 65% y |
| 97 | B1; A13 | the crude reaction product of the intermediates was diluted with water and 1N HCl was added up to pH ~6. The mixture was filtered and the resulting solid washed with water and dried under vacuum | 361 | 195 mg, 52% y |
| 98 | B1; A4 | further purified by FC on silica(Snap 10, eluting with Cy/EA from 100/0 to 40/60) | 395 | 73 mg 56% y |
| 99 | B1; A5 | | 396 | 101 mg 65% y |
| 100 | B1; A3 | The solid was further purified Si-column (NH) eluting with DCM to DCM/MeOH 95:5 | 318 | 32 mg 40% y |
| 101 | B1; CAS 29448-81-5 | The solid was further purified Si-column (NH) eluting with DCM to DCM/MeOH 95:5. | 318 | 47 mg 59% y |
| 102 | B2; A3 | | 309 | 76 mg 68% y |
| 103 | B2; CAS 29448-81-5 | The solid was triturated with $Et_2O$/MeOH 8:2 (3 ml). | 309 | 50 mg 45% y |
| 104 | B2; CAS 97963-62-7 | The solid was further purified Si-column (NH) eluting with DCM to DCM/MeOH 98:2. | 374 | 92 mg 68% y |
| 105 | B1; CAS 86604-73-1 | The solid was further purified Si-column (NH) eluting with DCM to DCM/MeOH 98:2 | 385 | 113 mg 75% y |
| 106 | B2; A13 | | 352 | 150 mg, 100% y |

TABLE 3-continued

Synthesis of Exemplary Compounds

| Cmpd No. | Starting Material(s) | Additional Steps and/or Modifications | MW | Amount and yield |
|---|---|---|---|---|
| 107 | B2; A4 | The solid was triturated with MeOH. | 386 | 96 mg 69% y |
| 108 | B2; A5 | The solid was triturated with MeOH. | 387 | 106 mg 76% y |
| 109 | Compound 97 | Starting material (60 mg) was stirred in DCM (1.5 mL) and MeOH (0.5 mL) was treated drop-wise with a TMSDM solution (2.0M in ether) (0.11 mL). After 30 min an additional amount of TMSDM was added (0.040 mL) and the reaction mixture was stirred at RT for 1.5 h. The mixture was filtered; the solid was washed with DCM and dried under vacuum | 375 | 28 mg 44% y |
| 110 | B1; A6 | The solid was further purified Si-column (NH) eluting with DCM to DCM/MeOH 95:5 | 335 | 92 mg 76% y |
| 111 | B4; CAS 6325-91-3 | The solid was further purified Si-column (NH) eluting with DCM to DCM/MeOH 95:5 | 367 | 44 mg 25% y |
| 112 | B2; A13 | The product of the intermediates was treated dropwise with a trimethylsilyldiazomethane solution (2.0M in ether) (0.18 mL). After stirring overnight monitoring by UPLC showed complete conversion. Ethyl acetate was added and the organic phase washed with water and brine. The organic phase was separated, dried and evaporated in vacuo. The solid was further purified Si-column (NH) eluting with DCM to DCM/MeOH 95:5. | 366 | 45 mg 44% y |
| 113 | B2; A7 | further purified by aminic FC (Snap 25, eluting with DCM/MeOH from 100/0 to 98/2) | 386 | 55 mg 41% y |
| 114 | B1; A7 | The solid was further purified by aminic FC (Snap 25, eluting with DCM/MeOH from 100/0 to 98/2). | 395 | 55 mg 43% y |
| 115 | Compound 97 | Starting material (90 mg), 2N/THF MeNH$_2$ (0.24 mL) and TEA (0.12 mL) in dry DMF (0.6 mL) was added HATU (119 mg) portion-wise and the resulting reaction mixture was stirred overnight at RT. EA and water were added to the reaction mixture, the organic phase was washed with water, dried over sodium sulfate and the solvent removed under vacuum. The crude product was triturated with EA, the solid was dried under vacuum | 374 | 33 mg 37% y |
| 116 | B1; A8 | 1.1 eq of A8 and KOH used | 383 | 55 mg 42% y |
| 117 | B2; A8 | 1.1 eq of A8 and KOH used | 374 | 81 mg 64% y |
| 118 | Compound 97 | Starting material (80 mg) in DCM (1.0 mL), containing 2 drops of DMF, oxalyl chloride (0.037 mL) was added at RT and the mixture was stirred at RT for 1.5 h then 2N/THF Me$_2$NH (0.44 mL) was added drop-wise and the resulting solution was stirred at RT. The reaction mixture was concentrated under vacuum and the crude product purified by aminic FC (Snap 25, eluting with DCM/MeOH from 100/0 to 96/4) | 388 | 35 mg 40% y |
| 119 | Compound 97 | Starting material (90 mg), 2N/THF Me$_2$NH (0.22 mL) and TEA (0.13 mL) in dry DMF (0.5 mL), HATU (129 mg) was added portion-wise and the resulting reaction mixture was shaken overnight at RT in a PLS apparatus. EA and water were added, the organic phase was washed with water, dried over sodium sulfate and the solvent removed under reduced pressure. The crude material was purified by amine FC (Snap 25, eluting with DCM/MeOH from 100/0 to 94/6) | 379 | 39 mg 40% y |
| 127 | B1; A9 | 1.0 eq of A9 and 1.3 eq of KOH used | 384 | 48 mg 61% y |
| 128 | B2; A9 | 1.0 eq of A9 and 1.3 eq of KOH used | 375 | 44 mg 56% y |
| 129 | Compound 97 | Starting material (90 mg), 2N/THF MeNH$_2$ (0.22 mL) and TEA (0.13 mL) in dry DMF (0.5 mL), HATU (129 mg) was added portion-wise and the resulting reaction mixture was | 365 | 25 mg 20% y |

TABLE 3-continued

Synthesis of Exemplary Compounds

| Cmpd No. | Starting Material(s) | Additional Steps and/or Modifications | MW | Amount and yield |
|---|---|---|---|---|
| | | shaken overnight at RT in a PLS apparatus. EA and water were added, the organic phase was washed with water, dried over sodium sulfate and the solvent removed under reduced pressure. The crude material was purified by amine FC (Snap 25, eluting with DCM/MeOH from 100/0 to 94/6) | | |
| 130 | B2; A14 | The product of the starting material was dissolved in THF dry and cooled to 0 C. TBAF 1M in THF was added dropwise and the mixture stirred at r.t. for 3 h. The mixtures were evaporated in vacuo, dissolved in ethyl acetate and washed with S. aq. $NaHCO_3$. The organic phase was separated, dried and evaporated in vacuo to obtain a crude material. The crude was purified by Si-column (NH) eluting with DCM to DCM/MeOH 95:5 | 324 | 210 mg 50% y |
| 131 | B1; A14 | the product of the intermediates was dissolved in THF dry and cooled to 0 C. TBAF 1M in THF was added dropwise and the mixture stirred at it for 3 h. The mixtures were evaporated in vacuo, dissolved in ethyl acetate and washed with S. aq. $NaHCO_3$. The organic phase was separated, dried and evaporated in vacuo to obtain a crude material. The crude was purified by Si-column (NH) eluting with DCM to DCM/MeOH 95:5 | 333 | 100 mg 41% y |
| 134 | See specific chemical route | | 344 + 36 | 27 mg 17% y |
| 135 | B2; A/15 | | 395 | 95 mg 67% y |
| 136 | B1; A15 | The solid was further purified Si-column (NH) eluting with DCM to DCM/MeOH 95:5. | 404 | 56 mg 29% y |
| 145 | B1; A2 | | 396 | 78 mg 55% y |
| 146 | 2-((6-nitro-1H-benzo[d]imidazol-2-yl)thio)-N-(4-phenoxyphenyl)acetamide (see WO2012116010) | Produced as a side product of Compound 23; separated by Si-column | 434 | 28 mg 21% y |
| 147 | B2; A16 | | 388 | 75 mg 54% y |
| 148 | See specific chemical route | | 335 | 55 mg 29% y |
| 149 | See specific chemical route | | 337 | 7 mg 10% y |
| 150 | See specific chemical route | | 346 | 15 mg 21% y |

Example 11

Synthesis of N-(4-chlorophenyl)-3-(6-nitro-1H-benzo[d]imidazol-2-yl)propanamide hydrochloride, Compound 134

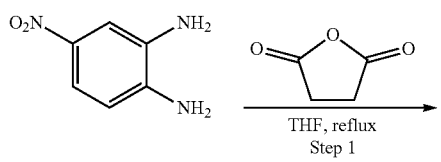

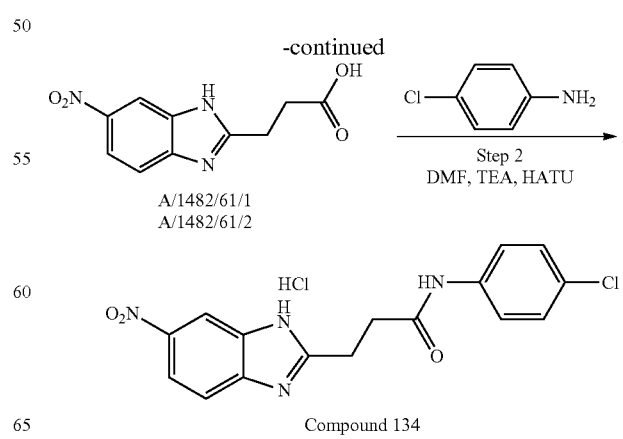

Compound 134

Step 1.

To a stirred solution of 4-nitrobenzene-1,2-diamine (CAS 99-56-9) in dioxane at room temperature, was added succinic anhydride and the reaction mixture was stirred at 90° C. for 6 days. The solvent was removed in vacuo and the crude product purified by reverse phase C18 chromatography eluting with ACN/Water 5:95 to ACN 100% to obtain two batches of the same product 3-(6-nitro-1H-1,3-benzodiazol-2-yl)propanoic acid, A/1482/61/1 (400 mg, Y=13%) and A/1482/61/2 (800 mg, Y=26%).

Step 2.

3-(6-nitro-1H-1,3-benzodiazol-2-yl)propanoic acid (A/1482/61/1) and 4-chloroaniline (CAS 106-47-8) were put in a vial, dissolved in DMF dry and TEA was added. The mixture was cooled to 0° C. and coupling reagent (HATU) was added. After stirring at r.t. overnight, UPLC analysis showed formation of intermediate C reported below:

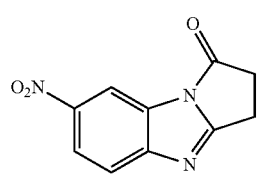

Intermediate C

The mixture was stirred at 80° C. for 5 h. UPLC analysis showed formation of product. DCM was added, and the organic phase washed with S. NaHCO$_3$ and brine. The DCM solution was evaporated in vacuo to provide crude material. The crude material was purified by Si column eluting with AcOEt to AcOEt/MeOH 9:1, providing 26 mg of impure desired product. The material was purified again by Si-column eluting with DCM to DCM/MeOH 95:5 but the product contained an unknown impurity. The material was suspended in water, acidified with HCl 1N and purified by reversed chromatography eluting with ACN/Water 5:95 to ACN 100% to obtain desired product as a hydrochloride in pure form.

Example 12

Synthesis of N-(4-cyanophenyl)-3-(6-nitro-1H-benzo[d]imidazol-2-yl)propanamide, Compound 148

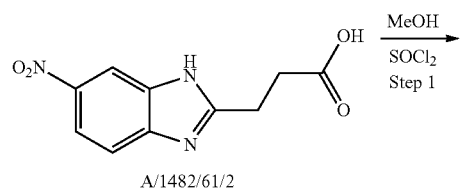

A/1482/61/2

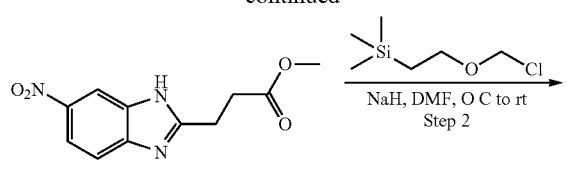

A/1540/1/1

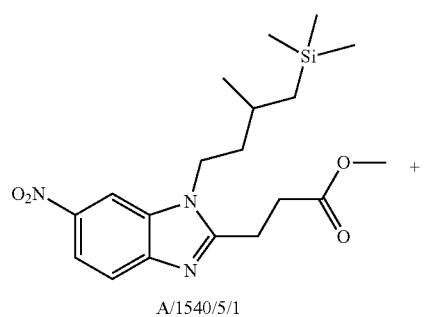

A/1540/5/1

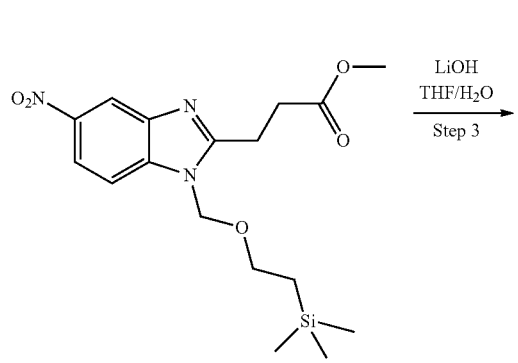

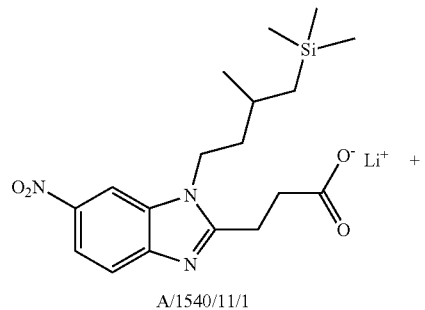

A/1540/11/1

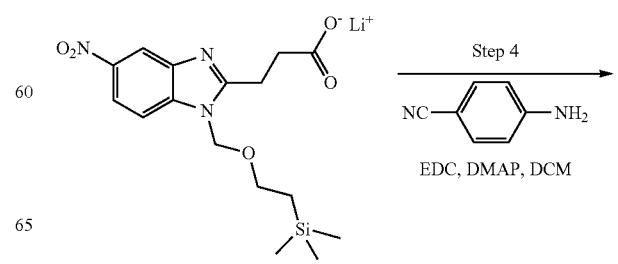

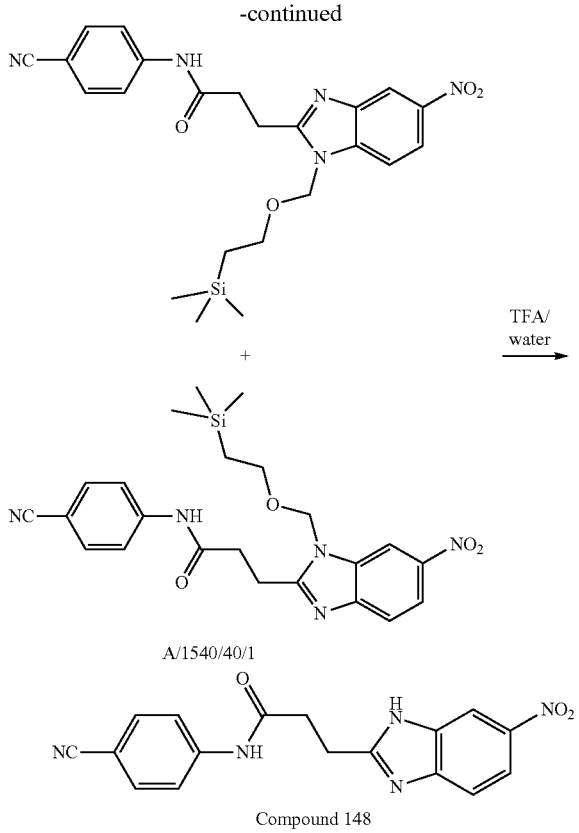

Compound 148

Step 1.

To a round bottom flask charged with methanol was added 3-(6-nitro-1H-1,3-benzodiazol-2-yl)propanoic acid A/1482/61/2 (see synthetic procedure for A/1482/63/1). This solution was cooled to 0° C., then thionyl chloride (10 eq) was added, and the reaction stirred for 5 hours. Upon completion, the reaction was evaporated in vacuo, dissolved in dichloromethane and washed three times with a saturated NaHCO$_3$ solution. The organic phase was separated, dried and evaporated in vacuo to obtain 1 g of crude material that was purified by Si-column eluting with DCM to DCM/MeOH 95:5 to provide impure desired product, methyl 3-(6-nitro-1H-1,3-benzodiazol-2-yl)propanoate (A/1540/1/1) (680 mg, Y=80%).

Step 2.

To a stirred solution of methyl 3-(6-nitro-1H-1,3-benzodiazol-2-yl)propanoate (A/1540/1/1) in DMF at 0° C. under nitrogen, NaH was added portion-wise. The ice-bath was removed, and the reaction mixture was stirred at RT. After 0.5 h the mixture was cooled to 0° C., SEMCl was added drop-wise, the ice-bath was removed and the resulting reaction mixture was stirred at RT. UPLC after 1 h showed complete conversion. EA and saturated ammonium chloride solution were added, the organic phase was washed with water, dried over sodium sulfate and the solvent removed under vacuum. The crude material was purified by FC on silica (Snap100, eluting with Cy to Cy/EA 80/20) to give 675 mg of the desired product as a mixture of region isomers named A/1540/5/1 (yellow oil, Y=65%).

Step 3.

A/1540/5/1 was dissolved in THF/Water and LiOH was added. The mixture was stirred at r.t. for 3 h. The solvent was removed in vacuo and the solid triturated with diethyl ether to obtain 670 mg of desired mix of products as lithium salt named A/1540/11/1 (Y=quant.).

Step 4.

A solution of 4-aminobenzonitrile (CAS 873-74-5) in anhydrous DCM (1 mL) was added to a mixture of A/1540/11/1, 4-dimethylaminopyridine in anhydrous DCM (2 mL). EDC was added and the mixture stirred under N$_2$ atmosphere overnight at rt. UPLC analysis showed presence of product and starting material so 1 eq of EDC was added and the mixture stirred at r.t. overnight. The mixture was diluted with DCM and washed with S. aq. NaHCO$_3$. The organic phase was evaporated in vacuo and the crude material purified by Si-column eluting with DCM to DCM/MeOH 95, providing 260 mg of desired product in pure from named A/1540/40/1 (Y=99%).

Step 5.

A/1540/40/1 was dissolved in 9:1 TFA/water. The solution was stirred at room temperature overnight. UPLC analysis showed the presence of 20% of starting material, so the mixture was heated to 50° C. and stirred for 5 h. UPLC analysis showed that reaction was complete, so the solvent was removed in vacuo. The crude material was purified by reverse phase chromatography, eluting with Water/ACN 95:5 to ACN 100% to obtain 55 mg of desired product, N-(4-cyanophenyl)-3-(6-nitro-1H-benzo[d]imidazol-2-yl)propanamide, Compound 148 (Y=29%).

Example 13

Synthesis of N-(4-cyanophenyl)-2-((6-nitro-1H-benzo[d]imidazol-2-yl)oxy)acetamide, Compound 149

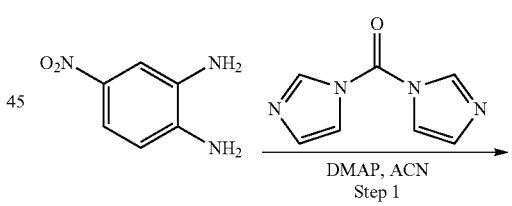

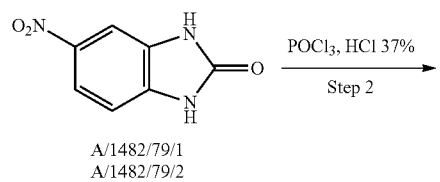

A/1482/79/1
A/1482/79/2

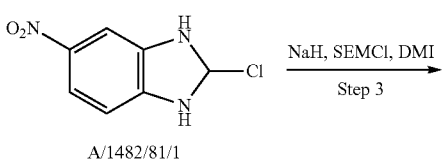

A/1482/81/1

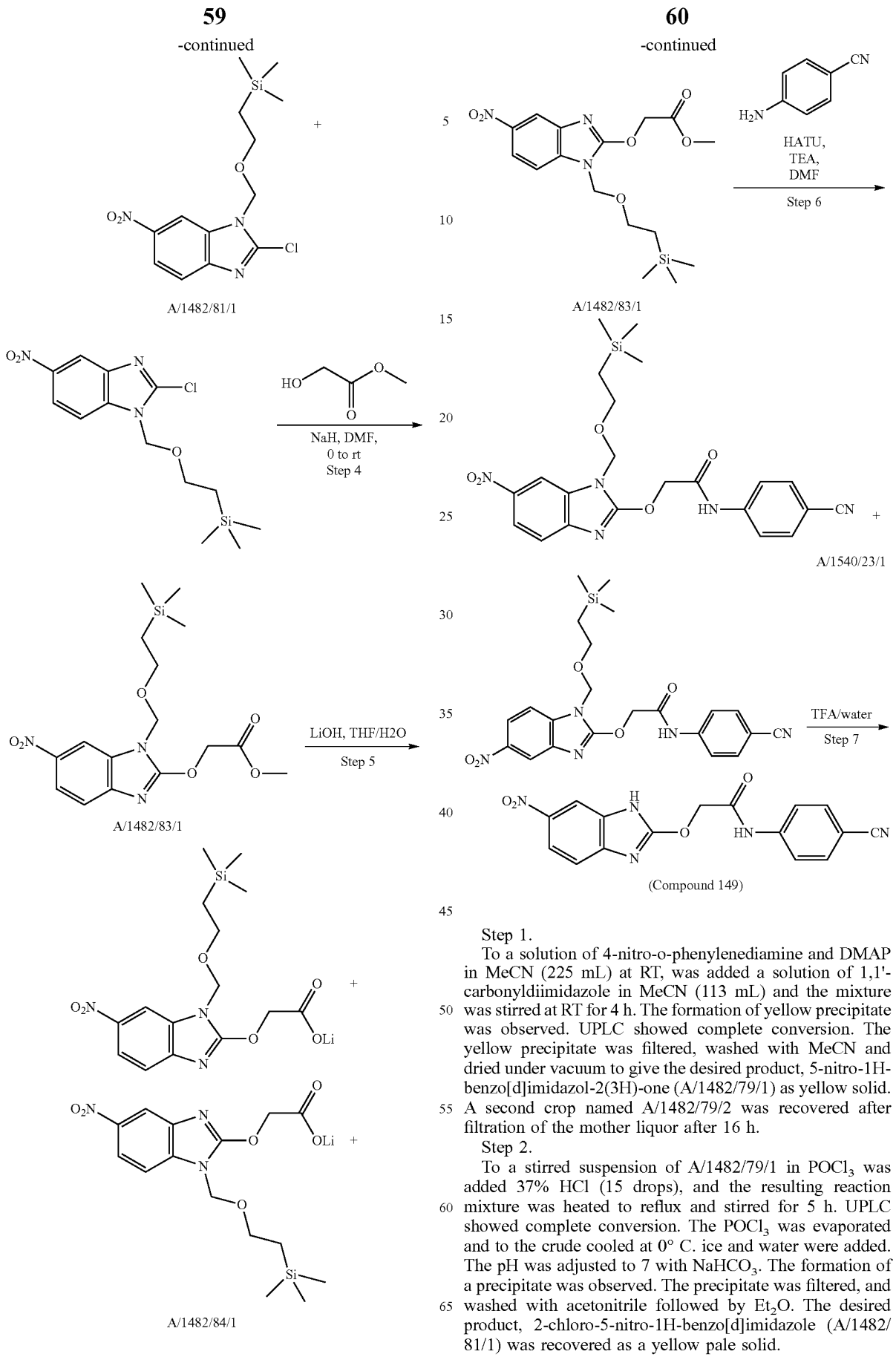

Step 1.
To a solution of 4-nitro-o-phenylenediamine and DMAP in MeCN (225 mL) at RT, was added a solution of 1,1'-carbonyldiimidazole in MeCN (113 mL) and the mixture was stirred at RT for 4 h. The formation of yellow precipitate was observed. UPLC showed complete conversion. The yellow precipitate was filtered, washed with MeCN and dried under vacuum to give the desired product, 5-nitro-1H-benzo[d]imidazol-2(3H)-one (A/1482/79/1) as yellow solid. A second crop named A/1482/79/2 was recovered after filtration of the mother liquor after 16 h.

Step 2.
To a stirred suspension of A/1482/79/1 in POCl$_3$ was added 37% HCl (15 drops), and the resulting reaction mixture was heated to reflux and stirred for 5 h. UPLC showed complete conversion. The POCl$_3$ was evaporated and to the crude cooled at 0° C. ice and water were added. The pH was adjusted to 7 with NaHCO$_3$. The formation of a precipitate was observed. The precipitate was filtered, and washed with acetonitrile followed by Et$_2$O. The desired product, 2-chloro-5-nitro-1H-benzo[d]imidazole (A/1482/81/1) was recovered as a yellow pale solid.

Step 3.

NaH (60%) in mineral oil was added portion-wise to a stirred suspension of 2-chloro-5-nitro-1H-benzo[d]imidazole (A/1482/81/1) in dry DMF at 0° C. under a nitrogen atmosphere The ice-bath was removed, and the reaction mixture was stirred at RT. After 0.5 h the mixture was cooled to 0° C., and 2-trimethylsilylethyoxymethyl chloride (0.38 mL) was added drop-wise. The ice-bath was removed, and the resulting reaction mixture was stirred at RT. After 1 h, UPLC showed complete conversion. A saturated ammonium chloride solution and EA were added, the organic phase was separated, washed with water, dried over sodium sulfate and the solvent removed under vacuum. The crude material was purified by FC on silica (Snap100, eluting with Cy/EA from 100/0 to 80/20) to give the desired product A/1482/82/1 as yellow oil.

Step 4.

To a solution of methyl glycolate in dry THF (8 ml) cooled at 0° C. was added NaH (60%) in mineral oil. The reaction was stirred at room temperature for 2 h. The suspension was cooled at 0° C. and a solution of A/1482/82/1 was added dropwise. The reaction mixture was stirred at room temperature for 16 h. UPLC showed 70% reaction completion, and another 1.1 eq of NaH was added. After stirring for 16 h, UPLC showed formation of side products. The reaction was stopped, and S. NH4Cl and EtOAC were added. The organic phase was separated, dried and evaporated to give a crude product, which was then purified by silica column (CyHex to CyHex: EtOAc=85:15). The product named A/1482/83/1 was recovered with a 50% of purity grade (by NMR), with the UPLC retention time of the impurity that same as that of the desired product.

Step 5.

To a stirred solution of the A/1482/83/1 cooled to 0° C. in THF, a solution of LiOH in water was added dropwise. The mixture was then stirred at room temperature for 2 h. UPLC showed complete conversion. The solvent was evaporated under vacuum. The residue was portioned between water and EtOAc, the organic phase was separated and discarded. The water phase was evaporated to give the desired product as the corresponding lithium salt A/1482/84/1.

Step 6.

To a stirred solution of A/1482/84/1, 4-aminobenzonitrile and TEA in THF 3:1, HATU was added at room temperature. After stirring for 5 h, UPLC showed complete conversion. The solvent was evaporated and the residue partitioned between saturated aqueous NaHCO$_3$ and DCM. The organic phase was separated, dried and the solvent evaporated to give an impure product, which was further purified by SiO$_2$ column (DCM to DCM:MeOH). The desired product named A/1540/23/1 was recovered as a white solid.

Step 7.

The SEM protected starting material A/1540/23/1 was dissolved in a mixture 9:1 TFA/water at 0° C. The solution was stirred at room temperature for 5 h. UPLC showed formation of the desired product. Excess of TFA was evaporated in vacuo and the residue was partitioned between saturated aqueous NaHCO$_3$ and DCM (3 times). The organic phases were combined, dried and the solvent evaporated to provide crude material, which was then further purified by silica column (DCM to DCM/MeOH 95:5). 15 mg of product were recovered. NMR showed a 80% of purity grade. A second purification by reverse phase chromatography was performed (water to water/MeOH 40:60) and 7 mg of the desired product, N-(4-cyanophenyl)-2-((6-nitro-1H-benzo[d]imidazol-2-yl)oxy)acetamide, was recovered (Y=10%).

Example 14

Synthesis of N-(4-chlorophenyl)-2-((6-nitro-1H-benzo[d]imidazol-2-yl)oxy)acetamide, Compound 150

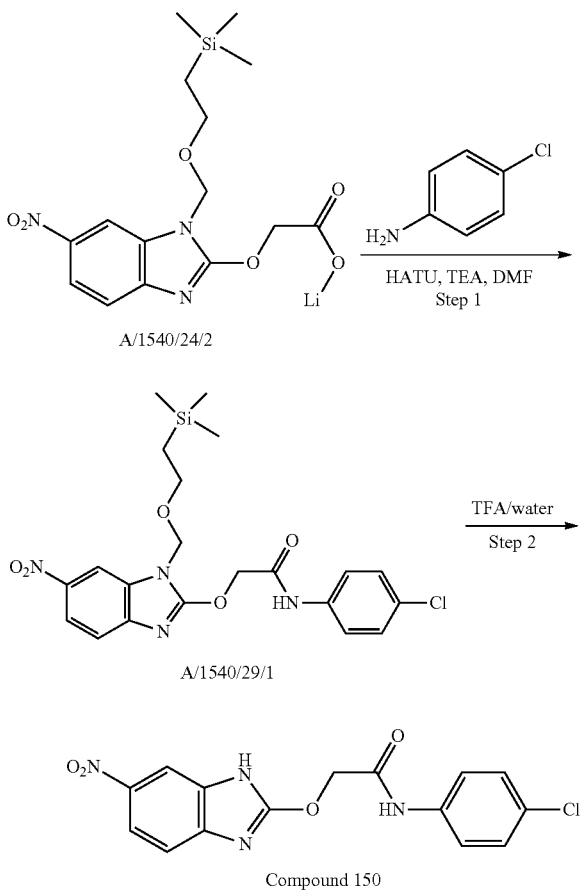

Compound 150

Step 1.

To a stirred solution of A/1540/24/2 (for synthetic procedure see A/1482/84/1), 4-chloroaniline and TEA in a mixture THF/DMF 3:1, HATU was added at room temperature. After stirring for 5 h, UPLC showed complete conversion. The solvent was evaporated, and the residue partitioned between S. aq. NaHCO$_3$ and DCM. The organic phase was separated, dried and the solvent evaporated to give crude product which was purified by silica column (DCM to DCM:MeOH 95:5). The desired product named A/1540/29/1 was recovered as a white solid.

Step 2.

A/1540/29/1 was dissolved in a mixture 9:1 TFA/water at 0° C. The solution was stirred at room temperature for 5 h. UPLC showed formation of the desired product. Excess TFA was evaporated in vacuo, and the residue was partitioned between saturated aqueous NaHCO$_3$ and DCM (3 times). Evaporation of the last two organic phases lead to the recovery of the pure desired product, N-(4-chlorophenyl)-2-((6-nitro-1H-benzo[d]imidazol-2-yl)oxy)acetamide, as a yellow solid (15 mg, Y=21%).

Example 15

Preparation of 3-(5-chloro-1H-benzo[d]imidazol-2-yl)-N-(4-(pyridin-3-yloxy)phenyl)propanamide, Compound 152

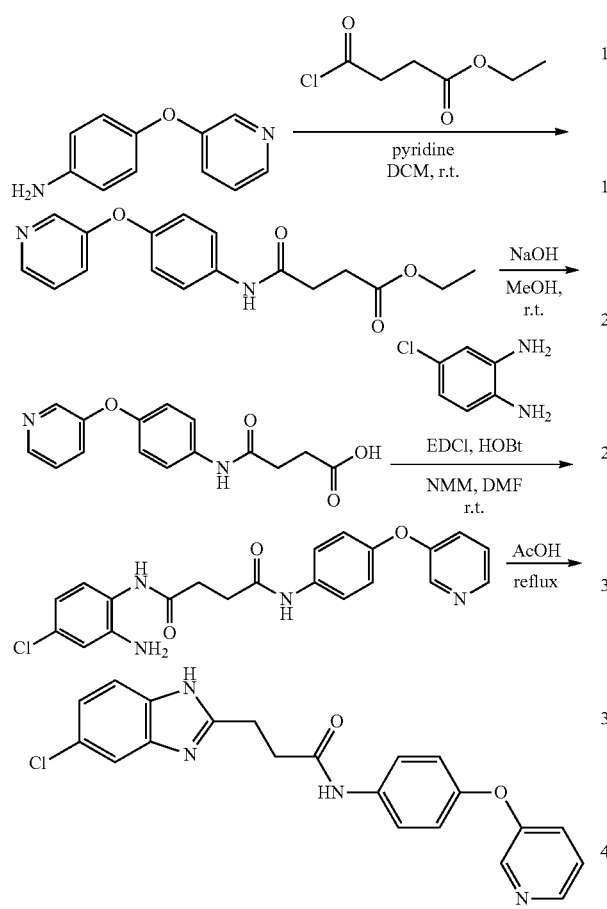

Step 1. Ethyl 4-oxo-4-(4-(pyridin-3-yloxy)phenylamino)butanoate

To a solution of 4-(pyridin-3-yloxy)aniline (1.0 g, 5.37 mmol) in anhydrous DCM (10 mL) at 0° C. were added ethyl 4-chloro-4-oxobutanoate (0.92 mL, 6.44 mmol) and pyridine (0.65 mL, 8.06 mmol). The reaction mixture was stirred at r.t. till the reaction was complete. The resulting mixture was washed in sequence with diluted HCl and brine. The organic layer was separated, dried over anhydrous Na$_2$SO$_4$ and concentrated to afford the crude product which was used directly without further purification. LC-MS: m/z 315 (M+H)$^+$.

Step 2. 4-Oxo-4-(4-(pyridin-3-yloxy)phenylamino)butanoic acid

To a solution of ethyl 4-oxo-4-(4-(pyridin-3-yloxy)phenylamino)butanoate in MeOH (10 mL) was added NaOH (0.43 g, 10.75 mmol). The reaction mixture was stirred at r.t. for 2 hr and then concentrated under reduced pressure. The residue was diluted with water, acidified to pH 2 with 6 N HCl, and filtered. The solid was collected and dried under reduced pressure to afford 4-oxo-4-(4-(pyridin-3-yloxy)phenylamino)butanoic acid (0.96 g, 62% yield over two steps). LC-MS: m/z 287 (M+H)$^+$.

Step 3. N$^1$-(2-amino-4-chlorophenyl)-N$^4$-(4-(pyridin-3-yloxy)phenyl)succinamide To a mixture of 4-chlorobenzene-1,2-diamine (100 mg, 0.7 mmol), 4-oxo-4-(4-(pyridin-3-yloxy)phenylamino)butanoic acid (200 mg, 0.7 mmol), EDCI (134 mg, 0.7 mmol), and HOBT (141 mg, 1.1 mmol) in DMF (5 mL) was added NMM (0.3 mL, 2.1 mmol). The reaction mixture was stirred at r.t. for 2 hr, then diluted with water and extracted with EtOAc. The combined organic layers were dried over anhydrous Na$_2$SO$_4$ and concentrated under reduced pressure. The residue was purified by flash column chromatography to give N$^1$-(2-amino-4-chlorophenyl)-N$^4$-(4-(pyridin-3-yloxy)phenyl)succinamide (0.25 g, 88% yield) as yellow foamy solid. LC-MS: m/z 411 (M+H)$^+$.

Step 4. 3-(5-Chloro-1H-benzo[d]imidazol-2-yl-N-(4-(pyridin-3 yloxy)phenyl)propanamide. A mixture of N$^1$-(2-amino-4-chlorophenyl)-N$^4$-(4-(pyridin-3-yloxy) phenyl)succinamide (0.25 g, 0.61 mmol) in AcOH (5 mL) was refluxed for 2 hr, then cooled down and concentrated under reduced pressure. The residue was purified by prep-HPLC to afford 3-(5-chloro-1H-benzo[d]imidazol-2-yl)-N-(4-(pyridin-3-yloxy)phenyl)propanamide (30 mg, 13% yield) as white solid. LC-MS: m/z 393 (M+H)$^+$. $^1$H NMR (400 MHz, DMSO-d$_6$) δ2.46 (s, 1H), 10.16 (s, 1H), 8.42-8.24 (m, 2H), 7.64 (d, J=9.0 Hz, 2H), 7.59-7.31 (m, 4H), 7.14 (d, J=7.1 Hz, 1H), 7.04 (d, J=8.9 Hz, 2H), 3.13 (t, J=7.2 Hz, 2H), 2.91 (t, J=7.3 Hz, 2H).

Example 16

Preparation of 2-((5-chloro-1H-benzo[d]imidazol-2-yl)thio)-N-(2-methoxy-4-(pyridin-3-yloxy)phenyl)acetamide, Compound 161

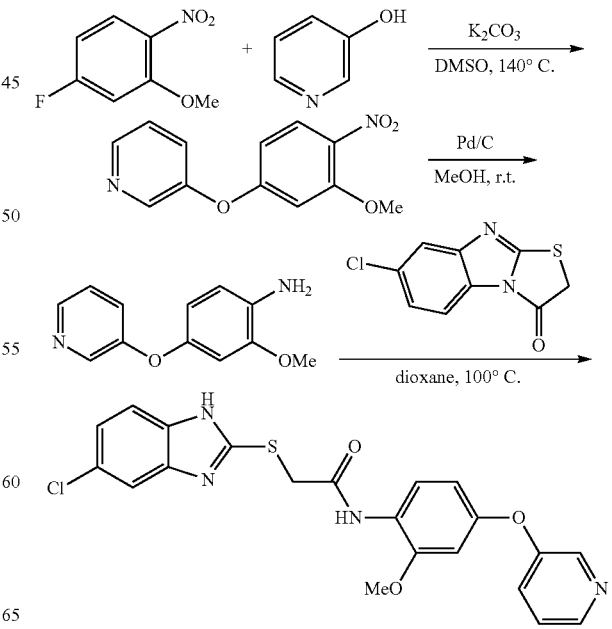

Step 1. 3-(3-Methoxy-4-nitrophenoxy)pyridine

To a solution of 4-fluoro-2-methoxy-1-nitrobenzene (1.5 g, 8.77 mmol) and pyridin-3-ol (1.08 g, 11.4 mmol) in DMSO (15 mL) was added $K_2CO_3$ (1.82 g, 13.15 mmol). The reaction mixture was stirred at 140° C. for 1 hr, and cooled to r.t. The resulting mixture was diluted with water and extracted with EtOAc. Combined organic layers were dried over anhydrous $Na_2SO_4$ and concentrated under reduced pressure. The residue was purified by flash column chromatography to give 3-(3-methoxy-4-nitrophenoxy)pyridine (1.6 g, 74% yield) as yellow solid. LC-MS: m/z 247 $(M+H)^+$.

Step 2. 2-Methoxy-4-(pyridin-3-yloxy)aniline

To a solution of 3-(3-methoxy-4-nitrophenoxy)pyridine (0.8 g, 3.25 mmol) in MeOH (8 mL) was added Pd/C power (80 mg, 10% wt). The reaction mixture was stirred at r.t. under $H_2$ atmosphere overnight. The resulting mixture was filtered through Celite. The filtrate was concentrated under reduced pressure to afford 2-methoxy-4-(pyridin-3-yloxy) aniline (0.7 g, 99% yield) as black oil which was used directly in the next step without any further purification. LC-MS: m/z 217 $(M+H)^+$.

Step 3. 2-(5-Chloro-1H-benzo[d]imidazol-2-ylthio)-N-(2-methoxy-4-(pyridin-3-yloxy)phenyl)acetamide A mixture of 2-methoxy-4-(pyridin-3-yloxy)aniline (144.4 mg, 0.67 mmol) and 7-chlorobenzo[d]thiazolo[3,2-a]imidazol-3(2H)-one (100 mg, 0.45 mmol) in dioxane was stirred at 100° C. for 1 hr. The resulting mixture was cooled to r.t. and concentrated under reduced pressure. The residue was purified by prep-HPLC to afford 2-((5-chloro-1H-benzo[d]imidazol-2-yl)thio)-N-(2-methoxy-4-(pyridin-3-yloxy)phenyl)acetamide (40.0 mg, 20% yield) as light yellow solid. LC-MS: m/z 441 $(M+H)^+$. $^1H$ NMR (400 MHz, DMSO-$d_6$) δ 12.94 (s, 1H), 9.90 (s, 1H), 8.50-8.26 (m, 2H), 8.04 (d, J=8.8 Hz, 1H), 7.61-7.44 (m, 2H), 7.44-7.33 (m, 2H), 7.18 (dd, J=8.5, 1.9 Hz, 1H), 6.85 (d, J=2.4 Hz, 1H), 6.59 (dd, J=8.8, 2.5 Hz, 1H), 4.25 (s, 2H), 3.71 (s, 3H).

The procedure set forth above was used to produce the following compounds using the appropriate starting materials.

2-((5-Chloro-1H-benzo[d]imidazol-2-yl)thio)-N-(2-hydroxy-4-(pyridin-3-yloxy)phenyl)acetamide, Compound 162

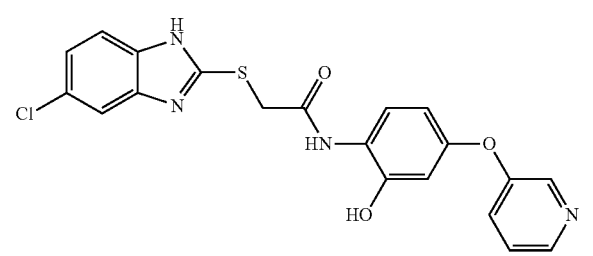 [SMILES: O=C(CSc1nc2cc(Cl)ccc2[nH]1)Nc1ccc(Oc2cccnc2)cc1Cl]

LC-MS: m/z 427 $(M+H)^+$. $^1H$ NMR (400 MHz, DMSO-$d_6$) δ 12.93 (brs, 3H), 10.18 (m, 2H), 8.34 (dd, J=6.2, 3.1 Hz, 2H), 7.96 (d, J=8.8 Hz, 1H), 7.68-7.30 (m, 4H), 7.17 (dd, J=8.5, 1.9 Hz, 1H), 6.64-6.36 (m, 2H), 4.22 (s, 2H).

2-((5-Chloro-1H-benzo[d]imidazol-2-yl)thio)-N-(2-methyl-4-(pyridin-3-yloxy)phenyl)acetamide, Compound 163

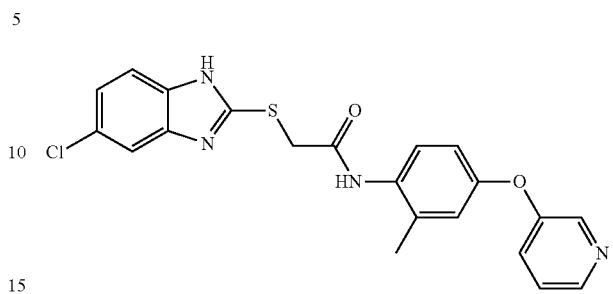

LC-MS: m/z: 425 $(M+H)^+$. $^1H$ NMR (400 MHz, DMSO-$d_6$) δ 9.84 (s, 1H), 8.38 (dd, J=7.8, 4.9 Hz, 2H), 7.54-7.42 (m, 5H), 7.17 (dd, J=8.5, 1.9 Hz, 1H), 6.98 (d, J=2.5 Hz, 1H), 6.90 (dd, J=8.6, 2.7 Hz, 1H), 4.28 (s, 2H), 2.19 (s, 3H).

2-((5-Chloro-1H-benzo[d]imidazol-2-yl)thio)-N-(2-chloro-4-(pyridin-3-yloxy)phenyl)acetamide, Compound 165

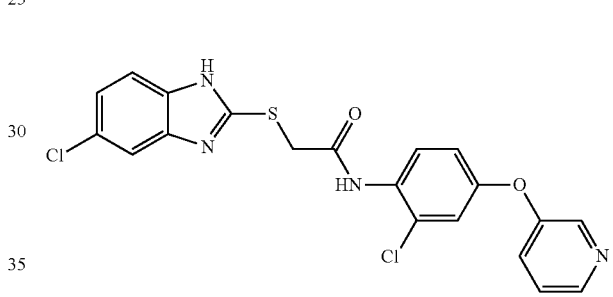

LC-MS: m/z: 445 $(M+H)^+$. $^1H$ NMR (400 MHz, DMSO-$d_6$) δ 12.92 (s, 1H), 10.20 (s, 1H), 8.48-8.33 (m, 2H), 7.87 (d, J=9.0 Hz, 1H), 7.58-7.38 (m, 4H), 7.27 (d, J=2.7 Hz, 1H), 7.17 (dd, J=8.5, 1.9 Hz, 1H), 7.06 (dd, J=9.0, 2.7 Hz, 1H), 4.28 (s, 2H).

Example 17

Preparation of N-(4-chloro-2-methylphenyl)-2-((5-cyano-1H-benzo[d]imidazol-2-yl)thio)acetamide, Compound 160

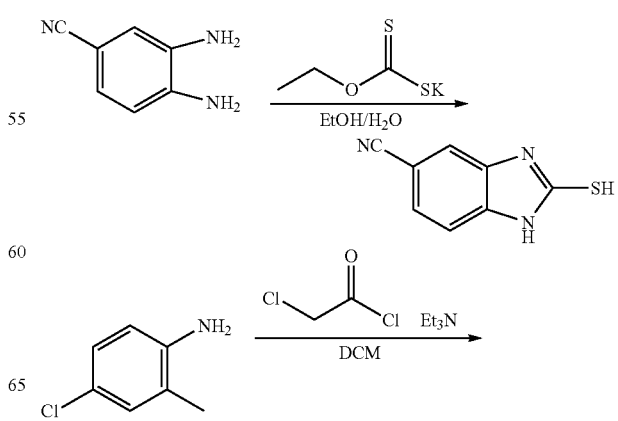

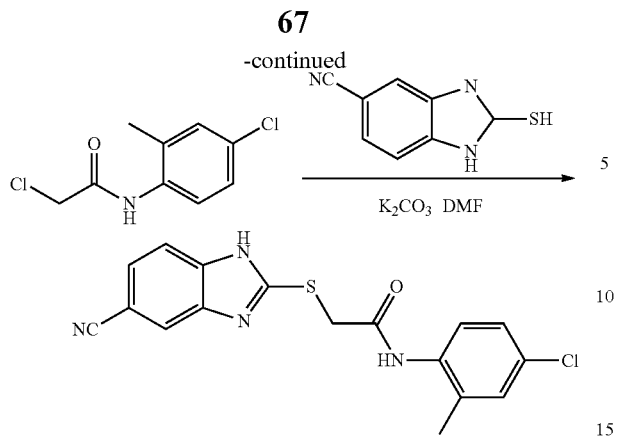

Step 1.
2-Mercapto-1H-benzo[d]imidazole-5-carbonitrile

To a suspension of 3,4-diaminobenzonitrile (1.6 g, 12 mmol) in EtOH (49 mL) and water (7 mL) was added potassium O-ethyl carbonodithioate (2.3 g, 14.4 mmol). The mixture was stirred at reflux for 4 hr followed by addition of charcoal (200 mg). The resulting mixture was refluxed for another 10 min, then cooled down to r.t. and filtered. The filtrate was concentrated under reduced pressure. The residue was suspended in water (100 mL) and filtered. The solid was collected and dried under reduced pressure to afford 2-mercapto-1H-benzo[d]imidazole-5-carbonitrile (1.2 g, 57% yield) as brown solid. LC-MS: m/z 176 (M+H)+.

Step 2.
2-Chloro-N-(4-chloro-2-methylphenyl)acetamide

To a solution of 4-chloro-2-methylaniline (284 mg, 2 mmol) in DCM (10 mL) was added Et₃N (404 mg, 4 mmol) and 2-chloroacetyl chloride (271 mg, 2.4 mmol). The reaction mixture was stirred at r.t. for 2 hr. The resulting mixture was washed with S. aq. NaHCO₃. The organic layer was separated, dried over anhydrous Na₂SO₄ and concentrated under reduced pressure to give 2-chloro-N-(4-chloro-2-methylphenyl)acetamide (380 mg, 87% yield) as a brown solid without further purification. LC-MS: m/z 218 (M+H)+.

Step 3. N-(4-chloro-2-methylphenyl)-2-((5-cyano-1H-benzo[d]imidazol-2-yl)thio)acetamide To a solution of 2-mercapto-1H-benzo[d]imidazole-5-carbonitrile (105 mg, 0.6 mmol) in DMF (6 mL) was added K₂CO₃ (166 mg, 1.2 mmol) and 2-chloro-N-(4-chloro-2-methylphenyl)acetamide (131 mg, 0.6 mmol). The reaction mixture was stirred at r.t. for 1 hr, and partitioned between aq. LiCl (10% wt) and DCM. The organic layer was separated, dried over anhydrous Na₂SO₄, and concentrated under reduced pressure. The residue was purified by prep-HPLC to give N-(4-chloro-2-methylphenyl)-2-(5-cyano-1H-benzo[d]imidazol-2-ylthio)acetamide (110 mg, 52% yield) as white solid. LC-MS: m/z 357 (M+H)+. ¹H NMR (400 MHz, DMSO-d₆) δ 9.93 (s, 1H), 7.96 (s, 1H), 7.58 (d, J=8 Hz, 1H), 7.51 (d, J=8.4 Hz, 2H), 7.29 (s, 1H), 7.21 (d, J=8.4 Hz, 1H), 4.30 (s, 2H), 2.20 (s, 3H).

The procedure set forth above was used to produce the following compounds using the appropriate starting materials.

2-((5-Cyano-1H-benzo[d]imidazol-2-yl)thio)-N-(2,4-dichlorophenyl)acetamide, Compound 167

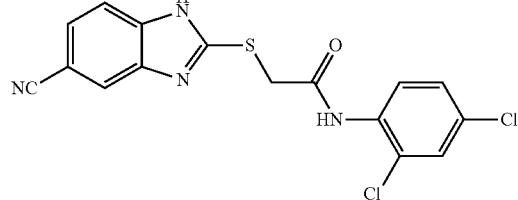

LC-MS: m/z 377 (M+H)+. ¹H NMR (400 MHz, DMSO-d₆) δ 10.29 (s, 1H), 7.98 (s, 1H), 7.90 (d, J=8.8 Hz, 1H), 7.65 (s, 1H), 7.60 (d, J=8.4 Hz, 1H), 7.53 (d, J=8 Hz, 1H), 7.41 (d, J=8.8 Hz, 1H) 4.33 (s, 2H).

2-((5-Cyano-1H-benzo[d]imidazol-2-yl)thio)-N-(2-methyl-4-(pyridin-3-yloxy)phenyl)acetamide (Compound 168)

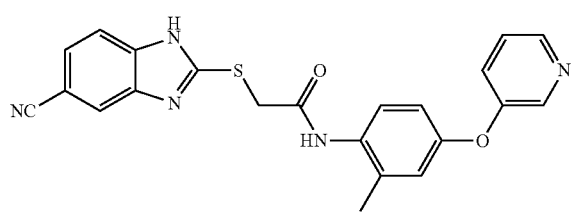 [SMILES: Cc1cc(Oc2cccnc2)ccc1NC(=O)CSc1nc2cc(C#N)ccc2[nH]1]

LC-MS: m/z 416 (M+H)+. 1H NMR (400 MHz, DMSO-d6) δ 10.12 (s, 1H), 8.33-8.35 (m, 2H), 7.92 (s, 1H), 7.48-7.57 (m, 3H), 7.39 (d, J=4.8 Hz, 2H), 6.95 (s, 1H), 6.88 (d, J=8.8 Hz, 1H) 4.26 (s, 2H) 2.19 (s, 3H).

2-((5-Cyano-1H-benzo[d]imidazol-2-yl)thio)-N-(2-methoxy-4-(pyridin-3-yloxy)phenyl)acetamide, Compound 169

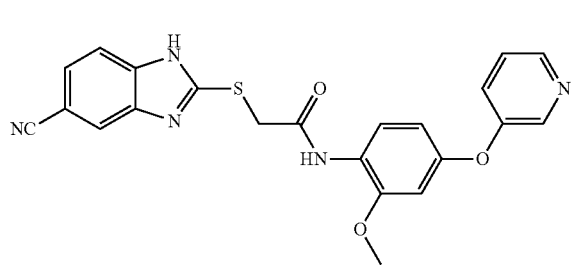 [SMILES: COc1cc(Oc2cccnc2)ccc1NC(=O)CSc1nc2cc(C#N)ccc2[nH]1]

LC-MS: m/z 432 (M+H)+. ¹H NMR (400 MHz, DMSO-d₆) δ 13.28 (s, 1H), 9.85 (s, 1H), 8.32-8.35 (m, 2H), 8.01 (d, J=8.4 Hz, 2H), 7.55-7.64 (m, 2H), 7.39 (s, 2H), 6.86 (s, 1H) 6.58 (d, J=8.8 Hz, 1H), 4.31 (s, 2H) 3.73 (s, 3H).

N-(2-chloro-4-(pyridin-3-yloxy)phenyl)-2-((5-cyano-1H-benzo[d]imidazol-2-yl)thio)acetamide, Compound 170

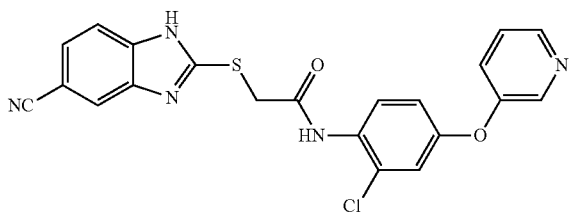 [SMILES: N#Cc1ccc2[nH]c(SCC(=O)Nc3ccc(Oc4cccnc4)cc3Cl)nc2c1]

LC-MS: m/z: 436 (M+H)+. 1H NMR (400 MHz, DMSO-d6) δ 13.27 (s, 1H), 10.12 (s, 1H), 8.39 (t, 2H), 7.99 (s, 1H), 7.81 (d, J=8.8 Hz, 1H), 7.58-7.61 (m, 1H), 7.53-7.55 (m, 1H), 7.40-7.48 (m, 2H), 7.25 (d, J=3.2 Hz, 1H), 7.04 (d, J=8.8 Hz, 1H), 4.33 (s, 2H).

Example 18

Preparation of (S)-3-(6-chloro-1H-benzo[d]imidazol-2-yl)-3-hydroxy-N-(4-(pyridin-3-yloxy)phenyl)propanamide, Compound 172

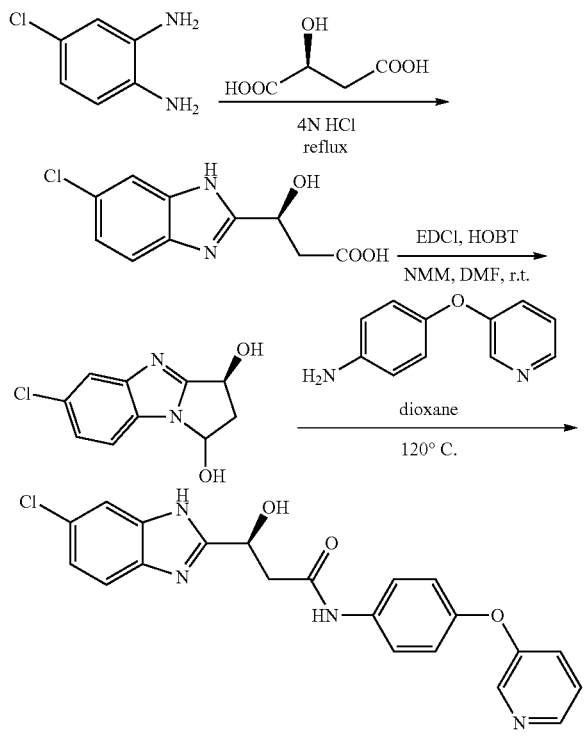

Step 1. (S)-3-(6-chloro-1H-benzo[d]imidazol-2-yl)-3-hydroxypropanoic acid

A mixture of (S)-2-hydroxysuccinic acid (4.7 g, 35.07 mmol) and 4-chlorobenzene-1,2-diamine (5.0 g, 35.07 mmol) in 4N HCl (25 mL) was refluxed overnight. The precipitate was removed by filtration. The filtrate was neutralized to pH 5 and filtered again. The solid was collected, dried, and then re-crystallized from EtOH—H2O to afford (S)-3-(6-chloro-1H-benzo[d]imidazol-2-yl)-3-hydroxypropanoic acid (6.6 g, 78% yield) as yellow solid. LC-MS: m/z 241 (M+H)+.

Step 2. (S)-6-chloro-3-hydroxy-2,3-dihydro-1H-benzo[d]pyrrolo[1,2-a]imidazol-1-one To a mixture of (S)-3-(6-chloro-1H-benzo[d]imidazol-2-yl)-3-hydroxypro-panoic acid (0.2 g, 0.83 mmol), EDCI (0.24 g, 1.25 mmol), and HOBT (0.23 g, 1.66 mmol) in DMF (4 mL) was added NMM (0.3 mL, 2.5 mmol). The reaction mixture was stirred at r.t. for 2 hr, then diluted with water and extracted with EtOAc. Combined organic layers were dried over anhydrous Na2SO4 and concentrated to give crude (S)-6-chloro-3-hydroxy-2,3-dihydro-1H-benzo[d]pyrrolo[1,2-a]imidazol-1-one as yellow solid which was used directly for the next step without further purification. LC-MS: m/z 223 (M+H)+.

Step 3. (S)-3-(6-chloro-1H-benzo[d]imidazol-2-yl)-3-hydroxy-N-(4-(pyridin-3-yloxy)phenyl)propanamide The above crude product was dissolved in dioxane (4 mL) followed by addition of 4-(pyridin-3-yloxy)aniline (231 mg, 1.25 mmol). The reaction mixture was heated to 120° C. for 4 hr and cooled to r.t. The resulting mixture was concentrated under reduced pressure and the residue was purified by prep-HPLC to afford (S)-3-(6-chloro-1H-benzo[d]imidazol-2-yl)-3-hydroxy-N-(4-(pyridin-3-yloxy)phenyl)pro-panamide (10.0 mg, 3% yield over two steps) as grey solid. LC-MS: m/z 409 (M+H)+. 1H NMR (400 MHz, DMSO-d6) δ 12.59 (s, 1H), 10.15 (s, 1H), 8.42-8.28 (m, 2H), 7.67 (d, J=9.0 Hz, 2H), 7.50 (s, 2H), 7.43-7.34 (m, 2H), 7.17 (d, J=8.5 Hz, 1H), 7.06 (d, J=9.0 Hz, 2H), 6.16 (s, 1H), 5.29 (s, 1H), 3.03 (dd, J=14.8, 4.3 Hz, 1H), 2.82 (dd, J=14.8, 8.8 Hz, 1H).

Example 19

Preparation of 2-((5-chloro-1H-benzo[d]imidazol-2-yl)amino)-N-(4-(pyridin-3-yloxy)phenyl)acetamide, Compound 159

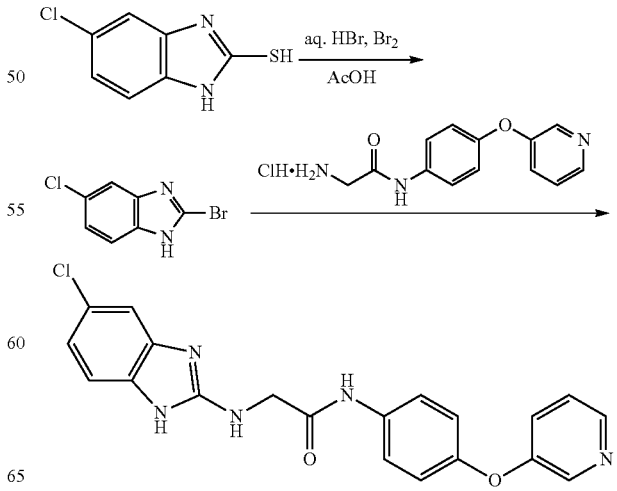

Step 1. 2-Bromo-5-chloro-1H-benzo[d]imidazole

To a solution of 5-chloro-1H-benzo[d]imidazole-2-thiol (1.84, 10 mmol) in AcOH (15 mL) at 0° C. was added dropwise HBr (aq. 48% wt, 2.5 mL) and bromine (1.3 ml, 25 mmol) over 10 min. The mixture was stirred at 0° C. for 30 min and then at r.t. for 3 hr. The resulting mixture was quenched with water and extracted with EtOAc. Combined organic layers were washed with brine, dried over anhydrous $Na_2SO_4$, and concentrated under reduced pressure. The residue was purified by column chromatography to give to 2-bromo-5-chloro-1H-benzo[d]imidazole (600 mg, 26% yield). LC-MS: m/z 231 (M+H)$^+$.

Step 2. 2-((5-chloro-1H-benzo[d]imidazol-2-yl)amino)-N-(4-(pyridin-3-yloxy)phenyl)acetamide A mixture of 2-bromo-5-chloro-1H-benzo[d]imidazole (150 mg, 0.66 mmol), 2-amino-N-(4-(pyridin-3-yloxy)phenyl)acetamide trifluoroacetate salt (224 mg, 0.66 mmol) and $Et_3N$ (0.28 mL, 2.0 mmol) in EtOH (0.5 mL) was stirred in a sealed tube at 150° C. under microwave heating for 1 hr. The resulting mixture was cooled to r.t. and then partitioned between EtOAc and $H_2O$. The organic layer was separated, washed with brine, dried over anhydrous $Na_2SO_4$ and concentrated under reduced pressure. The residue was purified by pre-HPLC to afford the desired product (80 mg, 30.7% yield) as white solid. LC-MS: m/z 394 (M+H)$^+$. $^1$H NMR (400 MHz, DMSO-$d_6$) δ 10.19 (s, 1H), 8.34 (dd, J=6.4, 3.6 Hz, 2H), 8.14 (s, 1H), 7.66 (d, J=9.0 Hz, 2H), 7.42-7.32 (m, 2H), 7.18-7.03 (m, 5H), 6.88 (d, J=7.1 Hz, 1H), 4.12 (d, J=6.1 Hz, 2H).

Example 20

Preparation of 2-((5-chloro-7-methoxy-1H-benzo[d]imidazol-2-yl)thio)-N-(4-(pyridin-3-yloxy)phenyl)acetamide, Compound 164

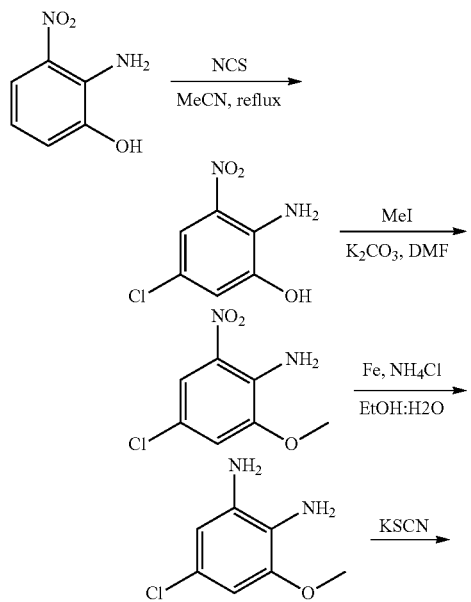

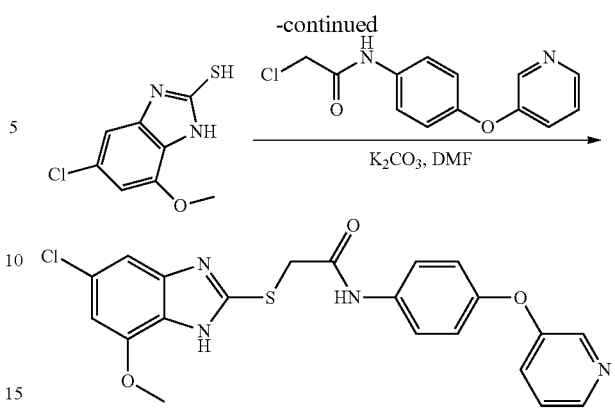

Step 1. 2-Amino-5-chloro-3-nitrophenol

To a mixture of 2-amino-3-nitrophenol (1.54 g, 10 mmol) in MeCN (20 mL) at r.t. was added NCS (1.33 g, 10 mmol). The reaction mixture was stirred at reflux for 2 hr, then cooled down to r.t. and concentrated under reduced pressure. The residue was partitioned between EtOAc (25 mL) and water (5 mL). The organic phase was separated, washed with brine (5 mL), dried over anhydrous $Na_2SO_4$, and concentrated under reduced pressure. The residue was purified by column chromatography to give 2-amino-5-chloro-3-nitrophenol (1.62 g, 86% yield) as yellow solid. LC-MS: m/z 189 (M+H)$^+$.

Step 2. 4-Chloro-2-methoxy-6-nitroaniline

To a mixture of 2-amino-5-chloro-3-nitrophenol (752 mg, 4.0 mmol) and potassium carbonate (415 mg, 3.0 mmol) in DMF was added MeI (625 mg, 4.4 mmol). The reaction mixture was stirred at r.t. for 2 hr, then quenched with water and extracted with EtOAc. Combined organic layers were washed with brine, dried over anhydrous $Na_2SO_4$ and concentrated under reduced pressure. The residue was purified by flash column chromatography to give 4-chloro-2-methoxy-6-nitroaniline (450 mg, 46.4% yield). LC-MS: m/z 203 (M−H)$^+$.

Step 3. 5-Chloro-3-methoxybenzene-1,2-diamine

A mixture of 4-chloro-2-methoxy-6-nitroaniline (1.01 g, 5 mmol), Fe (1.68 g, 30 mmol), and $NH_4Cl$ (2.67 g, 50 mmol) in EtOH (10 mL) and water (5 mL) was stirred at reflux for 4 hr and then filtered. The filtrate was concentrated under reduced pressure and the residue was purified by column chromatography to give 5-chloro-3-methoxybenzene-1,2-diamine (0.80 g, 93% yield) as brown solid. LC-MS: m/z 173 (M+H)$^+$.

Step 4. 5-Chloro-7-methoxy-1H-benzo[d]imidazole-2-thiol

To a suspension of 5-chloro-3-methoxybenzene-1,2-diamine (2.06 g, 12 mmol) in EtOH (49 mL) and water (7 mL) was added potassium O-ethyl carbonodithioate (2.3 g, 14.4 mmol). The reaction mixture was refluxed for 4 hr followed by addition of charcoal (200 mg). The resulting mixture was refluxed for another 10 min then cooled to r.t. and filtered. The filtrate was concentrated and the residue was suspended in water (100 mL). The solid was collected by filtration and dried under reduced pressure to afford 5-chloro-7-methoxy-1H-benzo[d]imidazole-2-thiol (1.6 g, 62% yield) as brown solid. LC-MS: m/z 215 (M+H)+.

Step 5. 2-(5-chloro-7-methoxy-1H-benzo[d]imidazol-2-ylthio)-N-(4-(pyridin-3-yloxy)phenyl)acetamide A mixture of 5-chloro-1H-benzo[d]imidazole-2(3H)-thione (428 mg, 2.0 mmol), 2-chloro-N-(4-(pyridin-3-yloxy)phenyl)acetamide (576 mg, 2.2 mmol), and potassium carbonate (415 mg, 3.0 mmol) in DMF was stirred at r.t. for 2 hr, then quenched with water and extracted with EtOAc. Combined organic layers were washed with brine, dried over anhydrous Na₂SO₄, and concentrated under reduced pressure. The residue was purified by prep-HPLC to afford the desired product (450 mg, 51.1% yield). LC-MS: m/z 441 (M+H)+. ¹H NMR (400 MHz, DMSO-d₆) δ 12.85 (s, 1H), 10.68 (s, 1H), 8.34 (dd, J=6.6, 3.4 Hz, 2H), 7.67-7.59 (m, 2H), 7.42-7.33 (m, 2H), 7.07 (d, J=9.9 Hz, 2H), 6.77 (s, 1H), 4.26 (d, J=4.6 Hz, 2H), 3.92 (d, J=4.6 Hz, 3H).

The procedure set forth above was used to produce the following compounds using the appropriate starting materials.

2-((5-Chloro-7-methoxy-1H-benzo[d]imidazol-2-yl)thio)-N-(4-chlorophenyl)acetamide, Compound 166

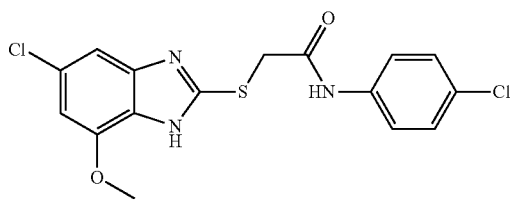 [SMILES: COc1cc(Cl)cc2nc(SCC(=O)Nc3ccc(Cl)cc3)[nH]c12]

LC-MS: m/z 382 (M+H)+. ¹H NMR (400 MHz, DMSO-d₆) δ 7.62 (d, J=8.8 Hz, 2H), 7.38 (d, J=8.8 Hz, 2H), 7.10 (s, 1H), 6.76 (s, 1H), 4.25 (s, 2H), 3.92 (s, 3H), 3.17 (d, J=5.2 Hz, 2H).

Example 21

Preparation of 2-((5-chloro-7-(2-hydroxypropan-2-yl)-1H-benzo[d]imidazol-2-yl)thio)-N-(4-(pyridin-3-yloxy)phenyl)acetamide, Compound 171

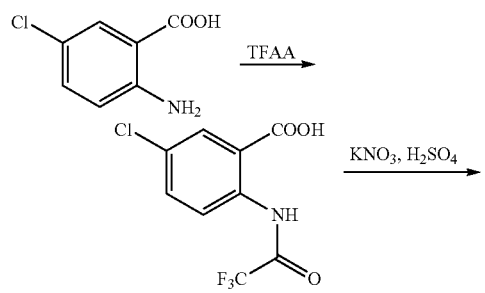

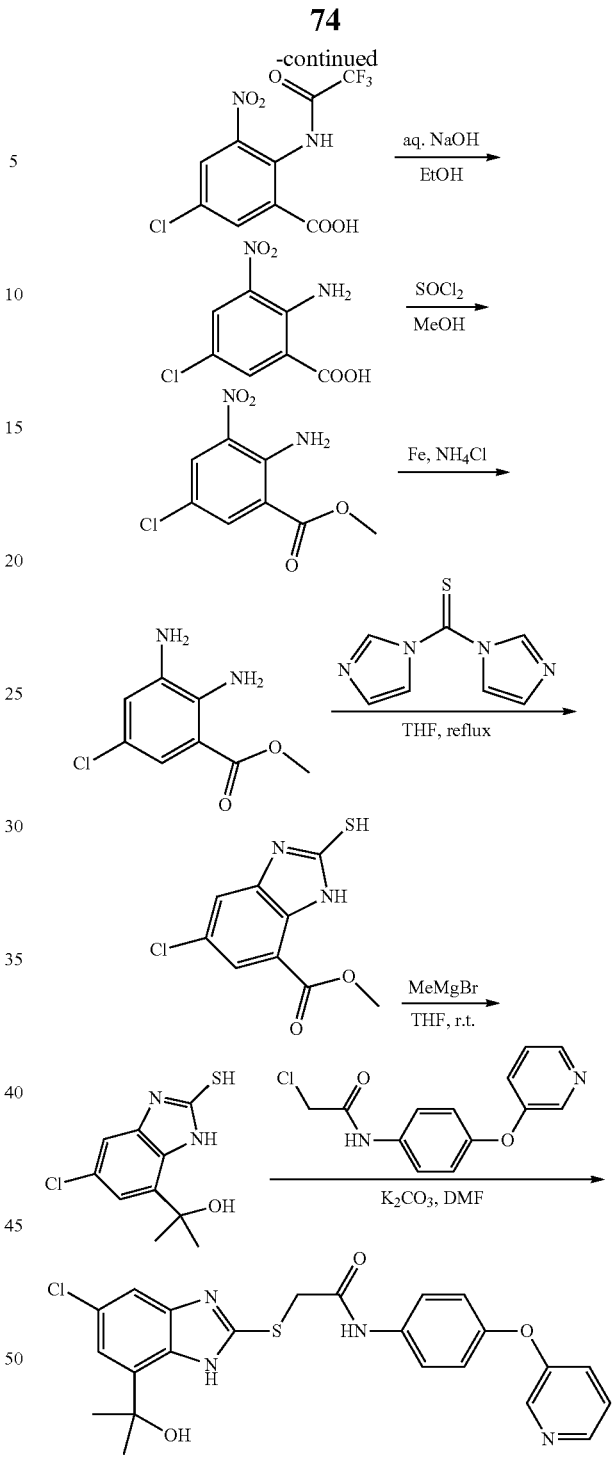

Step 1.
5-Chloro-2-(2,2,2-trifluoroacetamido)benzoic acid

To a solution of 2-amino-5-chlorobenzoic acid (1.71 g, 10 mmol) in dioxane (15 mL) at 0° C. was added dropwise TFAA (3 mL). The resulting mixture was stirred at r.t. for 3 hr, then quenched with water and extracted with EtOAc. The combined organic layers were washed with brine, dried over anhydrous Na₂SO₄, and concentrated under reduced pressure to afford 5-chloro-2-(2,2,2-trifluoroacetamido)benzoic acid (2.1 g, 78% yield) which was used directly in the next step without any further purification. LC-MS: m/z 266 (M–H)$^+$.

Step 2. 5-Chloro-3-nitro-2-(2,2,2-trifluoroacetamido)benzoic acid

To a solution of 5-chloro-2-(2,2,2-trifluoroacetamido) benzoic acid (1.33 g, 5 mmol) in H$_2$SO$_4$ (15 mL) at 0° C. was added KNO$_3$ (2.02 g, 20 mmol). The resulting mixture was stirred at r.t. for 3 hr, then poured into ice-water and extracted with EtOAc. The combined organic layers were washed with brine, dried over anhydrous Na$_2$SO$_4$ and concentrated under reduced pressure to afford 5-chloro-3-nitro-2-(2,2,2-trifluoroacetamido)benzoic acid (1.52 g, 78% yield). LC-MS: m/z 311 (M–H)$^+$.

Step 3. 2-Amino-5-chloro-3-nitrobenzoic acid

A mixture of 5-chloro-3-nitro-2-(2,2,2-trifluoroacetamido)benzoic acid (1.28 g, 4 mmol) and aq. NaOH (10% wt, 10 mL) in EtOH was heated to 80° C. for 2 hr, then quenched with water and extracted with EtOAc. The combined organic layers were dried over anhydrous Na$_2$SO$_4$ and concentrated under reduced pressure to give 2-amino-5-chloro-3-nitrobenzoic acid (0.81 mg, 94% yield) as pale yellow solid. LC-MS: m/z 215 (M–H)$^+$.

Step 4. Methyl 2-amino-5-chloro-3-nitrobenzoate

To a solution of 2-amino-5-chloro-3-nitrobenzoic acid (0.645 g, 3 mmol) in MeOH (10 mL) 0° C. was added SOCl$_2$ (0.7 g, 6 mmol). The mixture reaction was stirred at 80° C. for 12 hr, then cooled to r.t. and concentrated under reduced pressure. The residue was purified by column chromatography to give methyl 2-amino-5-chloro-3-nitrobenzoate (420 mg, 61% yield). LC-MS: m/z 231 (M+H)$^+$.

Step 5. Methyl 2,3-diamino-5-chlorobenzoate

A mixture of methyl 2-amino-5-chloro-3-nitrobenzoate (230 mg, 1 mmol), Fe (0.33 g, 6 mmol) and NH$_4$Cl (0.53 g, 10 mmol) in EtOH (9 mL) and water (3 mL) was stirred at reflux for 4 hr then filtered. The filtrate was concentrated under reduced pressure to give methyl 2,3-diamino-5-chlorobenzoate (176 mg, 87% yield) as brown solid. LC-MS: m/z 201 (M+H)$^+$.

Step 6. Methyl 5-chloro-2-mercapto-1H-benzo[d]imidazole-7-carboxylate

A mixture of methyl 2,3-diamino-5-chlorobenzoate (140 mg, 0.7 mmol), di(1H-imidazol-1-yl)methanethione (151 mg, 0.84 mmol) in THF (10 mL) was stirred at reflux for 4 hr, then cooled to r.t. and extracted with EtOAc. The combined organic layers were washed with brine, dried over anhydrous Na$_2$SO$_4$ and concentrated under reduced pressure. The residue was purified by column chromatography to give methyl 5-chloro-2-mercapto-1H-benzo[d]imidazole-7-carboxylate (130 mg, 76% yield) LC-MS: m/z 241 (M–H)$^+$.

Step 7. 2-(5-chloro-2-mercapto-1H-benzo[d]imidazol-7-yl)propan-2-ol

To a solution of methyl 5-chloro-2-mercapto-1H-benzo[d]imidazole-7-carboxylate (120 mg, 0.5 mmol) in THF (5 mL) at –10° C. was added dropwise CH$_3$MgBr (1.6 mL, 3M in THF). The resulting mixture was stirred at r.t. for 3 hr, then cooled to –10° C., quenched with water and filtered. The filtrate was extracted with EtOAc. The combined organic layers were washed with brine, dried over anhydrous Na$_2$SO$_4$ and concentrated under reduced pressure to give 2-(5-chloro-2-mercapto-1H-benzo[d]imidazol-7-yl)propan-2-ol (102 mg, 72% yield) which was used directly in the next step. LC-MS: m/z 243 (M+H)$^+$.

Step 8. 2-((5-chloro-7-(2-hydroxypropan-2-yl)-1H-benzo[d]imidazol-2-yl)thio)-N-(4-(pyridin-3-yloxy)phenyl)acetamide A mixture of 2-(5-chloro-2-mercapto-1H-benzo[d]imidazol-7-yl)propan-2-ol (48.6 mg, 0.2 mmol), 2-chloro-N-(4-(pyridin-3-yloxy)phenyl)acetamide (57.6 mg, 0.22 mmol), and potassium carbonate (41.5 mg, 0.3 mmol) in DMF was stirred at r.t. for 2 hr, then quenched with water and extracted with EtOAc. The combined organic layers were washed with brine, dried over anhydrous Na$_2$SO$_4$ and concentrated under reduced pressure. The residue was purified by prep-HPLC to afford the desired product (43 mg, 46% yield). $^1$H NMR (400 MHz, DMSO-d$_6$) δ 8.33 (d, J=4.4 Hz, 1H), 7.63 (d, J=9.0 Hz, 1H), 7.44-7.03 (m, 6H), 4.22 (s, 1H), 1.55 (s, 6H). LC-MS: m/z 469 (M+H)$^+$.

Table 4, below provides a list of compounds that are useful in the compositions and methods of the disclosure.

TABLE 4

| Exemplary Compounds | |
|---|---|
| Cpd. | Structure |
| 1 | 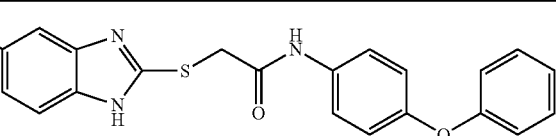 |
| 2 | 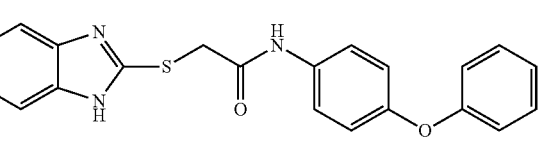 |

TABLE 4-continued
Exemplary Compounds
| Cpd. | Structure |
|---|---|
| 3 | 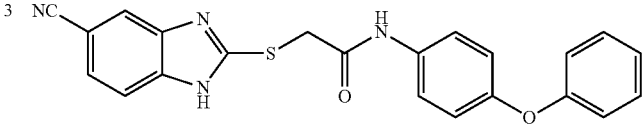 |
| 4 | 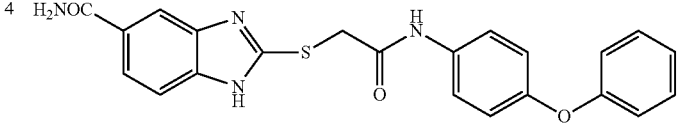 |
| 5 | 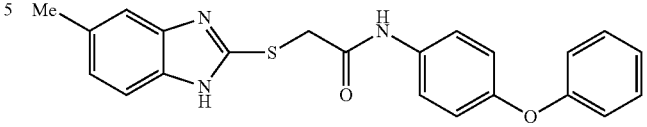 |
| 6 | 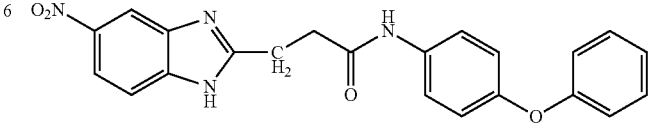 [SMILES: NC(=O)c1ccc2[nH]c(SCC(=O)Nc3ccc(Oc4ccccc4)cc3)nc2c1] |
| 7 | 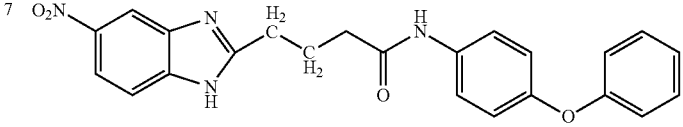 |
| 8 | 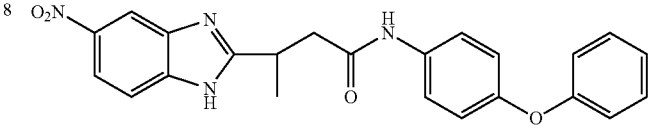 |
| 9 | 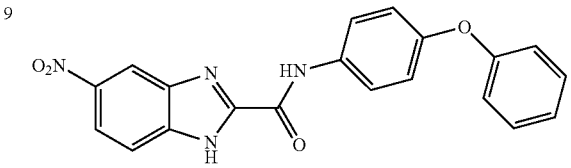 |
| 10 | 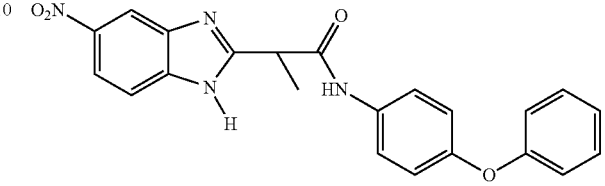 |
| 11 | 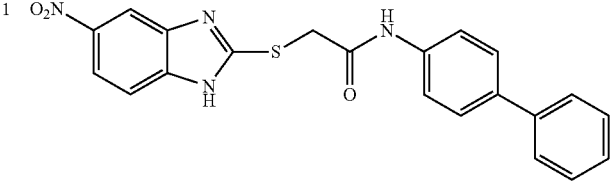 |
| 12 | 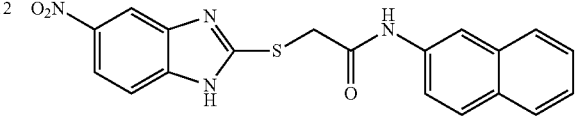 |

TABLE 4-continued

Exemplary Compounds

| Cpd. | Structure |
|---|---|
| 13 | O₂N-benzimidazole-S-CH₂-C(O)-NH-phenyl-CH₂-phenyl |
| 14 | O₂N-benzimidazole-S-CH₂-C(O)-NH-(2-pyridyl) |
| 15 | O₂N-benzimidazole-S-CH₂-C(O)-O-phenyl-O-phenyl |
| 18 | NC-benzimidazole-S-CH₂-C(O)-O-phenyl-O-phenyl |
| 19 | O₂N-benzimidazole-S-CH₂-C(O)-N(Me)-phenyl-O-phenyl |
| 20 | O₂N-benzimidazole-O-CH₂-C(O)-NH-phenyl-O-phenyl |
| 21 | O₂N-benzimidazole-NH-CH₂-C(O)-NH-phenyl-O-phenyl |
| 22 | O₂N-benzimidazole-C(O)-NH-CH₂-C(O)-NH-phenyl-O-phenyl |
| 23 | O₂N-(N-Me)benzimidazole-S-CH₂-C(O)-NH-phenyl-O-phenyl |
| 29 | O₂N-(N-Me)benzimidazole-NH-CH₂-C(O)-NH-phenyl-O-phenyl |

TABLE 4-continued

Exemplary Compounds

| Cpd. | Structure |
|---|---|
| 40 | H₂NO₂S-benzimidazole-S-CH₂-C(O)-NH-C₆H₄-O-C₆H₅ |
| 41 | MeO₂S-benzimidazole-S-CH₂-C(O)-NH-C₆H₄-O-C₆H₅ |
| 42 | imidazo[4,5-c]pyridine-S-CH₂-C(O)-NH-C₆H₄-O-C₆H₅ |
| 43 | imidazo[4,5-b]pyridine-S-CH₂-C(O)-NH-C₆H₄-O-C₆H₅ |
| 44 | benzimidazole-CF₂-CH₂-C(O)-NH-C₆H₄-O-C₆H₅ |
| 45 | benzimidazole-S(O)-CH₂-C(O)-NH-C₆H₄-O-C₆H₅ |
| 46 | benzimidazole-SO₂-CH₂-C(O)-NH-C₆H₄-O-C₆H₅ |
| 49 | O₂N-benzothiazole-S-CH₂-C(O)-NH-C₆H₄-O-C₆H₅ |
| 50 | O₂N-benzimidazole-S-CH₂-C(O)-NH-C₆H₄-O-C₆H₅ |
| 54 | H₃C-benzimidazole-S-CH₂-C(O)-NH-C₆H₄-CN |
| 55 | NC-benzimidazole-S-CH₂-C(O)-NH-C₆H₄-CN |

TABLE 4-continued

Exemplary Compounds

| Cpd. | Structure |
|---|---|
| 56 | 5-trifluoromethyl-benzimidazol-2-ylthio-CH₂-C(O)-NH-(4-cyanophenyl) |
| 57 | 5-fluoro-benzimidazol-2-ylthio-CH₂-C(O)-NH-(4-cyanophenyl) |
| 68 | 5-nitro-benzimidazol-2-ylthio-CH₂-C(O)-NH-(4-tert-butylphenyl) |
| 69 | 5-methyl-benzimidazol-2-ylthio-CH₂-C(O)-NH-(4-tert-butylphenyl) |
| 70 | 5-nitro-benzimidazol-2-yl-CH₂-NH-C(O)-(4-phenoxyphenyl) |
| 71 | 5-chloro-benzothiazol-2-yl-NH-CH₂-C(O)-NH-[4-(pyridin-3-yloxy)phenyl] |
| 72 | 5-chloro-benzothiazol-2-yl-NH-CH₂-C(O)-NH-(4-cyanophenyl) |
| 73 | 6-chloro-benzothiazol-2-yl-NH-CH₂-C(O)-NH-[4-(pyridin-3-yloxy)phenyl] |

TABLE 4-continued

Exemplary Compounds

| Cpd. | Structure |
|---|---|
| 74 | 5-chloro-benzoxazol-2-yl-NH-CH2-C(=O)-NH-(4-(pyridin-3-yloxy)phenyl) |
| 75 | 5-chloro-benzoxazol-2-yl-NH-CH2-C(=O)-NH-(4-cyanophenyl) |
| 76 | 5-chloro-1H-benzimidazol-2-yl-S-CH2-C(=O)-NH-(4-(pyridin-4-yloxy)phenyl) |
| 77 | 5-chloro-1H-benzimidazol-2-yl-S-CH2-C(=O)-NH-(4-(pyridin-3-yloxy)phenyl) |
| 78 | 5-chloro-1H-benzimidazol-2-yl-S-CH2-C(=O)-NH-(4-(pyrazin-2-yloxy)phenyl) |
| 79 | 5-chloro-1H-benzimidazol-2-yl-S-CH2-C(=O)-NH-(4-(pyrimidin-2-yloxy)phenyl) |

TABLE 4-continued

| Exemplary Compounds | |
|---|---|
| Cpd. | Structure |
| 80 | 5-chlorobenzimidazol-2-ylthio-CH₂-C(O)-NH-(4-phenyl)-O-(pyridin-3-yl with 6-methyl) |
| 81 | 5-chlorobenzimidazol-2-ylthio-CH₂-C(O)-NH-(4-phenyl)-O-(pyridin-3-yl with 5-methyl) |
| 82 | 5-chlorobenzimidazol-2-ylthio-CH₂-C(O)-NH-(4-phenyl)-O-(pyridin-3-yl with 4-methyl) |
| 83 | 5-chlorobenzimidazol-2-ylthio-CH₂-C(O)-NH-(4-phenyl)-O-(pyridin-3-yl with 2-chloro) |
| 84 | 5-chlorobenzimidazol-2-ylthio-CH₂-C(O)-NH-(4-phenyl)-O-(pyridin-3-yl with 6-chloro) |

TABLE 4-continued

Exemplary Compounds

| Cpd. | Structure |
|---|---|
| 85 | 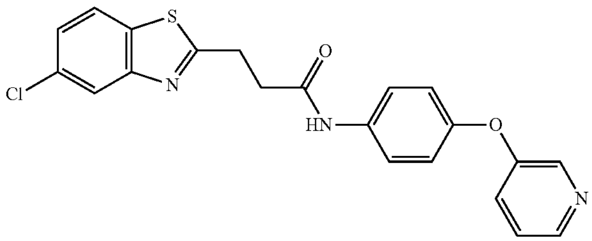 [SMILES: O=C(CCc1nc2cc(Cl)ccc2s1)Nc1ccc(Oc2cccnc2)cc1] |
| 86 | 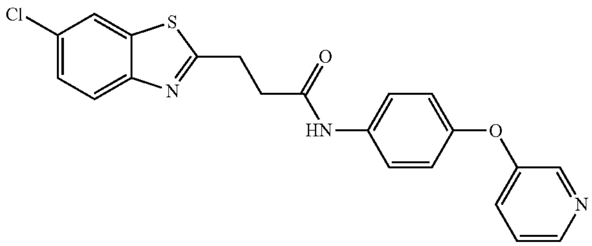 [SMILES: O=C(CCc1nc2ccc(Cl)cc2s1)Nc1ccc(Oc2cccnc2)cc1] |
| 87 | 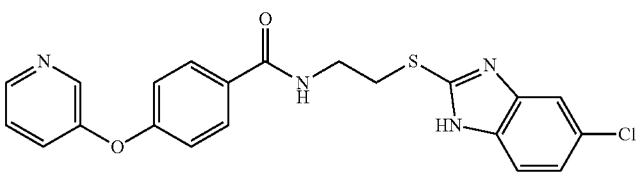 [SMILES: O=C(NCCSc1nc2cc(Cl)ccc2[nH]1)c1ccc(Oc2cccnc2)cc1] |
| 88 | 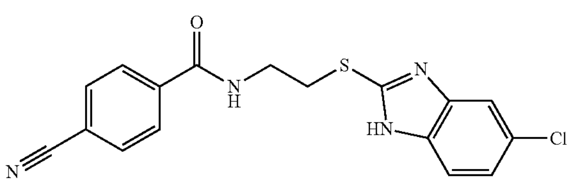 [SMILES: N#Cc1ccc(C(=O)NCCSc2nc3cc(Cl)ccc3[nH]2)cc1] |
| 89 | 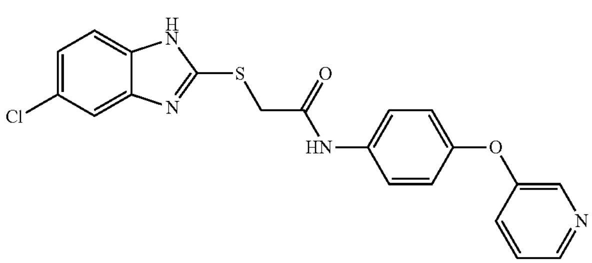 [SMILES: O=C(CSc1nc2cc(Cl)ccc2[nH]1)Nc1ccc(Oc2cccnc2)cc1] |
| 90 | 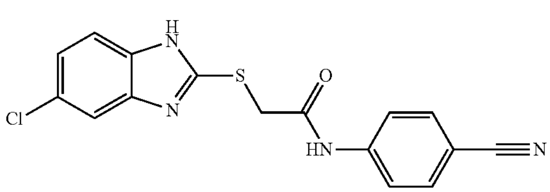 [SMILES: N#Cc1ccc(NC(=O)CSc2nc3cc(Cl)ccc3[nH]2)cc1] |

TABLE 4-continued

Exemplary Compounds

| Cpd. | Structure |
|---|---|
| 91 | (5-chloro-1H-benzimidazol-2-ylthio)methanesulfonic acid [4-(pyridin-3-yloxy)phenyl]amide |
| 92 | 3-(6-chlorobenzoxazol-2-yl)-N-[4-(pyridin-3-yloxy)phenyl]propanamide |
| 93 | 2-[(5-cyano-1H-benzimidazol-2-yl)thio]-N-(4-cyanophenyl)acetamide |
| 94 | 2-[(5-cyano-1H-benzimidazol-2-yl)thio]-N-(4-chlorophenyl)acetamide |
| 95 | 2-[(5-difluoromethoxy-1H-benzimidazol-2-yl)thio]-N-(4-chlorophenyl)acetamide |
| 96 | 2-[(5-bromo-1H-benzimidazol-2-yl)thio]-N-(4-cyanophenyl)acetamide |
| 97 | 2-{[5-carboxy-1H-benzimidazol-2-yl]thio}-N-(4-chlorophenyl)acetamide |

TABLE 4-continued

Exemplary Compounds

| Cpd. | Structure |
|---|---|
| 98 | 5-(methylsulfonyl)-1H-benzimidazol-2-yl-S-CH$_2$-C(=O)-NH-(4-chlorophenyl) |
| 99 | 5-sulfamoyl-1H-benzimidazol-2-yl-S-CH$_2$-C(=O)-NH-(4-chlorophenyl) |
| 100 | 3H-imidazo[4,5-c]pyridin-2-yl-S-CH$_2$-C(=O)-NH-(4-chlorophenyl) |
| 101 | 3H-imidazo[4,5-b]pyridin-2-yl-S-CH$_2$-C(=O)-NH-(4-chlorophenyl) |
| 102 | 3H-imidazo[4,5-c]pyridin-2-yl-S-CH$_2$-C(=O)-NH-(4-cyanophenyl) |
| 103 | 3H-imidazo[4,5-b]pyridin-2-yl-S-CH$_2$-C(=O)-NH-(4-cyanophenyl) |
| 104 | 5-(difluoromethoxy)-1H-benzimidazol-2-yl-S-CH$_2$-C(=O)-NH-(4-cyanophenyl) |
| 105 | 5-(trifluoromethyl)-1H-benzimidazol-2-yl-S-CH$_2$-C(=O)-NH-(4-chlorophenyl) |

TABLE 4-continued

Exemplary Compounds

| Cpd. | Structure |
|---|---|
| 106 | benzimidazole-5-carboxylic acid, 2-[[2-[(4-cyanophenyl)amino]-2-oxoethyl]thio]- |
| 107 | 5-(methylsulfonyl)-2-[[2-[(4-cyanophenyl)amino]-2-oxoethyl]thio]-1H-benzimidazole |
| 108 | 5-sulfamoyl-2-[[2-[(4-cyanophenyl)amino]-2-oxoethyl]thio]-1H-benzimidazole |
| 109 | methyl 2-[[2-[(4-chlorophenyl)amino]-2-oxoethyl]thio]-1H-benzimidazole-5-carboxylate |
| 110 | 5-fluoro-2-[[2-[(4-chlorophenyl)amino]-2-oxoethyl]thio]-1H-benzimidazole |
| 111 | 5-nitro-2-[[1-[(4-cyanophenyl)amino]-1-oxopropan-2-yl]thio]-1H-benzimidazole |
| 112 | methyl 2-[[2-[(4-cyanophenyl)amino]-2-oxoethyl]thio]-1H-benzimidazole-5-carboxylate |
| 113 | 5-(pyrimidin-2-yl)-2-[[2-[(4-cyanophenyl)amino]-2-oxoethyl]thio]-1H-benzimidazole |

TABLE 4-continued

Exemplary Compounds

| Cpd. | Structure |
|---|---|
| 114 | [pyrimidin-2-yl-benzimidazole-S-CH2-C(=O)-NH-(4-chlorophenyl)] |
| 115 | [N-methyl-carboxamide-benzimidazole-S-CH2-C(=O)-NH-(4-chlorophenyl)] |
| 116 | [pyrazol-1-yl-benzimidazole-S-CH2-C(=O)-NH-(4-chlorophenyl)] |
| 117 | [pyrazol-1-yl-benzimidazole-S-CH2-C(=O)-NH-(4-cyanophenyl)] |
| 118 | [N,N-dimethyl-carboxamide-benzimidazole-S-CH2-C(=O)-NH-(4-chlorophenyl)] |
| 119 | [N,N-dimethyl-carboxamide-benzimidazole-S-CH2-C(=O)-NH-(4-cyanophenyl)] |
| 120 | [chloro-benzimidazole-S-CH(CH3)-C(=O)-NH-(4-methylphenyl)] |

TABLE 4-continued

Exemplary Compounds

| Cpd. | Structure |
|---|---|
| 121 | 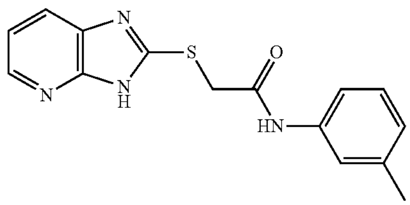 [SMILES: Cc1cccc(NC(=O)CSc2nc3cccnc3[nH]2)c1] |
| 122 | 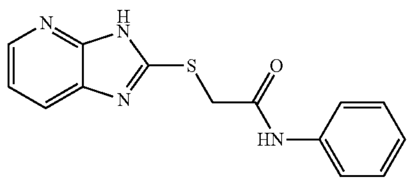 [SMILES: O=C(CSc1nc2cccnc2[nH]1)Nc1ccccc1] |
| 123 | 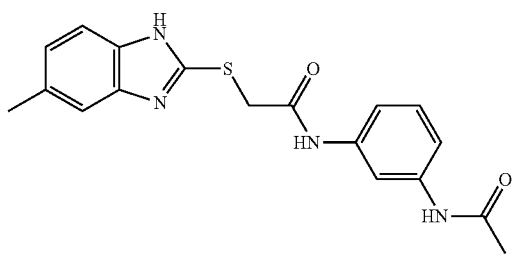 [SMILES: CC(=O)Nc1cccc(NC(=O)CSc2nc3cc(C)ccc3[nH]2)c1] |
| 124 | 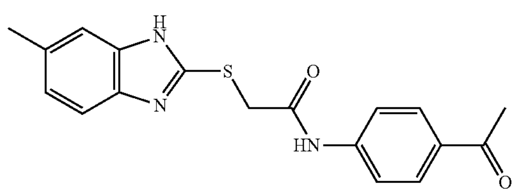 [SMILES: CC(=O)c1ccc(NC(=O)CSc2nc3ccc(C)cc3[nH]2)cc1] |
| 125 | 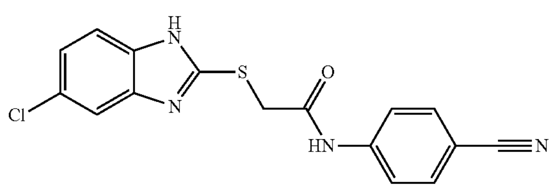 [SMILES: N#Cc1ccc(NC(=O)CSc2nc3cc(Cl)ccc3[nH]2)cc1] |
| 126 | 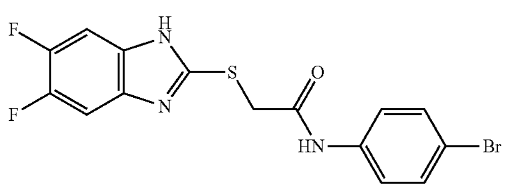 [SMILES: O=C(CSc1nc2cc(F)c(F)cc2[nH]1)Nc1ccc(Br)cc1] |
| 127 | 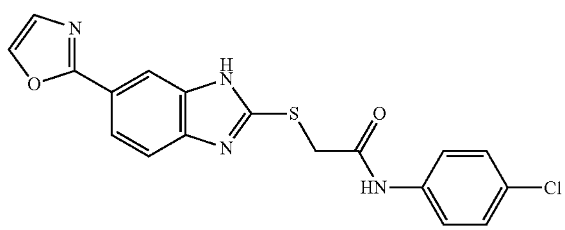 [SMILES: O=C(CSc1nc2ccc(-c3ncco3)cc2[nH]1)Nc1ccc(Cl)cc1] |

TABLE 4-continued

Exemplary Compounds

| Cpd. | Structure |
|---|---|
| 128 | (oxazol-2-yl)-benzimidazole-S-CH2-C(O)-NH-(4-cyanophenyl) |
| 129 | (N-methylcarbamoyl)-benzimidazole-S-CH2-C(O)-NH-(4-cyanophenyl) |
| 130 | (5-hydroxy)-benzimidazole-S-CH2-C(O)-NH-(4-cyanophenyl) |
| 131 | (5-hydroxy)-benzimidazole-S-CH2-C(O)-NH-(4-chlorophenyl) |
| 132 | imidazo[4,5-c]pyridine-S-CH2-C(O)-NH-(2-fluorophenyl) |
| 133 | imidazo[4,5-b]pyridine-S-CH2-C(O)-NH-(4-methylphenyl) |
| 134 | (5-nitro)-benzimidazole-CH2CH2-C(O)-NH-(4-chlorophenyl) |
| 135 | (5-(dimethylcarbamoyloxy))-benzimidazole-S-CH2-C(O)-NH-(4-cyanophenyl) |

TABLE 4-continued
Exemplary Compounds
| Cpd. | Structure |
|---|---|
| 136 | 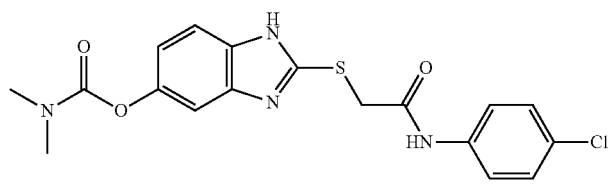 [SMILES: CN(C)C(=O)Oc1ccc2[nH]c(SCC(=O)Nc3ccc(Cl)cc3)nc2c1] |
| 137 | 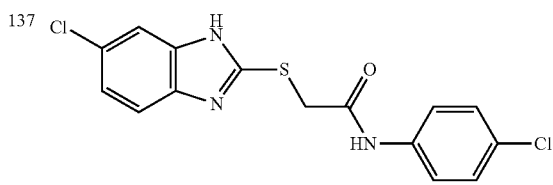 |
| 138 | 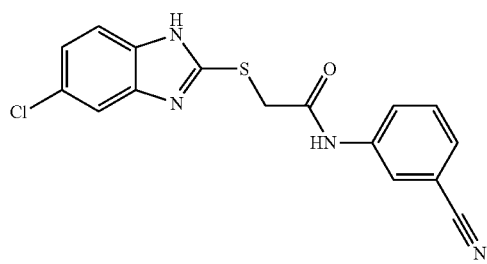 [SMILES: N#Cc1cccc(NC(=O)CSc2nc3cc(Cl)ccc3[nH]2)c1] |
| 139 | 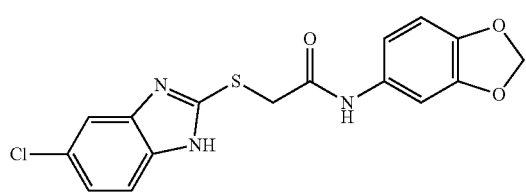 [SMILES: O=C(CSc1nc2cc(Cl)ccc2[nH]1)Nc1ccc2c(c1)OCO2] |
| 140 | 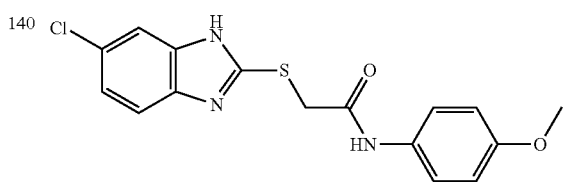 |
| 141 | 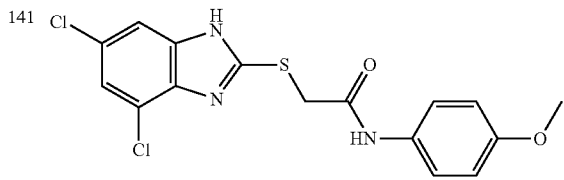 |
| 142 | 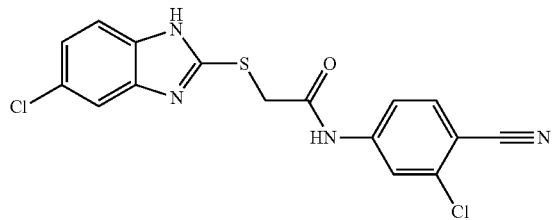 [SMILES: N#Cc1ccc(NC(=O)CSc2nc3cc(Cl)ccc3[nH]2)cc1Cl] |

TABLE 4-continued

Exemplary Compounds

| Cpd. | Structure |
|---|---|
| 143 | 5-chloro-1H-benzimidazol-2-yl-S-CH₂-C(O)-NH-(3-chloro-4-methoxyphenyl) |
| 144 | 5-chloro-1H-benzimidazol-2-yl-S-CH₂-C(O)-NH-(2,4-difluorophenyl) |
| 145 | 5-bromo-1H-benzimidazol-2-yl-S-CH₂-C(O)-NH-(4-chlorophenyl) |
| 146 | 6-nitro-1-methyl-1H-benzimidazol-2-yl-S-CH₂-C(O)-NH-(4-phenoxyphenyl) |
| 147 | 5-bromo-benzoxazol-2-yl-S-CH₂-C(O)-NH-(4-cyanophenyl) |
| 148 | 6-nitro-1H-benzimidazol-2-yl-CH₂CH₂-C(O)-NH-(4-cyanophenyl) |
| 149 | 6-nitro-1H-benzimidazol-2-yl-O-CH₂-C(O)-NH-(4-cyanophenyl) |

107
TABLE 4-continued
Exemplary Compounds
Cpd. Structure
150
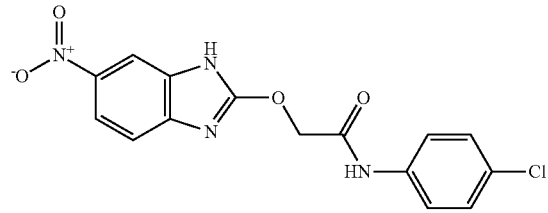
151
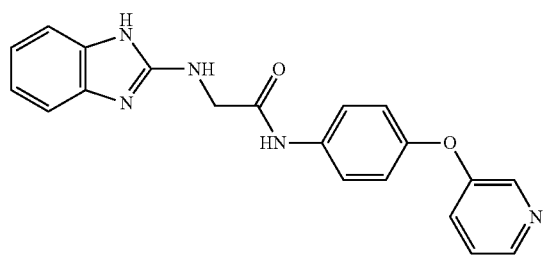 [SMILES: O=C(CNc1nc2ccccc2[nH]1)Nc1ccc(Oc2cccnc2)cc1]
152
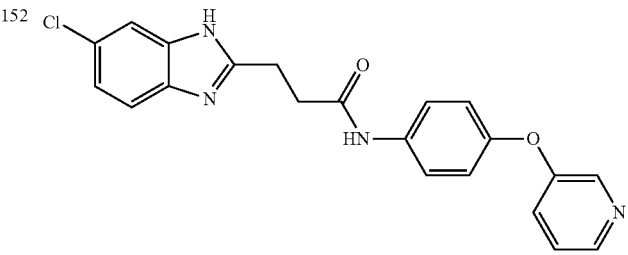
153
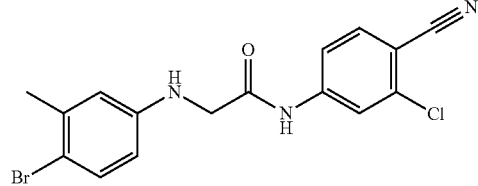 [SMILES: Cc1cc(NCC(=O)Nc2ccc(C#N)c(Cl)c2)ccc1Br]
154
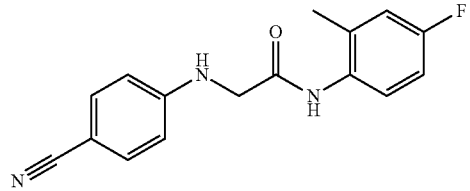 [SMILES: Cc1cc(F)ccc1NC(=O)CNc1ccc(C#N)cc1]
155
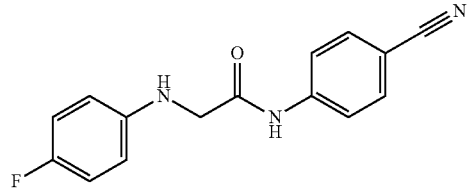 [SMILES: N#Cc1ccc(NC(=O)CNc2ccc(F)cc2)cc1]

TABLE 4-continued

Exemplary Compounds

| Cpd. | Structure |
|---|---|
| 156 | 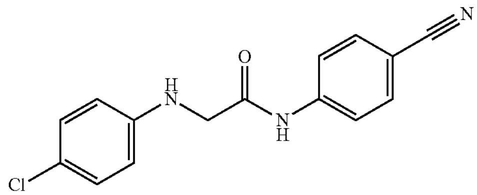 [SMILES: N#Cc1ccc(NC(=O)CNc2ccc(Cl)cc2)cc1] |
| 157 | 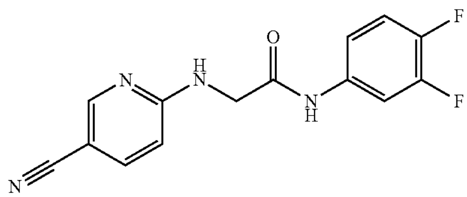 [SMILES: N#Cc1ccc(NCC(=O)Nc2ccc(F)c(F)c2)nc1] |
| 158 | 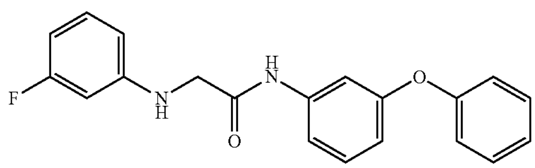 [SMILES: O=C(CNc1cccc(F)c1)Nc1cccc(Oc2ccccc2)c1] |
| 159 | 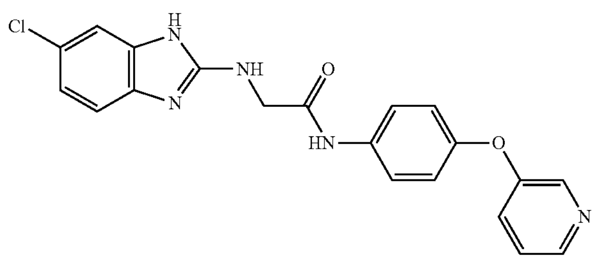 [SMILES: O=C(CNc1nc2ccc(Cl)cc2[nH]1)Nc1ccc(Oc2cccnc2)cc1] |
| 160 | 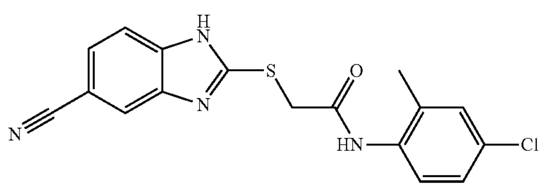 [SMILES: Cc1cc(Cl)ccc1NC(=O)CSc1nc2cc(C#N)ccc2[nH]1] |
| 161 | 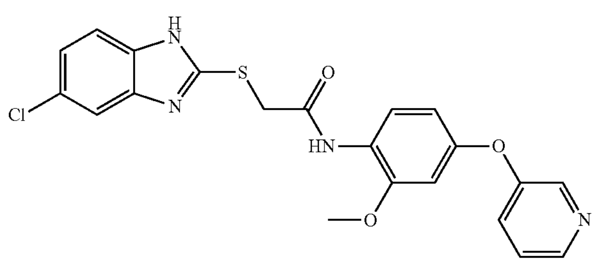 [SMILES: COc1cc(Oc2cccnc2)ccc1NC(=O)CSc1nc2cc(Cl)ccc2[nH]1] |
| 162 | 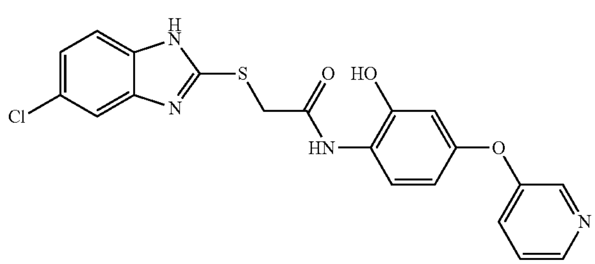 [SMILES: O=C(CSc1nc2cc(Cl)ccc2[nH]1)Nc1ccc(Oc2cccnc2)cc1O] |

TABLE 4-continued

Exemplary Compounds

| Cpd. | Structure |
|---|---|
| 163 | 5-chloro-benzimidazol-2-ylthio-CH2-C(O)-NH-(2-methyl-4-(pyridin-3-yloxy)phenyl) |
| 164 | 4-methoxy-6-chloro-benzimidazol-2-ylthio-CH2-C(O)-NH-(4-(pyridin-3-yloxy)phenyl) |
| 165 | 5-chloro-benzimidazol-2-ylthio-CH2-C(O)-NH-(2-chloro-4-(pyridin-3-yloxy)phenyl) |
| 166 | 4-methoxy-6-chloro-benzimidazol-2-ylthio-CH2-C(O)-NH-(4-chlorophenyl) |
| 167 | 5-cyano-benzimidazol-2-ylthio-CH2-C(O)-NH-(2,4-dichlorophenyl) |
| 168 | 5-cyano-benzimidazol-2-ylthio-CH2-C(O)-NH-(2-methyl-4-(pyridin-3-yloxy)phenyl) |

TABLE 4-continued

Exemplary Compounds

| Cpd. | Structure |
|---|---|
| 169 | [structure] |
| 170 | [structure] |
| 171 | [structure] |
| 172 | [structure] |

Example 22

Pyocyanin Inhibition Assay

Test compounds are dissolved in DMSO at 10 mM and stored at −20° C. until needed. Seven test concentrations from 0.0032 micromolar to 31.6 micromolar are used for each compound.

*P. aeruginosa*, strain PA14, is inoculated into 5 mL of LB broth in a 15-mL sterile glass culture tube and incubated overnight at 37° C. under shaking (~240 rpm). The overnight culture is then diluted in LB Broth to give an $OD_{600}$=0.04 ($T_0$ culture). Colony Forming Units (CFU)/mL of the overnight culture and $T_0$ culture are determined by a series of 1:10 serial dilutions in sterile saline. 4×20 μL of each dilution is seeded on LB agar plates and incubated at 35±2° C. for 20 hours. CFU/mL is determined from the dilution that gives 2 to 50 colonies/20 μL.

For concentration response curve (CRC) experiments, internal standard, 2-((5-nitro-1H-indol-2-yl)thio)-N-(4-phenoxyphenyl)acetamide, a compound previously identified as an MvfR inhibitor (see Example 1 of US 2014-0066454 (WO 2012/116010)), and test compounds are serially diluted in DMSO to 200 times each final concentration (0.5% DMSO fmal), and 1 μL/well is dispensed in duplicate into 2 mL wells of a 96-well deep well plate. 200 μL/well of $T_0$ culture are added to each internal standard/test compound well. Wells containing only $T_0$ culture (200 200 μL/well) are used to determine pyocyanin control level and wells containing only LB broth (blank wells) are also included in the plate.

The plate is sealed and incubated at 37° C. under shaking (~700 rpm) using a microtiter shaker for 24 hours. At the end of the incubation period, the plate is centrifuged at 4,000 g for 40 minutes at room temperature, 100 µL/well of the supernatant is transferred to a 96-microtiter PS flat-bottom plate, and absorbance at 690 nm is determined using SPECTROstar® Nano microplate reader. Pyocyanin concentration (M) is determined using the equation $C=A_{690}/(\epsilon \times d)$, where $\epsilon$ is the Pyocyanin extinction coefficient, at $A_{690}$ nm $\epsilon$ is 4,310 $M^{-1}$ $cm^{-1}$ and d is the experimentally derived pathlength. The level of pyocyanin in the presence of test compound is expressed as percentage of inhibition with respect to the control. Curve fitting and $IC_{50}$ determination were carried out using a four-parameter logistic model using GraphPad Prism v.5.

Pyocyanin inhibition data is provided in Table 5. Three stars (*) indicates an $IC_{50}$<0.1 µM, two stars () indicates 0.1 µM≤$IC_{50}$<1.0 µM, one star (*) indicates 1.0 µM≤$IC_{50}$≤10.0 µM, no stars beside a compound number indicates that compound has an $IC_{50}$>10 µM.

TABLE 5

| Compound No. | Pyocyanin Inhibition No. IC$_{50}$ (µM) |
|---|---|
| 23 | * |
| 56 | *** |
| 57 | ** |
| 71 | ** |
| 72 | |
| 73 | |
| 74 | ** |
| 75 | |
| 76 | *** |
| 77 | *** |
| 78 | *** |
| 79 | *** |
| 80 | *** |
| 81 | *** |
| 82 | *** |
| 83 | *** |
| 84 | *** |
| 85 | ** |
| 86 | ** |
| 87 | |
| 88 | |
| 89 | ** |
| 90 | * |
| 91 | |
| 92 | |
| 93 | ** |
| 94 | ** |
| 95 | * |
| 96 | *** |
| 97 | |
| 98 | |
| 99 | |
| 100 | |
| 101 | |
| 102 | |
| 103 | |
| 104 | ** |
| 105 | ** |
| 106 | |
| 107 | |
| 108 | |
| 109 | |
| 110 | ** |
| 111 | |
| 112 | |
| 113 | |
| 114 | |
| 115 | |
| 116 | ** |
| 117 | * |
| 118 | |
| 119 | |

TABLE 5-continued

| Compound No. | Pyocyanin Inhibition No. IC$_{50}$ (µM) |
|---|---|
| 120 | |
| 121 | |
| 122 | |
| 123 | |
| 124 | |
| 125 | *** |
| 126 | ** |
| 127 | |
| 128 | |
| 129 | |
| 130 | |
| 131 | |
| 132 | |
| 133 | |
| 134 | * |
| 135 | |
| 136 | |
| 137 | ** |
| 138 | |
| 139 | * |
| 140 | ** |
| 141 | * |
| 142 | ** |
| 143 | * |
| 144 | * |
| 145 | ** |
| 146 | |
| 147 | ** |
| 148 | * |
| 149 | * |
| 150 | * |
| 151 | |
| 152 | ** |
| 153 | |
| 154 | |
| 155 | |
| 156 | |
| 157 | |
| 158 | |
| 159 | ** |
| 160 | * |
| 161 | *** |
| 162 | *** |
| 163 | ** |
| 164 | *** |
| 165 | *** |
| 166 | ** |
| 167 | ** |
| 168 | ** |
| 169 | ** |
| 170 | *** |
| 171 | *** |
| 172 | * |

Example 23

PQS Inhibition Assay (24 Hour Incubation)

Test compounds are dissolved in DMSO at 10 mM and stored at −20° C. until needed. Seven test concentrations from 0.0032 micromolar to 31.6 micromolar are used for each compound. *P. aeruginosa* PA14 wild-type strain is inoculated into 5 mL LB broth in a 15-mL sterile glass culture tube and incubated overnight at 37° C. under shaking (~240 rpm). The overnight culture is then diluted in LB Broth to give an $OD_{600}$=0.04 ($T_0$ culture). Colony Forming Units (CFU)/mL of the overnight culture and $T_0$ culture are determined by a series of 1:10 serial dilutions in sterile saline. 4×20 µL of each dilution is seeded on LB agar plates and incubated at 35±2° C. for 20 hours. CFU/mL is determined from the dilution that gives 2 to 50 colonies/20 µL.

For concentration response curve (CRC) experiments, internal standard (2-((5-nitro-1H-indol-2-yl)thio)-N-(4-phenoxyphenyl)acetamide)) and test compounds are serially diluted in DMSO to give 200 times of each final concentration (0.5% DMSO final), and 1 μL/well is dispensed in duplicate into 2-mL wells of a 96 well deep well plate. 200 μL/well of T$_0$ culture is added to each internal standard/test compound well used to determine PQS control level. Wells containing only LB broth (blank wells) are also included in the plate.

The plate is sealed and incubated at 37° C. for 24 hours under shaking (~700 rpm) using a microtiter shaker. At the end of the incubation period, 150 μL/well of the deep well plate culture are transferred in a new non-sterile plate, and 150 μL/well of methanol containing tetra-deuterated PQS (D4-PQS) and 2% acetic acid are added to each well. The plate is sealed, shaken at high speed for 5 minutes and centrifuged at 4,000 g for 40 minutes at room temperature. 100 μL/well of the supernatant is then transferred to glass vials (vials crimp 0.2 mL) and kept at 4° C. until LC-MS/MS analysis.

PQSs quantification is carried out by analyzing samples in discrete batches together with spiked standards and blank samples.

Calibration curves are constructed from PQS standards, and respective deuterated PQS is used as an Internal Standards (IS) to calculate the concentration of analytes in the sample and improve the precision of the assay. The back-calculated concentrations of the calibration standards from the calibration curve shall be within ±20% of the nominal values, the range of the analytical method is determined, and the lower and upper limit of quantification specified.

Liquid chromatography separations are performed using an Agilent HP1100 system (Agilent Technologies) coupled with a CTC PAL Autosampler (CTC Analytics AG). Chromatographic retention is obtained using a monolithic column (Chromolith® RP-18, 50×4.6 mm). The solvent system consists of water containing 0.1% (v/v) formic acid (A) and acetonitrile containing 0.1% (v/v) formic acid (B). The gradient elution profile is chosen as follows: 0 min: 70% A (1500 μL/min), 0.3 min: 70% A (1500 μL/min), 1.3 min: 5% A (2500 μL/min), 1.6 min: 5% A (2500 μL/min).

The MS/MS analysis is performed with an API4000 series mass spectrometer (AB Sciex™) operating in Multiple Reaction Monitoring (MRM) mode and equipped with a TIS ion source. The specific ions monitored are PQS (m/z 260→m/z 175) and D4-PQS (m/z 264→m/z 179). The computer systems used in this study to acquire and quantify data may be an Analyst™ v1.5.

PQS in the presence of different concentrations of test compound are expressed as percentage of inhibition of the basal level in control samples. Curve fitting and IC$_{50}$ estimations are carried out using a four parameter logistic model using GraphPad Prism v.5 program.

PQS 24 hour inhibition data is provided in Table 6. Typically compounds that exhibited an IC$_{50}$ of less than 10 micromolar in the Pyocyanin inhibition assay were tested in the PQS 24 hour inhibition assay. Three stars (*) indicates an IC$_{50}$<1.0 μM, two stars () indicates 1.0 μM≤IC$_{50}$<5.0 μM, one star (*) indicates 5.0 μM≤IC$_{50}$<10.0 μM, no stars beside a compound number indicates that compound has an IC$_{50}$>10 μM.

TABLE 6

| Compound No. | PQS (24 hr) IC$_{50}$ (μM) |
| --- | --- |
| 23 | |
| 56 | *** |
| 57 | ** |
| 71 | * |
| 72 | |
| 73 | |
| 74 | ** |
| 75 | |
| 76 | *** |
| 77 | *** |
| 78 | *** |
| 79 | *** |
| 80 | *** |
| 81 | *** |
| 82 | *** |
| 83 | *** |
| 84 | ** |
| 85 | |
| 86 | |
| 87 | |
| 88 | |
| 89 | * |
| 90 | |
| 91 | |
| 92 | |
| 93 | *** |
| 94 | ** |
| 95 | |
| 96 | *** |
| 104 | * |
| 105 | ** |
| 106 | |
| 110 | * |
| 111 | |
| 112 | |
| 113 | |
| 116 | |
| 117 | |
| 125 | *** |
| 126 | |
| 134 | ** |
| 135 | |
| 136 | |
| 137 | ** |
| 138 | |
| 139 | |
| 140 | * |
| 141 | |
| 142 | *** |
| 143 | * |
| 144 | |
| 145 | |
| 146 | |
| 147 | ** |
| 148 | * |
| 149 | |
| 150 | |
| 151 | |
| 152 | ** |
| 153 | |
| 154 | |
| 155 | |
| 156 | |
| 157 | |
| 158 | |

Example 24

Assay for PQS and HHQ Inhibition (6 Hour Incubation)

A concentration range with 7 test concentrations is chosen for each test compound. Typically concentration ranges for the PQS and HHQ assays are from 0.03 to 31.6 μM.

Compounds are prepared in solvent, usually DMSO, at either 200 or 500 times the final test concentration.

*P. aeruginosa* PA14 wild-type strain is inoculated into 5 ml LB broth in a 15 ml sterile glass culture tube and incubated overnight at 37° C. under shaking (~240 rpm). After overnight incubation, the bacterial culture is diluted in fresh LB broth to an OD600 nm=0.04, and 5 mL aliquots of the diluted bacterial culture are distributed into 15-mL glass tubes. 10 µL of test compound at 500 times the final test concentration or 25 µL of test compound at 200 times the final test concentration or solvent alone is added to each of the bacterial suspension tubes, and the tubes are incubated at 37° C. under shaking (300 rpm) for 6 hours. At the end of the incubation period, a 0.5 mL aliquot of bacterial suspension is transferred from each 15 mL glass tube, after shaking, to a 2 mL polypropylene vial. 0.5 mL of methanol-containing D4-PQS (deuterated-PQS), D4-HHQ (deuterated-HHQ) and 2% acetic acid are added to each 2 mL vial and each vial is vigorously shaken. The vials are then centrifuged for 5 minutes at 12,000 g, and 200 µL of supernatant from each vial is transferred to a glass vial (vials crimp 0.2 mL), and the sealed vials are kept at 4° C. until LC-MS/MS analysis is performed. HAQs quantification is carried out analyzing samples in discrete batches together with spiked standards and blank samples. Calibration curves are constructed from HAQs standards, and respective deuterated forms are used as Internal Standards (IS), to calculate the concentration of analytes in the sample and improve the precision of the assay. The back-calculated concentrations of the calibration standards from the calibration curve shall be within ±20% of the nominal values, the range of the analytical method is determined, and the lower and upper limit of quantification specified.

Liquid chromatography separations are performed using Agilent HP1100 system (Agilent Technologies) coupled with a CTC PAL Autosampler (CTC Analytics AG). Chromatographic retention is obtained using a monolithic column (Chromolith® RP-18, 50×4.6 mm). The solvent system consists of water containing 0.1% (v/v) formic acid (A) and acetonitrile containing 0.1% (v/v) formic acid (B). The gradient elution profile is chosen as follows: 0 min: 70% A (1500 µL/min), 0.3 min: 70% A (1500 µL/min), 1.3 min: 5% A (2500 µL/min), 1.6 min: 5% A (2500 µL/min).

The MS/MS analysis is performed with a API4000 series mass spectrometer (AB Sciex™) operating in Multiple Reaction Monitoring (MRM) mode and equipped with a TIS ion source. The specific ions monitored are PQS (m/z 260→m/z 175), D4-PQS (m/z 264→m/z 179), HHQ (m/z 244→m/z 159) and D4-HHQ (m/z 248→m/z 163). PQS and HHQ in presence of different test compound concentrations are expressed as percentage of inhibition of the basal level in control samples.

PQS 6 hour inhibition data is provided in Table 7. HHQ 6 hour inhibition data is provided in Table 8. Typically compounds that exhibited an $IC_{50}$ of less than 1 micromolar in the Pyocyanin inhibition assay were tested in the PQS and HHQ 6 hour inhibition assays. Three stars (*) indicates an $IC_{50}$<1.0 µM, two stars () indicates 1.0 µM≤$IC_{50}$<5.0 µM, one star (*) indicates 5.0 µM≤$IC_{50}$<10.0 µM, no stars beside a compound number indicates that compound has an $IC_{50}$>10 µM.

TABLE 7

| Compound No. | PQS (6 hr) $IC_{50}$ (µM) |
|---|---|
| 56 | *** |
| 57 | ** |
| 71 | ** |
| 74 | ** |
| 77 | *** |
| 79 | *** |
| 83 | *** |
| 84 | *** |
| 85 | ** |
| 86 | |
| 93 | ** |
| 94 | ** |
| 96 | *** |
| 104 | ** |
| 105 | *** |
| 110 | ** |
| 116 | |
| 125 | *** |
| 126 | ** |
| 137 | *** |
| 140 | * |
| 142 | *** |
| 145 | *** |
| 147 | *** |
| 152 | *** |
| 159 | *** |

TABLE 8

| Compound No. | HHQ (6 hr) $IC_{50}$ (µM) |
|---|---|
| 56 | *** |
| 57 | ** |
| 71 | ** |
| 74 | *** |
| 77 | *** |
| 79 | *** |
| 83 | *** |
| 84 | *** |
| 85 | ** |
| 86 | |
| 93 | *** |
| 94 | ** |
| 96 | *** |
| 104 | ** |
| 105 | *** |
| 110 | ** |
| 116 | |
| 125 | *** |
| 137 | *** |
| 142 | *** |
| 145 | *** |
| 147 | *** |
| 152 | *** |
| 159 | *** |

What is claimed is:

1. A method for treating a Gram negative bacterial infection in a subject comprising administering to the subject a composition comprising a compound of Formula VIII:

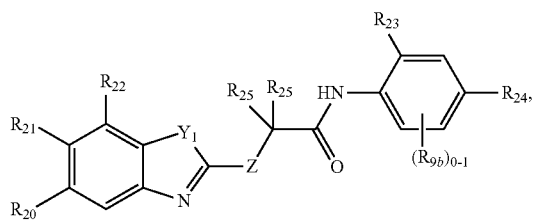

(VIII)

or a pharmaceutically acceptable salt thereof; and a pharmaceutically acceptable carrier, wherein:
  each of $R_{20}$ and $R_{21}$ is independently selected from hydrogen, chloro, fluoro, bromo, cyano, —OCHF$_2$, and CF$_3$, wherein at least one of $R_{20}$ or $R_{21}$ is other than hydrogen;
  $R_{22}$ is selected from hydrogen, chloro, fluoro, bromo, methyl, ethyl, —OCH$_3$, —OCH$_2$CH$_3$, CF$_3$, and CHF$_2$
  $Y_1$ is selected from NH, O and S;
  Z is selected from CH$_2$, NH and S;
  $R_{23}$ is selected from hydrogen, chloro, fluoro, bromo, methyl, ethyl, hydroxy, —OCH$_3$, —OCH$_2$CH$_3$, CF$_3$, and CHF$_2$
  $R_{24}$ is selected from chloro, fluoro, bromo, cyano, —OCH$_3$, optionally substituted pyridinyloxy, optionally substituted pyrimidinyloxy, optionally substituted pyrazinyloxy, and optionally substituted pyridazinyl;
  each $R_{25}$ is independently selected from hydrogen, hydroxy, halogen, C$_1$-C$_4$ alkyl, and C$_1$-C$_4$ haloalkyl;
  $R_{9b}$, if present, is selected from bromo, chloro and fluoro, wherein:
when $R_{24}$ is optionally substituted pyridinyloxy, optionally substituted pyrimidinyloxy, optionally substituted pyrazinyloxy, or optionally substituted pyridazinyl, Z is S and $Y_1$ is NH, then each of $R_{20}$ and $R_{21}$ is other than hydrogen or cyano.

2. The method of claim 1, wherein in the compound of Formula VIII:
  $R_{9b}$ is absent or chloro;
  $R_{20}$ is selected from hydrogen, bromo, fluoro, chloro, cyano, OCHF$_2$, CF$_3$;
  $R_{21}$ is selected from hydrogen, bromo, chloro, fluoro, and cyano;
  $R_{22}$ is selected from hydrogen and —OCH$_3$;
  $R_{23}$ is selected from hydrogen, chloro, hydroxy, methyl, —OCH3;
  $R_{24}$ is selected from chloro, fluoro, bromo, cyano, —OCH$_3$, pyridin-3-yloxy, 4-methylpyridin-3-yloxy, 5-methylpyridin-3-yloxy, 6-methylpyridin-3-yloxy, 6-chloropyridin-3-yloxy, pyridin-4-yloxy, pyrazin-4-yloxy, pyrazin-2-yloxy, and pyrimidin-2-yloxy; and
  each $R_{25}$ is hydrogen.

3. A pharmaceutical composition comprising a compound of Formula VIII:

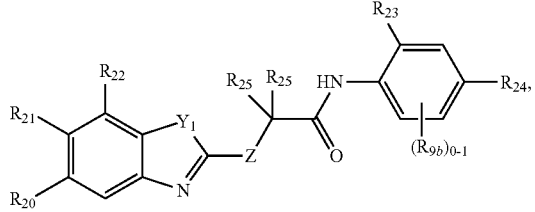

(VIII)

or a pharmaceutically acceptable salt thereof, wherein:
  each of $R_{20}$ and $R_{21}$ is independently selected from hydrogen, chloro, fluoro, bromo, cyano, —OCHF$_2$, and CF$_3$, wherein at least one of $R_{20}$ or $R_{21}$ is other than hydrogen;
  $R_{22}$ is selected from hydrogen, chloro, fluoro, bromo, methyl, ethyl, —OCH$_3$, —OCH$_2$CH$_3$, CF$_3$, and CHF$_2$
  $Y_1$ is selected from NH, O and S;
  Z is selected from CH$_2$, NH and S;
  $R_{23}$ is selected from hydrogen, chloro, fluoro, bromo, methyl, ethyl, hydroxy, —OCH$_3$, —OCH$_2$CH$_3$, CF$_3$, and CHF$_2$
  $R_{24}$ is selected from chloro, fluoro, bromo, cyano, —OCH$_3$, optionally substituted pyridinyloxy, optionally substituted pyrimidinyloxy, optionally substituted pyrazinyloxy, and optionally substituted pyridazinyl;
  each $R_{25}$ is independently selected from hydrogen, hydroxy, halogen, C$_1$-C$_4$ alkyl, and C$_1$-C$_4$ haloalkyl; and
  $R_{9b}$, if present, is selected from bromo, chloro and fluoro, wherein:
when $R_{24}$ is optionally substituted pyridinyloxy, optionally substituted pyrimidinyloxy, optionally substituted pyrazinyloxy, or optionally substituted pyridazinyl, each $R_{25}$ is hydrogen, Z is S and $Y_1$ is NH, then each of $R_{20}$ and $R_{21}$ is other than hydrogen or cyano; and
wherein the compound is other than

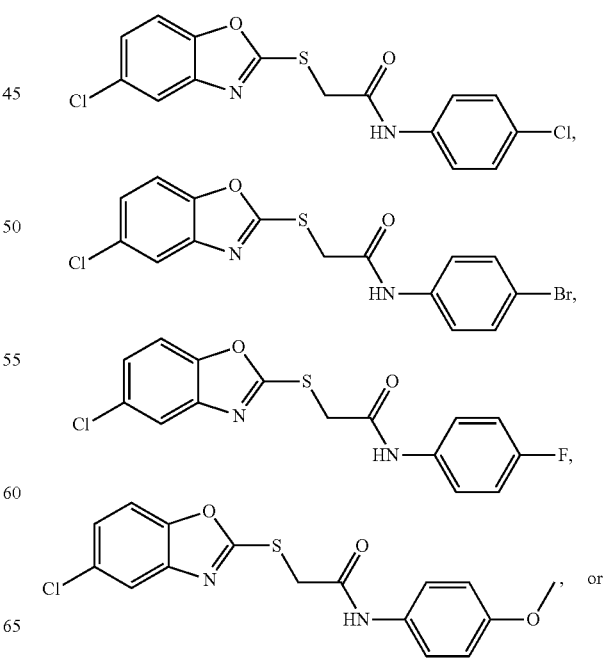

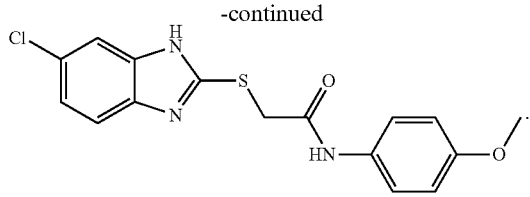

4. The composition of claim 3, wherein in Formula VIII:
$R_{9b}$ is absent or chloro;
$R_{20}$ is selected from hydrogen, bromo, fluoro, chloro, cyano, $OCHF_2$, $CF_3$;
$R_{21}$ is selected from hydrogen, bromo, chloro, fluoro, and cyano;
$R_{22}$ is selected from hydrogen and $-OCH_3$;
$R_{23}$ is selected from hydrogen, chloro, hydroxy, methyl, $-OCH_3$;
$R_{24}$ is selected from chloro, fluoro, bromo, cyano, $-OCH_3$, pyridin-3-yloxy, 4-methylpyridin-3-yloxy, 5-methylpyridin-3-yloxy, 6-methylpyridin-3-yloxy, 6-chloropyridin-3-yloxy, pyridin-4-yloxy, pyrazin-4-yloxy, pyrazin-2-yloxy, and pyrimidin-2-yloxy; and
each $R_{25}$ is hydrogen.

5. A compound of Formula VIII:

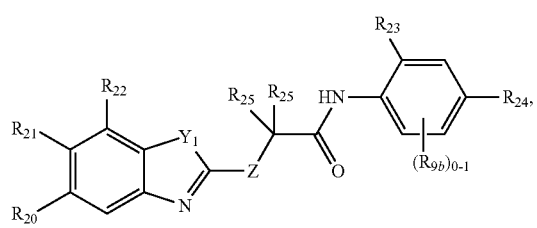

or a pharmaceutically acceptable salt thereof, wherein:
each of $R_{20}$ and $R_{21}$ is independently selected from hydrogen, chloro, fluoro, bromo, cyano, $-OCHF_2$, and $CF_3$, wherein at least one of $R_{20}$ or $R_{21}$ is other than hydrogen;
$R_{22}$ is selected from hydrogen, chloro, fluoro, bromo, methyl, ethyl, $-OCH_3$, $-OCH_2CH_3$, $CF_3$, and $CHF_2$
$Y_1$ is selected from NH, O and S;
Z is selected from S, $CH_2$, and NH;
$R_{23}$ is selected from hydrogen, chloro, fluoro, bromo, methyl, ethyl, hydroxy, $-OCH_3$, $-OCH_2CH_3$, $CF_3$, and $CHF_2$
$R_{24}$ is selected from chloro, fluoro, bromo, cyano, $-OCH_3$, optionally substituted pyridinyloxy, optionally substituted pyrimidinyloxy, optionally substituted pyrazinyloxy, and optionally substituted pyridazinyl;
each $R_{25}$ is independently selected from hydrogen, hydroxy, halogen, $C_1$-$C_4$ alkyl, and $C_1$-$C_4$ haloalkyl; and
$R_{9b}$, if present, is selected from bromo, chloro and fluoro, wherein:
when $R_{24}$ is optionally substituted pyridinyloxy, optionally substituted pyrimidinyloxy, optionally substituted pyrazinyloxy, or optionally substituted pyridazinyl, Z is S, and $Y_1$ is NH, then each of $R_{20}$ and $R_{21}$ is other than hydrogen or cyano;
when $R_{24}$ is chloro, fluoro, bromo, or $-OCH_3$, $R_{22}$ is hydrogen, and Z is S, neither of $R_{20}$ or $R_{21}$ is chloro, fluoro, or bromo; and the compound is other than

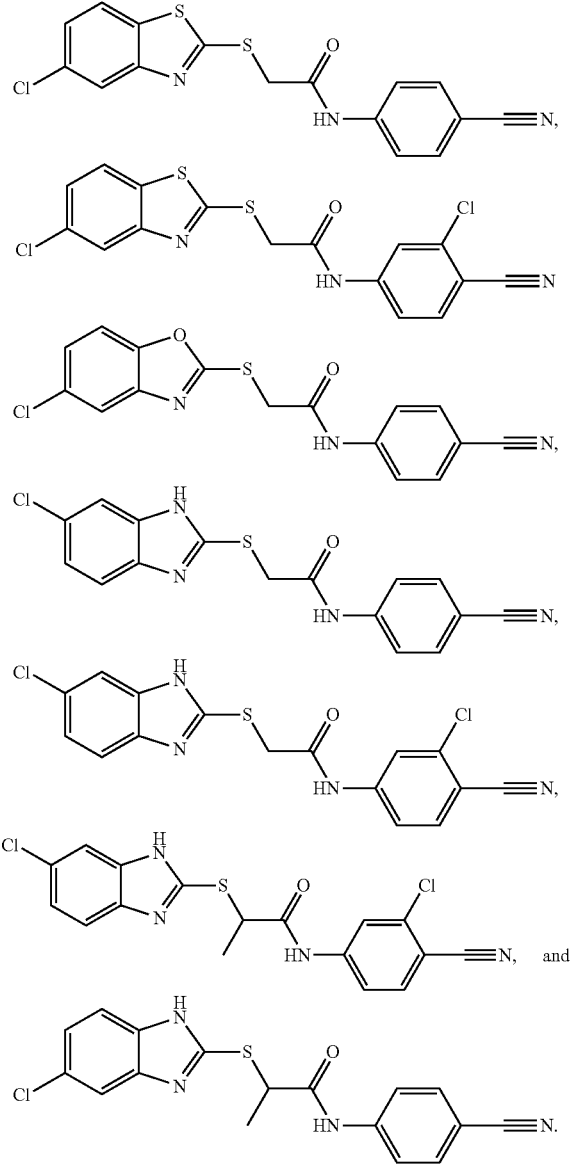

6. The compound of claim 5, or a pharmaceutically acceptable salt thereof, wherein in Formula VIII Z is S.
7. The compound of claim 5, or a pharmaceutically acceptable salt thereof, wherein in Formula VIII Z is NH or $CH_2$.
8. The compound of claim 5, or a pharmaceutically acceptable salt thereof, wherein in Formula VIII:
$R_{9b}$ is absent or chloro;
$R_{20}$ is selected from hydrogen, bromo, fluoro, chloro, cyano, $OCHF_2$, $CF_3$;
$R_{21}$ is selected from hydrogen, bromo, chloro, fluoro, and cyano;
$R_{22}$ is selected from hydrogen and $-OCH_3$;
$R_{23}$ is selected from hydrogen, chloro, hydroxy, methyl, $-OCH_3$;
$R_{24}$ is selected from chloro, fluoro, bromo, cyano, $-OCH_3$, pyridin-3-yloxy, 4-methylpyridin-3-yloxy, 5-methylpyridin-3-yloxy, 6-methylpyridin-3-yloxy, 6-chloropyridin-3-yloxy, pyridin-4-yloxy, pyrazin-4-yloxy, pyrazin-2-yloxy, and pyrimidin-2-yloxy; and each $R_{25}$ is hydrogen.

9. The method of claim 1, wherein the Gram negative bacterial infection is selected from an infection caused by *Burkholderia* sp., *Acinetobacter* sp., *Klebsiella* sp. and *Pseudomonas* sp.

10. The method of claim 9, wherein the Gram negative bacterial infection is an infection caused by *Pseudomonas* sp.

11. The method of claim 10, wherein the Gram negative bacterial infection is an infection caused by *Pseudomonas aeruginosa*.

* * * * *

UNITED STATES PATENT AND TRADEMARK OFFICE
CERTIFICATE OF CORRECTION

| | | |
|---|---|---|
| PATENT NO. | : 9,643,933 B2 | Page 1 of 1 |
| APPLICATION NO. | : 14/786345 | |
| DATED | : May 9, 2017 | |
| INVENTOR(S) | : Robert Zahler, Ronald Thure Wester and Steven Joseph Brickner | |

It is certified that error appears in the above-identified patent and that said Letters Patent is hereby corrected as shown below:

In the Specification

Column 1, Line 12, delete "bet-hall" and insert -- all --,

In the Claims

Column 121, Line 57, in Claim 2, delete "-OCH3;" and insert -- -OCH$_3$; --.

Signed and Sealed this
Twenty-seventh Day of March, 2018

Andrei Iancu
*Director of the United States Patent and Trademark Office*

UNITED STATES PATENT AND TRADEMARK OFFICE
CERTIFICATE OF CORRECTION

PATENT NO. : 9,643,933 B2  
APPLICATION NO. : 14/786345  
DATED : May 9, 2017  
INVENTOR(S) : Robert Zahler, Ronald Thure Wester and Steven Joseph Brickner Page 1 of 1

It is certified that error appears in the above-identified patent and that said Letters Patent is hereby corrected as shown below:

In the Claims

In Column 124, Line 45, Claim 5, delete " 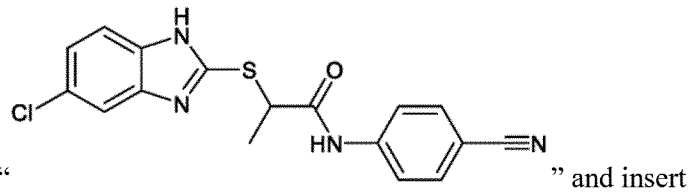 " and insert 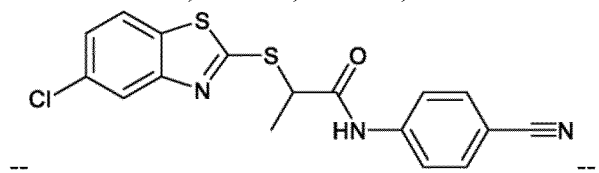 -- --

Signed and Sealed this  
First Day of September, 2020

Andrei Iancu  
*Director of the United States Patent and Trademark Office*